(12) United States Patent
Kang et al.

(10) Patent No.: US 11,439,731 B2
(45) Date of Patent: *Sep. 13, 2022

(54) ARTIFICIAL TISSUE PROGENITOR AND METHOD FOR PREPARING THE SAME

(71) Applicant: REVOTEK CO., LTD, Sichuan (CN)

(72) Inventors: Yujian James Kang, Sichuan (CN); Xiao Zuo, Sichuan (CN); Mingchun Du, Sichuan (CN)

(73) Assignee: REVOTEK CO., LTD., Sichuan (CN)

(*) Notice: Subject to any disclaimer, the term of this patent is extended or adjusted under 35 U.S.C. 154(b) by 0 days.

This patent is subject to a terminal disclaimer.

(21) Appl. No.: 16/113,509

(22) Filed: Aug. 27, 2018

(65) Prior Publication Data

US 2019/0038809 A1 Feb. 7, 2019

Related U.S. Application Data

(63) Continuation-in-part of application No. 15/780,301, filed as application No. PCT/CN2017/101738 on Sep. 14, 2017.

(30) Foreign Application Priority Data

Sep. 14, 2016 (CN) .......................... 201610821050.5
Sep. 14, 2016 (CN) .......................... 201610822810.4
Sep. 14, 2016 (CN) .......................... 201610822901.8
Sep. 14, 2016 (WO) ................ PCT/CN2016/099002
Nov. 11, 2016 (CN) .......................... 201611040230.6

(51) Int. Cl.
| | |
|---|---|
| A61L 27/50 | (2006.01) |
| A61L 27/36 | (2006.01) |
| A61L 27/38 | (2006.01) |
| C12N 5/0775 | (2010.01) |
| C12N 5/00 | (2006.01) |
| C12M 1/12 | (2006.01) |
| C12M 3/00 | (2006.01) |
| C12N 5/071 | (2010.01) |
| B33Y 80/00 | (2015.01) |
| C12M 1/26 | (2006.01) |
| B33Y 10/00 | (2015.01) |
| A61L 27/18 | (2006.01) |

(52) U.S. Cl.
CPC .............. *A61L 27/507* (2013.01); *A61L 27/18* (2013.01); *A61L 27/3625* (2013.01); *A61L 27/3834* (2013.01); *B33Y 10/00* (2014.12); *B33Y 80/00* (2014.12); *C12M 21/08* (2013.01); *C12M 25/14* (2013.01); *C12M 25/16* (2013.01); *C12M 33/00* (2013.01); *C12N 5/0012* (2013.01); *C12N 5/0068* (2013.01); *C12N 5/0667* (2013.01); *C12N 5/0691* (2013.01); *A61F 2210/0004* (2013.01); *A61F 2230/0063* (2013.01); *C12N 2513/00* (2013.01); *C12N 2533/30* (2013.01); *C12N 2533/54* (2013.01); *C12N 2533/56* (2013.01)

(58) Field of Classification Search
CPC .............. A61L 27/507; A61L 27/3834; A61L 27/3625; C12N 5/0012; C12N 5/0667; C12N 2533/54; C12M 21/08; C12M 25/14

See application file for complete search history.

(56) References Cited

U.S. PATENT DOCUMENTS

| | | | |
|---|---|---|---|
| 5,104,403 A * | 4/1992 | Brotzu ....................... | A61F 2/06 623/1.4 |
| 8,697,057 B2 | 4/2014 | Van Epps et al. | |
| 2006/0198865 A1 | 9/2006 | Freyman et al. | |
| 2012/0253456 A1* | 10/2012 | Shin ...................... | C12N 5/0691 623/1.42 |
| 2013/0164339 A1 | 6/2013 | Murphy et al. | |

(Continued)

FOREIGN PATENT DOCUMENTS

| | | |
|---|---|---|
| CN | 1609200 A | 4/2005 |
| CN | 101260160 A | 4/2008 |

(Continued)

OTHER PUBLICATIONS

Silvestri et al. Octyl-2-Cyanoacrylate Adhesive for Skin Closure and Prevention of Infection in Plastic Surgery. Aesth. Plast. Surg. 30:695-699 (Year: 2006).*

Rath et al. Mucoadhesive Systems in Dentistry: A Review. International Journal of Dental Research, 4 (2) (2016) 25-29 (Year: 2016).*

Tsuji et al. Adipose-derived stem cells: Implications in tissue regeneration. World J Stem Cells Jul. 26, 2014; 6(3): 312-321 (Year: 2014).*

(Continued)

*Primary Examiner* — Taeyoon Kim
(74) *Attorney, Agent, or Firm* — Scully, Scott, Murphy & Presser, P.C.

(57) ABSTRACT

The invention relates to the technical filed of tissue engineering and 3D printing, particularly relates to an artificial tissue progenitor and a method for preparing the same. In particular, the invention relates to an artificial tissue progenitor comprising a solid support and a plurality of microcapsules, wherein at least one microcapsule is attached to the solid support, and the microcapsule comprises a cell and a biocompatible material encapsulating the cell, to a method for preparing the artificial tissue progenitor, to a kit and a package useful for preparing the artificial tissue progenitor, to an artificial tissue obtained by culturing the artificial tissue progenitor, such as an artificial lumen, to a lumen implant or a lumen model containing the artificial tissue progenitor or the artificial lumen, to use of the artificial tissue progenitor in the manufacture of an artificial tissue, a lumen implant or a lumen model, and to use of the artificial tissue in the manufacture of a lumen implant or lumen model.

14 Claims, 26 Drawing Sheets

(56) References Cited

U.S. PATENT DOCUMENTS

| | | | |
|---|---|---|---|
| 2014/0100648 A1* | 4/2014 | Matheny | A61L 27/507 623/1.13 |
| 2014/0127290 A1 | 5/2014 | He et al. | |
| 2015/0037445 A1 | 2/2015 | Murphy et al. | |
| 2017/0216498 A1 | 8/2017 | Kang et al. | |

FOREIGN PATENT DOCUMENTS

| | | |
|---|---|---|
| CN | 101259292 A | 9/2008 |
| CN | 101829361 A | 9/2010 |
| CN | 102070895 A | 5/2011 |
| CN | 102573942 A | 7/2012 |
| CN | 103272288 A | 9/2013 |
| CN | 103756955 A | 4/2014 |
| CN | 103930066 A | 7/2014 |
| CN | 103946374 A | 7/2014 |
| CN | 104783923 A | 7/2015 |
| CN | 106039412 A | 10/2016 |
| CN | 106039414 B | 7/2020 |
| EP | 0 406 665 A1 | 1/1991 |
| EP | 1 759 720 A1 | 3/2007 |
| JP | 1-170467 | 7/1989 |
| JP | 3-41948 | 2/1991 |
| JP | 2003126125 A | 5/2003 |
| JP | 2004-506418 A | 3/2004 |
| JP | 2007-89737 A | 4/2007 |
| JP | 2007-307300 A | 11/2007 |
| JP | 2008-533015 A | 8/2008 |
| JP | 2012-524739 A | 10/2012 |
| JP | 5674442 B2 | 1/2015 |
| KR | 10-1472045 B1 | 12/2014 |
| KR | 101472045 B1 | 12/2014 |
| WO | 02/07646 A2 | 1/2002 |
| WO | 2005/118013 A1 | 12/2005 |
| WO | 2006/096688 A2 | 9/2006 |
| WO | 2010/124837 A2 | 11/2010 |
| WO | 2013/040078 A2 | 3/2013 |
| WO | 2015/123183 A1 | 8/2015 |
| WO | 2016/115034 A1 | 7/2016 |

OTHER PUBLICATIONS

Kumar et al. Bioadhesive polymers: Novel tool for drug delivery. Artificial Cells, Nanomedicine, and Biotechnology, 2014; 42: 274-283 (Year: 2014).*

Petrie. Cyanoacrylate Adhesives in Surgical Applications: A Critical Review. Rev. Adhesion Adhesives, vol. 2, No. 3, Aug. 2014. p. 253-310 (Year: 2014).*

International Search Report dated Dec. 20, 2017 received in International Application No. PCT/CN2017/101738, together with an English-language translation.

Boland, T. et al., "Application of Inkjet Printing to Tissue Engineering", Biotechnol. J., vol. 1, pp. 910-917 (2006).

Gong, Y., "Approaching the magical stem cell transplantation", Xi'an Jiaotong University Press, pp. 96-98 (May 26, 2014), full text in Chinese with key point in English.

Gomez, C.G. et al., "Oxidation of sodium alginate and characterization of the oxidized derivatives", Carbohydrate Polymers, vol. 67, pp. 296-304 (2007).

He, S. et al., "Preparation and Characterization of Partially Oxidized Sodium Alginate", Chinese Journal of Applied Chemistry, 22(9):1007-1011 (Sep. 2005), together with English abstract.

Kim, C. et al., "Generation of core-shell microcapsules with three-dimensional focusing device for efficient formation of cell spheroid", Lab Chip, vol. 11, pp. 246-252 (2011).

Extended European Search Report dated Dec. 19, 2019 issued in European Patent Application No. 17850294.4.

Luo, Y., et. al, "Direct Plotting of Three-Dimensional Hollow Fiber Scaffolds Based on Concentrated Alginate Pastes for Tissue Engineering", Advanced Healthcare Materials, 2:777-783, (2013).

Nakamura, M., et. al., "Biomatrices and biomaterials for future developments of bioprinting and biofabrication", International Society for Biofabrication, vol. 2, 6 pages (2010).

Onoe, H., et. al., "Metre-long cell-laden microfibres exhibit tissue morphologies and functions", Nature Materials, pp. 1-7, (2013).

Perez, R., et. al., "Utilizing Core-Shell Fibrous Collagen-Alginate Hydrogel Cell Delivery System for Bone Tissue Engineering", Tissue Engineering: Part A, 20(1-2):103-114, (2013).

Skardal, A., et. al., "Photocrosslinkable Hyaluronan-Gelatin Hydrogels for Two-Step Bioprinting", Tissue Engineering: Part A, 16(8):2675-2685, (2010).

Yeo, M., et. al., "An Innovative Collagen-Based Cell-Printing Method for Obtaining Human Adipose Stem Cell-Laden Structures Consisting of Core-Sheath Structures for Tissue Engineering", American Chemical Society, 17:1365-1375, (2016).

Japanese Notice of Reasons for Rejection dated Sep. 3, 2019 received in Japanese Patent Application No. 2018-528046, together with an English-language translation.

Ali S. et al., "Immobilization of Cell-Adhesive Laminin Peptides in Degradable PEGDA Hydrogels Influences Endothelial Cell Tubulogenesis", BioResearch Open Access 2(4):241-249 (Aug. 2013).

Bertolini F. et al., "Adipose Tissue Cells, Lipotransfer and Cancer: A Challenge for Scientists, Oncologists and Surgeons", Biochimica et Biophysica Acta 1826:209-214 (2012).

Bhatia M., "Microenvironment Mimicry", Science 329:1024-1025 (Aug. 27, 2010).

Bilic J. et al., "Concise Review: Induced Pluripotent Stem Cells Versus Embryonic Stem Cells: Close Enough or Yet Too Far Apart?", Stem Cells 30:33-41 (2012).

Bozza A. et al., "Neural Differentiation of Pluripotent Cells in 3D Alginate-Based Cultures", Biomaterials 35:4636-4645 (2014).

Brzoska M. et al., "Epithelial Differentiation of Human Adipose Tissue-Derived Adult Stem Cells", Biochemical and Biophysical Communications 330:142-150 (2005).

Buchanan C.F. et al., "Three-Dimensional Microfluidic Collagen Hydrogels for Investigating Flow-Medicated Tumor Endothelial Signaling and Vascular Organization", Tissue Engineering Part C 20(1):64-75 (2014).

Cao Y. et al., "Human Adipose Tissue-Derived Stem Cells Differentiate into Endothelial Cells In Vitro and Improve Postnatal Neovascularization In Vivo", Biochemical and Biophysical Research Communications 332:370-379 (2005).

Caplan A.I. et al., "The MSC: An Injury Drugstore", Cell Stem Cell 9:11-15 (Jul. 8, 2011).

Caplan A.I. et al., "Mesenchymal Stem Cells as Trophic Mediators", Journal of Cellular Biochemistry 98:1076-1084 (2006).

Chin M.H. et al., "Induced Pluripotent Stem Cells and Embryonic Stem Cells are Distinguished by Gene Expression Signatures", Cell Stem Cell5:111-123 (Jul. 2, 2009).

Cowan C.M. et al., "Adipose-Derived Adult Stromal Cells Heal Critical-Size Mouse Calvarial Defects", Nature Biotechnology 22(5):560-567 (May 2004).

Dulak J. et al., "Adult Stem Cells: Hopes and Hypes of Regenerative Medicine", ACTA Biochimica Polonica 62(3):329-337 (2015).

Erickson G.R. et al., "Chondrogenic Potential of Adipose Tissue-Derived Stromal Cell In Vitro and In Vivo", Biochemical and Biophysical Research Communications 290:763-769 (2002).

Fischer L.J. et al., "Endothelial Differentiation of Adipose-Derived Stem Cells: Effects of Endothelial Cell Growth Supplement and Shear Force", Journal of Surgical Research 152(1):157-166 (Mar. 2009).

Frese L. et al., "Adipose Derived Tissue Engineered Heart Valve", J. Tissue Science & Engineering 6(3):1000156 (2015).

Frisch S.M. et al., "Disruption of Epithelial Cell-Matrix Interactions Induces Apoptosis", The Journal of Cell Biology 124(4):619-626 (Feb. 1994).

Gallina C. et al., "A New Paradigm in Cardiac Regeneration: The Mesenchymal Stem Cell Secretome", Stem Cells International 2015(765846) (10 pages) (2015).

Gaustad K.G. et al., "Differentiation of Human Adipose Tissue Stem Cells Using Extracts of Rat Cardiomyocytes", Biochemical and Biophysical Research Communications 314:420-427 (2004).

(56) References Cited

OTHER PUBLICATIONS

Gnecchi M. et al., "Paracrine Mechanisms in Adult Stem Cell Signaling and Therapy", Circ Res. 103:1204-1219 (2008).
Goren A. et al., "Encapsulated Human Mesenchymal Stem Cells: A Unique Hypoimmunogenic Platform for Long-Term Cellular Therapy", The FASEB Journal 24:22-31 (2010).
Hibino N. et al., "The Tissue-Engineered Vascular Graft Using Bone Marrow Without Culture", The Journal of Thoracic and Cardiovascular Surgery 129:1064-1070 (2005).
Hill K.L. et al., "Human Embryonic Stem Cell-Derived Vascular Progenitor Cells Capable of Endothelial and Smooth Muscle Cell Function", Experimental Hematology 38:246-257 (2010).
Hofmann M. et al., "Monitoring of Bone Marrow Cell Homing into the Infarcted Human Myocardium", Circulation 111:2198-2202 (2005).
Kavalkovich K.W. et al., "Chondrogenic Differentiation of Human Mesenchymal Stem Cells Within an Alginate Layer Culture System", In Vitro Cell Dev Biol. 38:457-466 (Sep. 2002).
Lidong G. et al., "In Vitro Differentiation of Human Adipose-Derived Mesenchymal Stem Cells into Endothelial-Like Cells", Chinese Science Bulletin 51(15):1863-1868 (2006).
Maumus M. et al., "Mesenchymal Stem Cells in Regenerative Medicine Applied to Rheumatic Diseases: Role of Secretome and Exosomes", Biochimie 95(12):2229-2234 (Dec. 2013).
Merfeld-Clauss S. et al., "Adipose Stromal Cell Contact With Endothelial Cells Results in Loss of Complementary Vasculogenic Activity Mediated by Induction of Activin A", Tissue-Specific Stem Cells 33:3039-3051 (2015).
Mizuno H. et al., "Myogenic Differentiation by Human Processed Lipoaspirate Cells", Plastic and Reconstructive Surgery 109(1):199-209 (Jan. 2002).
Ning H. et al., "Neuron-Like Differentiation of Adipose Tissue-Derived Stromal Cells and Vascular Smooth Muscle Cells", Differentiation 74:510-518 (2006).
Park I S et al., "Synergistic Effect of Biochemical Factors and Strain on the Smooth Muscle Cell Differentiation of Adipose-Derived Stem Cells on an Elastic Nanofibrous Scaffold", Journal of Biomaterials Science 23:1579-1593 (2012).
Perets A. et al., "Enhancing the Vascularization of Three-Dimensional Porous Alginate Scaffolds by Incorporating Controlled Release Basic Fibroblast Growth Factor Microspheres", J Biomed Mater Res 65A:489-497 (2003).
Perin E.C. et al., Effect of Transendocardial Delivery of Autologous Bone Marrow Mononuclear Cells on Functional Capacity, Left Ventricular Function, and Perfusion in Chronic Heart Failure, JAMA 307(16):1717-1726 (2012).
Planat-Benard V. et al., "Plasticity of Human Adipose Lineage Cells Toward Endothelial Cells", Circulation 109:656-663 (2004).
Prasad K. et al., "Intravenous Autologous Bone Marrow Mononuclear Stem Cell Therapy for Ischemic Stroke", Stroke 45(12):3618-3624 (2014.
Prichard H.L. et al., "IFATS Collection: Adipose-Derived Stromal Cells Improve the Foreign Body Response", Stem Cells 26:2691-2695 (2008).
Qu M-J et al., "Frequency-Dependent Phenotype Modulation of Vascular Smooth Muscle Cells Under Cyclic Mechanical Strain", Journal of Vascular Research 44:345-353 (2007).

Robinton D.A. et al., "The Promise of Induced Pluripotent Stem Cells in Research and Therapy", Nature 481:295-305 (Jan. 19, 2012).
Roh J.D. et al., "Tissue-Engineered Vascular Grafts Transform into Mature Blood Vessels via an Inflammation-Mediated Process of Vascular Remodeling", PNAS 107(10):4669-4674 (Mar. 9, 2010).
Rohringer S. et al., "Mechanisms of Vasculogenesis in 3D Fibrin Matrices Mediated by the Interaction of Adipose-Derived Stem Cells and Endothelial Cells", Angiogenesis 17:921-933 (2014).
Rytlewski J.A. et al., "Mechanisms of Tubulogenesis and Endothelial Phenotype Expression", Microvascular Research 99:26-35 (2015).
Safford K.M. et al., "Neurogenic Differentiation of Murine and Human Adipose-Derived Stromal Cells", Biochemical and Biophysical Research Communications 294:371-379 (2002).
Seo M J et al., "Differentiation of Human Adipose Stromal Cells into Hepatic Lineage In Vitro and In Vivo", Biochemical and Biophysical Research Communications 328:258-264 (2005.
Shevchenko E K et al., "Transplantation of Modified Human Adipose Derived Stromal Cells Expressing VEGF165 Results in More Efficient Angiogenic Response in Ischemic Skeletal Muscle", Journal of Translational Medicine 11(138):1-18 (2013).
Sivarapatna A. et al., "Arterial Specification of Endothelial Cells Derived from Human Induced Pluripotent Stem Cells in a Biomimetic Flow Bioreactor", Biomaterials 53:621-633 (2015).
Tobias C.A. et al., "Grafting of Encapsulated BDNF-Producing Fibroblasts into the Injured Spinal Cord Without Immune Suppression in Adult Rats", Journal of Neurotrauma 18(3):287-301 (2001).
Wang H. et al., "Shear Stress Induces Endothelial Transdifferentiation from Mouse Smooth Muscle Cells", Biochemical and Biophysical Research Communications 346:860-865 (2006).
Weissman I.L., "Stem Cells are Units of Natural Selection for Tissue Formation, for Germline Development, and in Cancer Development", PNAS 112(29):8922-8928 (Jul. 21, 2015).
Weissman I.L. et al., "Stem Cells: Units of Development, Units of Regeneration, and Units in Evolution", Cell 100:157-168 (Jan. 7, 2000).
Xu J. et al., "Chondrogenic Differentiation of Human Mesenchymal Stem Cells in Three-Dimensional Alginate Gels", Tissue Engineering: Part A 14(5):667-680 (2008).
Ye C. et al., "Shear Stress and Vascular Smooth Muscle Cells Promote Endothelial Differentiation of Endothelial Progenitor Cells Via Activation of Akt", Clinical Biomechanics 23:S118-S124 (2008).
Zeng L. et al., "Bioenergetic and Functional Consequences of Bone Marrow-Derived Multipotent Progenitor Cell Transplantation in Hearts With Postinfarction Left Ventricular Remodeling", Circulation 115:1866-1875 (2007).
Zhang R. et al., "Nuclear Fusion-Independent Smooth Muscle Differentiation of Human Adipose-Derived Stem Cells Induced by a Smooth Muscle Environment", Stem Cells 30:481-490 (2012).
Zheng Y. et al., "Generation of a Human Urinary Bladder Smooth Muscle Cell Line", In Vitro Cell Dev Biol 48:84-96 (2012).
Zvibel I. et al., "Anoikis: Roadblock to Cell Transplantation?", Cell Transplantation 11:621-630 (2002).
Zuk P.A. et al., "Human Adipose Tissue is a Source of Multipotent Stem Cells", Molecular Biology of the Cell 13:4279-4295 (Dec. 2002).

\* cited by examiner

Round annulus          Sector of an annulus

ARTIFICIAL TISSUE PROGENITOR AND METHOD FOR PREPARING THE SAME

TECHNICAL FIELD

The present invention relates to the tissue engineering field and to the 3D printing field. In particular, the invention relates to an artificial tissue progenitor comprising a solid support and a plurality of microcapsules, wherein at least one microcapsule is attached to the solid support and the microcapsule comprises a cell and a biocompatible material encapsulating the cell, to a method for preparing the artificial tissue progenitor, to a kit and a package useful for preparing the artificial tissue progenitor, to an artificial tissue obtained by culturing the artificial tissue progenitor, such as an artificial lumen, to a lumen implant or lumen model containing the artificial tissue progenitor or the artificial lumen, to use of the artificial tissue progenitor in the manufacture of an artificial tissue, a lumen implant or a lumen model, and to use of the artificial tissue in the manufacture of a lumen implant or lumen model.

BACKGROUND ART

Vascular grafting and vascular repair with a vascular patch can be used to replace, reconstruct, or repair stenosed, occluded, dilated, damaged, or deformed blood vessels. Typical vascular grafts or vascular patches are from autologous arteries or veins of a patient. However, artificial blood vessels (patches) or allogeneic blood vessels (patches) need to be used as substitutes in the case where the patient's autologous vessels are not sufficiently supplied (e.g., the patient suffers from a vascular disease or has previously been subjected to a transplantation of blood vessel).

The development of artificial blood vessels began in the early 20$^{th}$ century, and materials for making artificial blood vessels include metal, glass, polyethylene, silicone rubber and so on. It has been found from a large number of animal experiments that artificial blood vessels made of these materials will result in thrombus formation in lumens in a short period, and therefore cannot be clinically applied.

In 1952, Voorhees applied an artificial blood vessel made of vinylon in animal experiments successfully (see, Voorhees A B Jr, Jaretzki A 3rd, Blakemore A H. The use of tubes constructed from Vinyon "N" cloth in bridging arterial defects. J. Annals of Surgery, 1952, 135(3):332-336). In the 1950s to 1970s, artificial blood vessels with meshes in the wall appeared in succession, and materials used included polyester, silk, expanded polytetrafluoroethylene, and the like. However, the problems associated with vascular restenosis or blockage caused by thrombosis and neointimal thickening cannot be solved only by means of the improvement of materials. The researchers further attempted to optimize materials of artificial blood vessels, for example, addition of a material coating (e.g., carbon coating, nanoparticle coating, and protein coating etc.) to the internal surface of an artificial blood vessel since 1980, use of a composite material for the preparation of an artificial blood vessel since 1982; modification of a material of the internal surface of an artificial blood vessel since 1984, including addition of an anticoagulant (e.g., heparin or urokinase etc.) to material, sulfonation or plasma treatment of a material of inner wall; research and development of new biocompatible anticoagulant materials since 1992, such as polyurethane; use of natural biomaterials since 1998, such as stents of cell-free vascular matrix material. These methods do improve the performances of artificial blood vessels to a certain extent. However, these artificial blood vessels will still result in thrombus and restenosis after they are implanted into bodies, failing to achieve the same function as normal blood vessels. These phenomena have been reported in related literatures, for example, MacLeod D C, Strauss B H, de Jong M, Escaned J, Umans V A, van Suylen R J, Verkerk A, de Feyter P J, Serruys P W, "Proliferation and extracellular matrix synthesis of smooth muscle cells cultured from human coronary atherosclerotic and restenotic lesions", J. Am. Coll. Cardiol. 1994, 23(1): 59-65; and Baumgartner I, Schainfeld R, Graziani, "Management of Peripheral Vascular Disease", Annual Review of Medicine, 2005, 56(1): 249-272.

The reason why a normal blood vessel does not result in thrombus is that there is a layer of endothelial cells in the inner wall of its lumen. Therefore, in order to allow an artificial blood vessel to achieve same functions as a normal blood vessel, the most fundamental solution is to endothelialize the artificial blood vessel, that is, an intact layer of endothelial cells is formed on the inner wall of the artificial blood vessel.

In 1978, it was firstly reported by Herring et al. on experimental study on endothelialization of artificial blood vessels by seeding autologous endothelial cells (see, Herring M, Gardner A, Glover J. "A single-staged technique for seeding vascular grafts with autogenous endothelium", Surgery. 1978, 84(4): 498-504). In the technique, autogenous endothelial cells were cultured and amplified in vitro, and directly seeded onto the surface of inner wall of an artificial blood vessel, hoping that these endothelial cells can form an intact layer of endothelial cells after in vitro cultured for a short period of time and seeded. This research has opened a door to research clinical seeding of endothelial cells. However, endothelial cells grow slowly during the in vitro culture, it is difficult to obtain a sufficient number of cells, and the cells rapidly age after 5-8 passages, directly affecting function of cells after seeded. A large number of in vitro and in vivo experiments prove that: by using such a method of directly seeding endothelial cells in the inner wall of artificial blood vessels, the cells have weak impact resistance to blood flow and are easy to fall off, and thus a layer of endothelial cells cannot be formed; and there is no significant difference in anti-thrombosis, as compared with artificial blood vessels without being seeded with endothelial cells (see, Herring M, Smith J, Dalsing M, Glover J, Compton R, Etchberger K, Zollinger T., "Endothelial seeding of polytetrafluoroethylene femoral popliteal bypasses: the failure of low-density seeding to improve patency", J. Vasc. Surg, 1994; 20(4): 650-655; and Jensen N, Lindblad B, Bergqvist D., "Endothelial cell seeded dacron aortobifurcated grafts: platelet deposition and long-term follow-up", J. Cardiovasc. Surg. (Torino), 1994; 35(5): 425-429).

In 1986, researchers began to study tissue engineered blood vessels, and then constructed artificial blood vessels using stem cells as seed cells. The main sources of stem cells include embryonic stem cells, hematopoietic stem cells, mesenchymal stem cells and induced pluripotent stem cells (IPS). A method of constructing artificial blood vessels using stem cells as seed cells comprises: preparing a material of vascular stent, in vitro inducing the stem cells into vascular cells (including endothelial cells, smooth muscle cells and fibroblasts), seeding the vascular cells into the material of the stent, and performing in vivo implantation; alternatively, directly seeding the stem cells into the material of the vascular stent. The latter method comprises the following procedures: preparing a vascular stent, adding dropwise a cell suspension of cultured seed cells on the surface of the vascular stent, in vitro culturing to adhere the cells to the surface of the stent, and implanting the stent in bodies. The cells need to undergo a migration process so as to enter inside the stent. Accordingly, as far as the artificial blood vessels prepared by the two methods are concerned, in general, there is a large amount of cells aggregated on the surface of the stent, and there is only a small amount of cells inside the stent, or the cells are not evenly distributed, and thus the prepared artificial blood vessels can hardly form a complete structure and function. If a variety of cells is seeded in the stent, the phenomenon of randomly distributed cells will appear. Therefore, vascular cells arrange randomly inside the artificial blood vessels prepared by the two methods, it is difficult to form an intact layer of endothelial cells and a structured layer of smooth muscle cells, and the artificial blood vessels still cannot be clinically applied.

BRIEF SUMMARY OF THE INVENTION

In order to solve the above technical problem, the inventors of the present application have developed a new method for preparing an artificial tissue progenitor. In some preferred embodiments, the artificial tissue progenitor is an artificial lumen progenitor that can form an artificial lumen (e.g., an artificial blood vessel).

In one aspect, the present invention relates to an artificial tissue progenitor comprising a solid support and a plurality of microcapsules, wherein at least one microcapsule is attached to the solid support, and the microcapsule comprises a cell and a biocompatible material encapsulating the cell.

In some preferred embodiments, the artificial tissue progenitor is a lumen (e.g., a circulatory lumen, a digestive lumen, a respiratory lumen, a urinary lumen, or a genital lumen) progenitor.

In some preferred embodiments, the lumen is a lumen containing a epithelial cell (e.g., blood vessel, esophagus, trachea, stomach, bile duct, gut (including small intestine and large intestine, such as duodenum, jejunum, ileum, cecum (including appendix), ascending colon, right colic flexure, transverse colon, left colic flexure, descending colon, sigmoid colon, rectum), fallopian tube, vas deferens, ureter, bladder or lymphatic vessel).

In some preferred embodiments, the artificial tissue progenitor is tubular or sheet-like.

In some preferred embodiments, the plurality of the microcapsules constitutes one or more biological constructs.

In some preferred embodiments, the one or more biological constructs is attached to the solid support.

In one aspect, the present invention relates to a method of preparing said artificial tissue progenitor that is in a form of tube, comprising the following steps:

(I) preparing a tubular (e.g., in a shape of a round tube; e.g., in a shape of a tube with or without an opening at side wall) biological construct; and (II) attaching the tubular biological construct to the inner wall of a tubular solid support.

In some preferred embodiments, the tubular biological construct is prepared by a method comprising the following steps:

(1) providing one or more microcapsules having a first component attached to all or a part of the surface thereof; preferably, the first component being contained in a first agent;

(2) coating a second agent containing a second component on a predetermined area of the surface of a temporary support, wherein a sticky effect can be produced to achieve an adhesion effect when the first component and the second component are in contact with each other; the temporary support is tubular or cylindrical (for example, a round tube without an opening at side wall, a round tube with an opening at side wall, a cylinder or a column arranged along a part of a circumference) support, the predetermined area is located on the curved surface of the temporary support; optionally, coating a substrate material onto the predetermined area of the surface of the temporary support prior to coating the second agent;

(3) placing the microcapsules having the first component attached to all or a part of the surface thereof in step (1) on the predetermined area coated with the second agent, so that the first component on the surface of the microcapsules is in contact with the second component on the predetermined area to produce a sticky effect, thereby assembling (adhering) the microcapsules into a first layer structure, wherein the first layer structure is a tubular structure;

optionally, the method further comprises the following steps:

(4) coating the second agent onto the structure formed in the previous step;

(5) placing the microcapsules having the first component attached to all or a part of the surface thereof in step (1) on the structure produced in the previous step, so that the first component on the surface of the microcapsules is in contact with the second component on the structure produced in the previous step to produce a sticky effect, thereby assembling (adhering) the microcapsules into another layer structure on the structure produced in the previous step; and (6) optionally, repeating the steps (4) and (5) for one or more times;

thereby obtaining the tubular biological construct.

In one aspect, the present invention relates to another method of preparing said artificial tissue progenitor that is in a form of tube, comprising the following steps:

(I) preparing a tubular (e.g., in a shape of a round tube; e.g., in a shape of a tube with or without an opening at side wall) biological construct; and (II) attaching the tubular biological construct to the inner wall of a tubular solid support.

In some preferred embodiments, the tubular biological construct is prepared by a method comprising the following steps:

(1) providing one or more microcapsules having a first component attached to all or a part of the surface thereof; preferably, the first component is contained in a first agent;

(2) drawing a predetermined annular (e.g., a round annulus or a sector of an annulus) pattern on the surface of a temporary support with a second agent containing a second component, wherein a sticky effect can be produced to achieve an adhesion effect when the first component and the second component are in contact with each other; the temporary support has at least one plane, and the annular pattern is located on the plane of the temporary support;

(3) placing the microcapsules having the first component attached to all or a part of the surface thereof in step (1) on the predetermined annular pattern drawn with the second agent, so that the first component on the surface of the microcapsules is in contact with the second component on the annular pattern to produce a sticky effect, thereby assembling (adhering) the microcapsules into a first layer structure, wherein the first layer structure is an annular structure;

(4) coating the second agent onto the annular structure;

(5) placing the microcapsules having the first component attached to all or a part of the surface thereof in step (1) on the structure produced in the previous step, so that the first component on the surface of the microcapsules is in contact with the second component on the structure produced in the previous step to produce a sticky effect, thereby assembling (adhering) the microcapsules into another layer structure on the structure produced in the previous step; and (6) optionally, repeating the steps (4) and (5) for one or more times;

thereby obtaining the tubular biological construct.

In one aspect, the present invention relates to a method of preparing said artificial tissue progenitor that is in a form of sheet, comprising the following steps:

(I) preparing a sheet-like (e.g., in a shape of a planar sheet, or in a shape of a curved sheet) biological construct; and (II) attaching the sheet-like biological construct to a sheet-like solid support.

In some preferred embodiments, the sheet-like biological construct is prepared by a method comprising the following steps:

(1) providing one or more microcapsules having a first component attached to all or a part of the surface thereof; preferably, the first component is contained in a first agent;

(2) coating a second agent containing a second component on a predetermined area of the surface of a temporary support, wherein a sticky effect can be produced to achieve an adhesion effect when the first component and the second component are in contact with each other; the temporary support has at least one plane, and the predetermined area is located on the plane of the temporary support;

(3) placing the microcapsules having the first component attached to all or a part of the surface thereof in step (1) on the predetermined area coated with the second agent, so that the first component on the surface of the microcapsules is in contact with the second component on the predetermined area to produce a sticky effect, thereby assembling (adhering) the microcapsules into a first layer structure, wherein the first layer structure is a sheet-like structure;

optionally, the method further comprises the following steps:

(4) coating the second agent onto the structure formed in the previous step;

(5) placing the microcapsules having the first component attached to all or a part of the surface thereof in step (1) on the structure produced in the previous step, so that the first component on the surface of the microcapsules is in contact with the second component on the structure produced in the previous step to produce a sticky effect, thereby assembling (adhering) the microcapsules into another layer structure on the structure produced in the previous step; and (6) optionally, repeating the steps (4) and (5) for one or more times, thereby obtaining the planer, sheet-like biological construct;

optionally, the method further comprises bending the planar, sheet-like biological construct to give a curved, sheet-like biological construct.

In one aspect, the present invention relates to another method of preparing said artificial tissue progenitor that is in a form of sheet, comprising the following steps:

(I) preparing a sheet-like biological construct according to the method for preparing a sheet-like biological construct above; and (II) providing a material (e.g., a biocompatible material) for preparing a solid support, and preparing a sheet-like solid support on the sheet-like biological construct.

In some preferred embodiments, the sheet-like solid support is prepared by a 3D-printing or a spraying process.

In one aspect, the present invention relates to another method of preparing said artificial tissue progenitor that is in a form of tube, comprising the following steps:

(I) preparing a sheet-like biological construct according to the method for preparing a sheet-like biological construct above;

(II) bending the sheet-like biological construct prepared in the step (I), and/or adhering the edges of the sheet-like biological construct to obtain a tubular biological construct; and (III) attaching the tubular biological construct to the inner wall of a tubular solid support.

In one aspect, the present invention relates to another method of preparing said artificial tissue progenitor that is in a form of tube, comprising the following steps:

(I) preparing a tubular biological construct according to a method for preparing a tubular biological construct as defined in any one of the above items;

or preparing a sheet-like biological construct according to the method for preparing a sheet-like biological construct as above defined; then, bending the sheet-like biological construct, and/or adhering the edges of the sheet-like biological construct to obtain a tubular biological construct; and (II) providing a material (e.g., a biocompatible material) for preparing a solid support, and preparing a tubular solid support on the outer wall of the tubular biological construct.

In some preferred embodiments, the tubular solid support is prepared by a 3D-printing or a spraying process.

In one aspect, the present invention relates to a method of preparing said artificial tissue progenitor, comprising the following steps:

(1) providing one or more microcapsules having a first component attached to all or a part of the surface thereof; preferably, the first component is contained in a first agent;

(2) providing a solid support, and coating a second agent containing a second component on a predetermined area of the surface of the solid support, wherein a sticky effect can be produced to achieve an adhesion effect when the first component and the second component are in contact with each other;

(3) placing the microcapsules having the first component attached to all or a part of the surface thereof in step (1) on the predetermined area coated with the second agent, so that the first component on the surface of the microcapsules is in contact with the second component on the predetermined area to produce a sticky effect, thereby assembling (adhering) the microcapsules into a first layer structure on the surface of the solid support;

optionally, the method further comprises the following steps:

(4) coating the second agent onto the structure formed in the previous step;

(5) placing the microcapsules having the first component attached to all or a part of the surface thereof in step (1) on the structure produced in the previous step, so that the first component on the surface of the microcapsules is in contact with the second component on the structure produced in the previous step to produce a sticky effect, thereby assembling (adhering) the microcapsules into another layer structure on the structure produced in the previous step; and (6) optionally, repeating the steps (4) and (5) for one or more times;

thereby obtaining the artificial tissue progenitor.

In some preferred embodiments, the solid support is a tubular or sheet-like support.

In some preferred embodiments, the solid support is a tubular support, and the predetermined area is located in the inner wall of the solid support.

In the method for preparing an artificial tissue progenitor of the present invention, preferably, the first component and/or the second component is a biocompatible material, a bio-derived material, and/or a biodegradable material.

In some preferred embodiments, the sticky effect resulting from the contact of the first component with the second component can be used to adhere the two microcapsules together to form a biological construct; and the resulting biological construct thus obtained has a tensile modulus of not less than 10 Pa, for example, not less than 20 Pa, not less than 30 Pa, not less than 40 Pa, not less than 50 Pa, not less than 60 Pa, not less than 70 Pa, not less than 80 Pa, not less than 90 Pa, not less than 100 Pa, not less than 200 Pa, not less than 300 Pa, not less than 400 Pa, not less than 500 Pa, not less than 600 Pa, not Less than 700 Pa, not less than 800 Pa, not less than 900 Pa, or not less than 1000 Pa.

In some preferred embodiments, the combination of the first component and the second component is selected from:
(1) fibrinogen and thrombin;
(2) alginate (e.g., sodium alginate) or oxidized alginate (e.g., oxidized sodium alginate), and a substance containing $Ca^{2+}$, $Mg^{2+}$, $Ba^{2+}$, $Sr^{2+}$ or $Fe^{3+}$ (for example, a solution or semisolid (e.g., gel) containing $Ca^{2+}$, $Mg^{2+}$, $Ba^{2+}$, $Sr^{2+}$ or $Fe^{3+}$);
(3) maleimide group-containing molecule (e.g., polyethylene glycol containing a maleimide group (MAL-PEG)) and free thiol group-containing molecule (e.g., polyethylene glycol containing a free thiol group (PEG-SH));
(4) anion containing substance (e.g., a solution or semisolid (e.g., gel) containing an anion) and alpha-cyanoacrylate (e.g., methyl alpha-cyanoacrylate, ethyl alpha-cyanoacrylate, isobutyl alpha-cyanoacrylate, isohexyl alpha-cyanoacrylate, n-octyl alpha-cyanoacrylate);
(5) fibrinogen and alpha-cyanoacrylate (e.g., methyl alpha-cyanoacrylate, ethyl alpha-cyanoacrylate, isobutyl alpha-cyanoacrylate, isohexyl alpha-cyanoacrylate, n-octyl alpha-cyanoacrylate);
(6) serum albumin (e.g., bovine serum albumin) and glutaraldehyde;
(7) molecule containing a carbamate group (—NHCOO—) or containing an isocyanate group (—NCO) (e.g., polyethylene glycol containing a carbamate group or polyethylene glycol containing an isocyanate group) and molecule containing reactive hydrogen (e.g., carboxyl-containing polyethylene glycol);
(8) gelatin-resorcinol and glutaraldehyde;
(9) carbodiimide cross-linking gelatin and poly-L-glutamic acid (PLGA); and
(10) aminated gelatin and polysaccharide aldehyde.

In one aspect, the present invention relates to a biological construct obtained by a method for preparing a biological construct as defined in any one of the above items.

In one aspect, the present invention relates to a kit useful for preparing an artificial tissue progenitor, the kit comprising a microcapsule, and a first agent and a second agent separated from each other, wherein the microcapsule comprises a cell and a biocompatible material encapsulating the cell, the first agent comprises a first component, the second agent comprises a second component, and when the first component is in contact with the second component, a sticky effect can be produced to achieve adhesion effect.

In some preferred embodiments, the sticky effect resulting from the contact of the first component with the second component can be used to adhere the two microcapsules together to form a biological construct; and the resulting biological construct thus obtained has a tensile modulus of not less than 10 Pa (e.g., not less than 100 Pa).

In some preferred embodiments, the first component and/or the second component is a biocompatible material, a bio-derived material, and/or a biodegradable material.

In some preferred embodiments, the combination of the first component and the second component is selected from:
(1) fibrinogen and thrombin;
(2) alginate (e.g., sodium alginate) or oxidized alginate (e.g., oxidized sodium alginate), and a substance containing $Ca^{2+}$, $Mg^{2+}$, $Ba^{2+}$, $Sr^{2+}$ or $Fe^{3+}$ (for example, a solution or semisolid (e.g., gel) containing $Ca^{2+}$, $Mg^{2+}$, $Ba^{2+}$, $Sr^{2+}$ or $Fe^{3+}$);
(3) maleimide group-containing molecule (e.g., polyethylene glycol containing a maleimide group (MAL-PEG)) and free thiol group-containing molecule (e.g., polyethylene glycol containing a free thiol group (PEG-SH));
(4) anion containing substance (e.g., a solution or semisolid (e.g., gel) containing an anion) and alpha-cyanoacrylate (e.g., methyl alpha-cyanoacrylate, ethyl alpha-cyanoacrylate, isobutyl alpha-cyanoacrylate, isohexyl alpha-cyanoacrylate, n-octyl alpha-cyanoacrylate);
(5) fibrinogen and alpha-cyanoacrylate (e.g., methyl alpha-cyanoacrylate, ethyl alpha-cyanoacrylate, isobutyl alpha-cyanoacrylate, isohexyl alpha-cyanoacrylate, n-octyl alpha-cyanoacrylate);
(6) serum albumin (e.g., bovine serum albumin) and glutaraldehyde;
(7) molecule containing a carbamate group (—NHCOO—) or containing an isocyanate group (—NCO) (e.g., polyethylene glycol containing a carbamate group or polyethylene glycol containing an isocyanate group) and molecule containing reactive hydrogen (e.g., carboxyl-containing polyethylene glycol);
(8) gelatin-resorcinol and glutaraldehyde;
(9) carbodiimide cross-linking gelatin and poly-L-glutamic acid (PLGA); and
(10) aminated gelatin and polysaccharide aldehyde.

In one aspect, the present application relates to a package useful for preparing an artificial tissue progenitor, comprising one or more kits of the present invention.

In one aspect, the present application relates to an artificial tissue, which is obtained by culturing (for example, in vitro culturing or in vivo culturing) the artificial tissue progenitor of the present invention.

In some preferred embodiments, the artificial tissue is an artificial lumen.

In some preferred embodiments, the lumen is a lumen containing an epithelial cell (e.g., blood vessel, esophagus, trachea, stomach, bile duct, gut (including small intestine and large intestine, such as duodenum, jejunum, ileum, cecum (including appendix), ascending colon, right colic flexure, transverse colon, left colic flexure, descending colon, sigmoid colon, rectum), fallopian tube, vas deferens, ureter, bladder or lymphatic vessel).

In some preferred embodiments, the artificial lumen is a tubular artificial lumen or a sheet-like artificial lumen.

In some preferred embodiments, the artificial lumen is an artificial blood vessel or vascular patch.

In one aspect, the present application relates to a lumen implant, which comprises an artificial tissue progenitor (e.g., tubular artificial tissue progenitor or sheet-like artificial tissue progenitor) or an artificial lumen of the present invention.

In some preferred embodiments, the lumen implant comprises one or more of artificial tissue progenitors (e.g., tubular artificial tissue progenitors or sheet-like artificial tissue progenitors) of the present invention, or one or more artificial lumens (e.g., tubular artificial lumens or sheet-like artificial lumens) of the present invention.

In some preferred embodiments, the lumen implant is a linear tubular structure, or a branched tubular structure.

In some preferred embodiments, the lumen implant is in a form of an X-shaped tube, a Y-shaped tube or a T-shaped tube.

In some preferred embodiments, the lumen is a lumen containing an epithelial cell, e.g., blood vessel.

In some preferred embodiments, the lumen implant is a vascular implant comprising an artificial blood vessel or vascular patch of the present invention.

In one aspect, the present application relates to a lumen (e.g., blood vessel) model, which comprises an artificial lumen (e.g., artificial blood vessel) of the present invention.

In some preferred embodiments, the lumen model comprise one or more of artificial lumens (e.g., artificial blood vessels) of the present invention.

In one aspect, the present application relates to use of an artificial tissue progenitor of the present invention in the manufacture of an artificial tissue, a lumen implant or a lumen model.

In one aspect, the present application relates to use of an artificial tissue of the present invention in the manufacture of a lumen implant or a lumen model.

The embodiments of the present invention will be explained in detail below with reference to the drawings and the detailed description of the invention. However, it will be understood by a person skilled in the art that the following drawings and detailed description of the invention are only used to illustrate the present invention, and not for the purpose of limiting the scope of the present invention. The various objects and advantageous aspects of the present invention will become apparent to a person skilled in the art, according to the disclosures contained in the drawings and the detailed description of the invention.

Figure 2A:
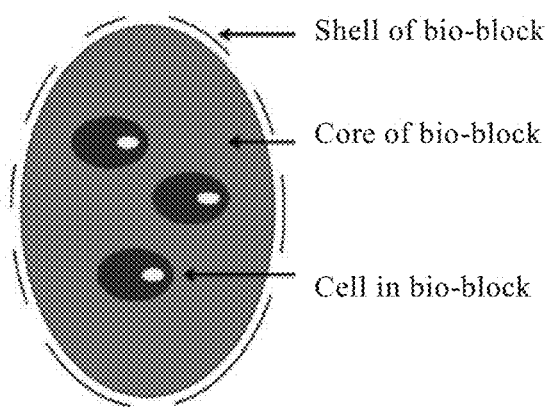
FIG. 2A to FIG. 2E schematically depict an exemplary structure of a bio-block of the present invention, which comprises a cell, a core encapsulating the cell, and a shell enclosing the core.

In particular, FIG. 2A schematically depicts a structure of a bio-block of the present invention, which comprises one core and one shell, wherein the core encapsulates cells, and the shell is located outside the core and encloses the core.

Figure 2B:
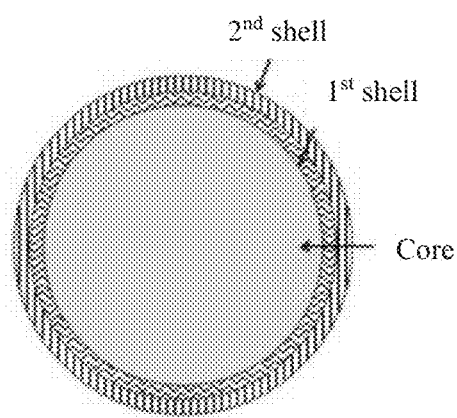

FIG. 2B schematically depicts a structure of a bio-block of the present invention, which comprises, in order from the inside to the outside, a core encapsulating cells, a first shell enclosing the core, and a second shell enclosing the first shell.

Figure 2C:
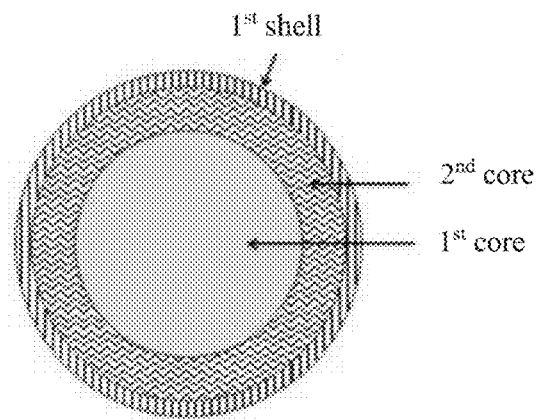

FIG. 2C schematically depicts a structure of a bio-block of the present invention, which comprises, in order from the inside to the outside, a first core encapsulating cells, a second core located outside the first core and encapsulating cells, and a first shell enclosing the first core and the second core.

Figure 2D:
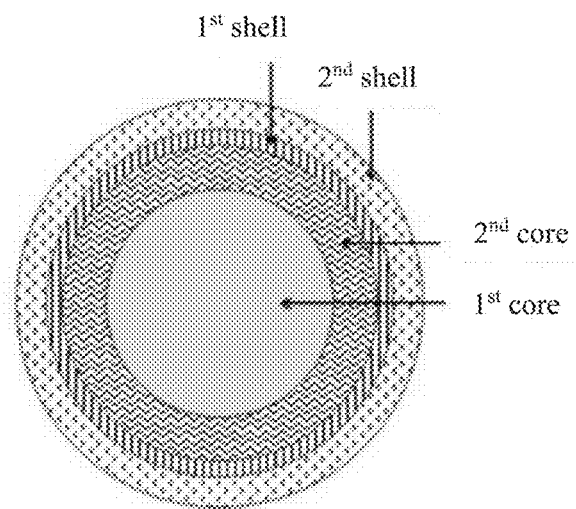

FIG. 2D schematically depicts a structure of a bio-block of the present invention, which comprises, in order from the inside to the outside, a first core encapsulating cells, a second core located outside the first core and encapsulating cells, a first shell enclosing the first core and the second core, and a second shell enclosing the first shell.

Figure 2E:
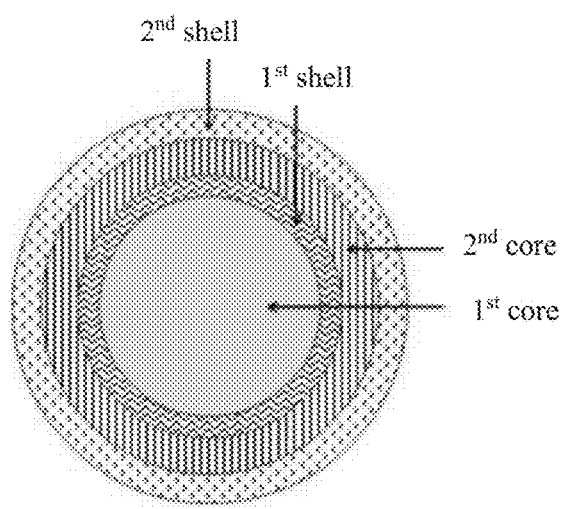

FIG. 2E schematically depicts a structure of a bio-block of the present invention, which comprises, in order from the inside to the outside, a first core encapsulating cells, a first shell enclosing the first core, a second core encapsulating cells, and a second shell enclosing the second core.

FIG. 3A to FIG. 3E exemplarily depict the structure of a tubular artificial tissue progenitor comprising a plurality of tubular biological constructs of the present invention.

Figures 3A, 3B, 3C, 3D, 3E:
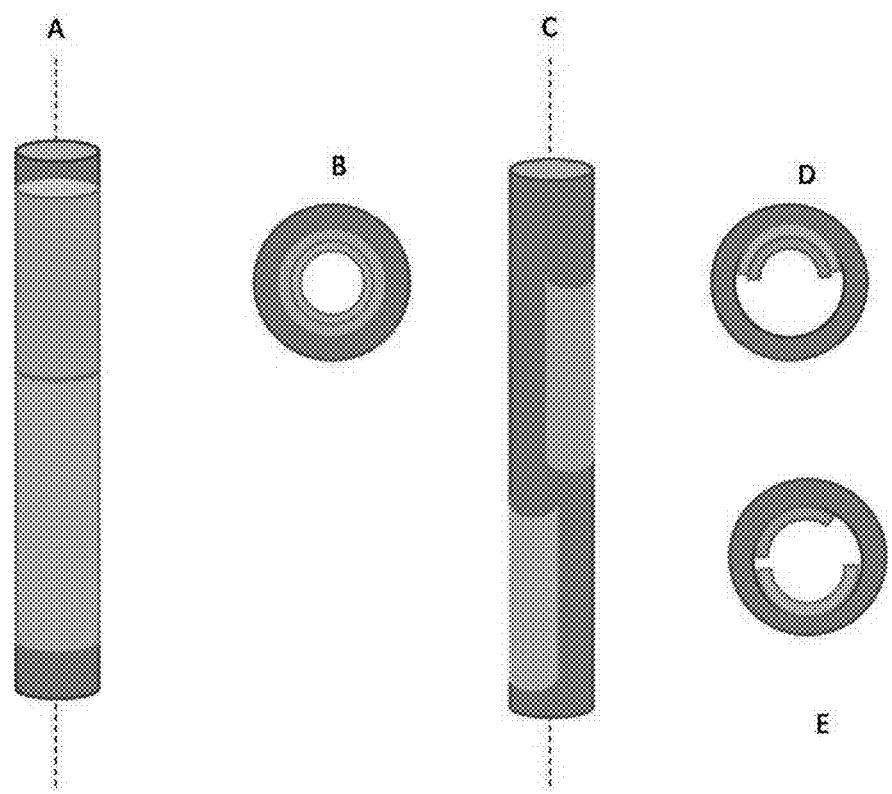

FIG. 3A is a side view of a tubular artificial tissue progenitor, wherein the artificial tissue progenitor comprises a tubular solid support and a plurality of tubular biological constructs which have no opening at side walls, wherein the tubular biological constructs are inside the tubular solid support and are aligned along the axial direction of the tubular solid support, and the outer wall of each tubular biological construct is attached to the inner wall of the tubular solid support.

FIG. 3B is a top view of a tubular artificial tissue progenitor, wherein the artificial tissue progenitor comprises a tubular solid support and a plurality of tubular biological constructs which have no opening at side walls, wherein the tubular biological constructs are inside the tubular solid support and are coaxially disposed with the tubular solid support, and the outer wall of the outermost tubular biological construct is attached to the inner wall of the tubular solid support.

FIG. 3C is a side view of a tubular artificial tissue progenitor, wherein the artificial tissue progenitor comprises a tubular solid support and a plurality of tubular biological constructs, wherein each tubular biological construct has an opening at side wall, wherein the tubular biological constructs are inside the tubular solid support and are aligned along the axial direction of the tubular solid support, and the outer wall of each tubular biological construct is attached to the inner wall of the tubular solid support.

FIG. 3D is a top view of a tubular artificial tissue progenitor, wherein the artificial tissue progenitor comprises a tubular solid support and a plurality of tubular biological constructs, wherein each tubular biological construct has an opening at side wall, wherein the tubular biological constructs are inside the tubular solid support and are coaxially disposed with the tubular solid support and radially aligned, and the outer wall of the outermost tubular biological construct is attached to the inner wall of the tubular solid support.

FIG. 3E is a top view of a tubular artificial tissue progenitor, wherein the artificial tissue progenitor comprises a tubular solid support and a plurality of tubular biological constructs, wherein each tubular biological construct has an opening at side wall, wherein the tubular biological constructs are inside the tubular solid support and are coaxially disposed with the tubular solid support, and the outer wall of each tubular biological construct is attached to the inner wall of the tubular solid support.

FIG. 4A to FIG. 4E exemplarily depict, in the method for preparing a tubular biological construct of the present invention, a pillar as a temporary support, unfolded side surfaces and predetermined areas on the unfolded side surfaces of the pillar.

Figures 4A, 4B, 4C, 4D, 4E:
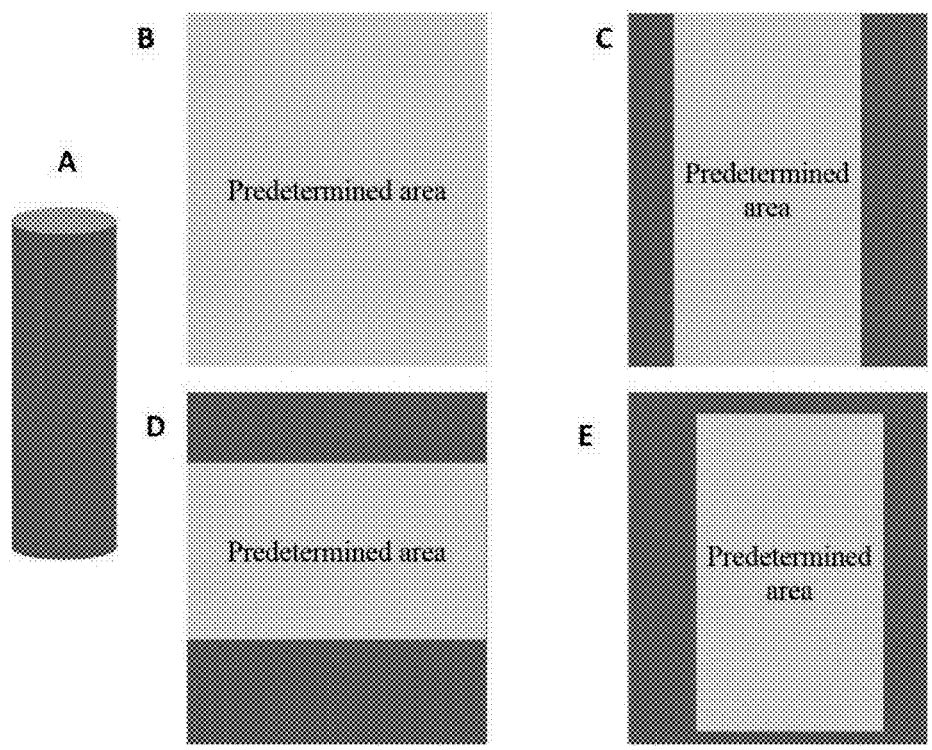

FIG. 4A exemplarily depicts, in the method for preparing a tubular biological construct of the present invention, a cylinder as a temporary support.

FIG. 4B exemplarily depicts the unfolded side surface of the cylinder in FIG. 4A and a predetermined area on the unfolded side surface, wherein the predetermined area is the entire side surface of the cylinder.

FIG. 4C exemplarily depicts the unfolded side surface of the cylinder in FIG. 4A and a predetermined area on the unfolded side surface, wherein the predetermined area is a rectangle on the unfolded side surface of cylinder, and the predetermined area goes through the side surface of the cylinder in the axial direction of the cylinder.

FIG. 4D exemplarily depicts the unfolded side surface of the cylinder in FIG. 4A and a predetermined area on the unfolded side surface, wherein the predetermined area is a rectangle on the unfolded side surface of cylinder, and the predetermined area goes through the side surface of the cylinder in the circumferential direction of the cylinder.

FIG. 4E exemplarily depicts the unfolded side surface of the cylinder in FIG. 4A and a predetermined area on the unfolded side surface, wherein the predetermined area is a rectangle on the unfolded side surface of cylinder, and the predetermined area does not go through the side surface of the cylinder in the axial or circumferential direction of the cylinder.

Figure 5A:
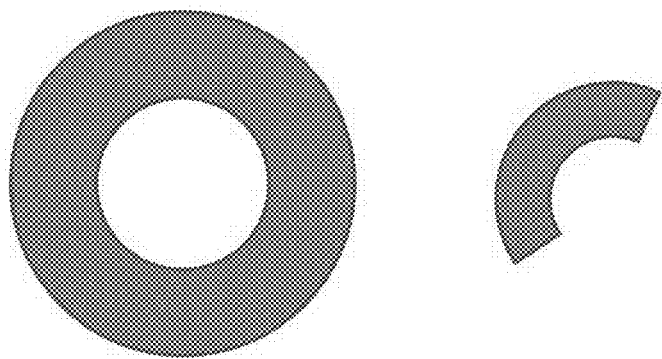

FIG. 5A exemplarily depicts patterns in shapes of a round annulus and a sector of an annulus, as predetermined areas, in the method 2 for preparing an artificial tissue progenitor of the present invention.

Figure 5B:
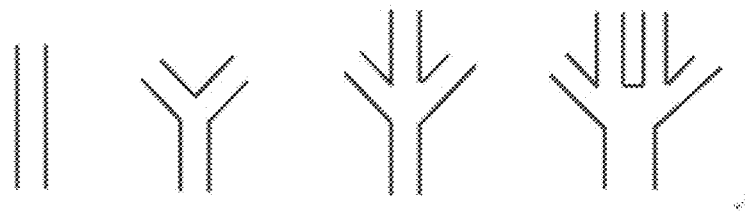

FIG. 5B exemplarily shows the shape of a lumen implant or lumen model of the present invention.

Figure 6:
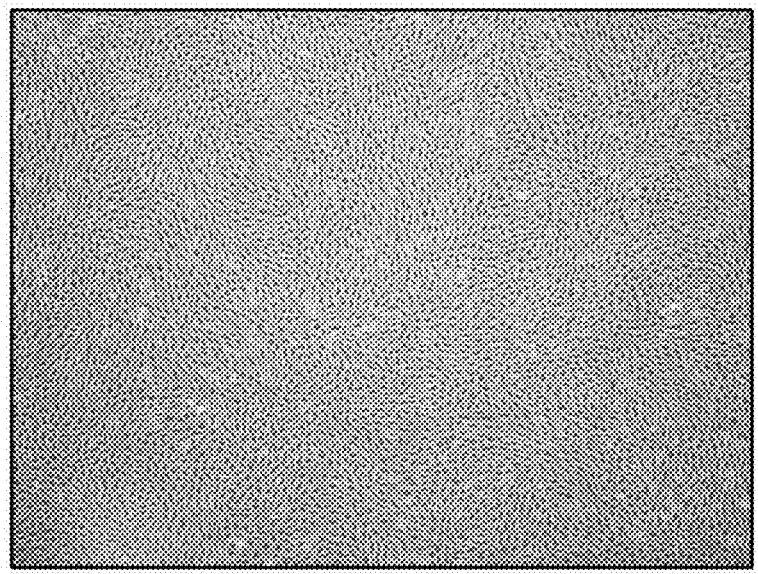

FIG. 6 is a photomicrograph of the fourth generation adipose-derived mesenchymal stem cells obtained by means of primary culture in Example 1; as can be seen from the figure, the morphology of the cells is uniform and the growth state of cells is good.

Figure 7:
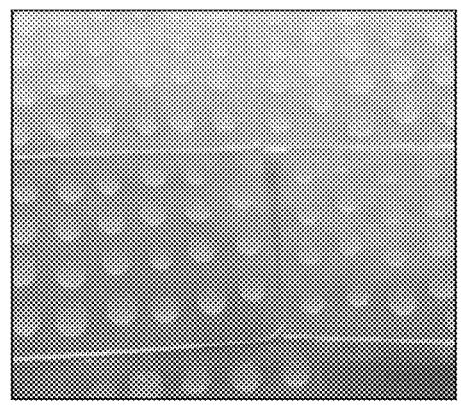

FIG. 7 shows the morphology of a bio-block containing Rhesus adipose-derived mesenchymal stem cells in Example 1.

Figure 8:
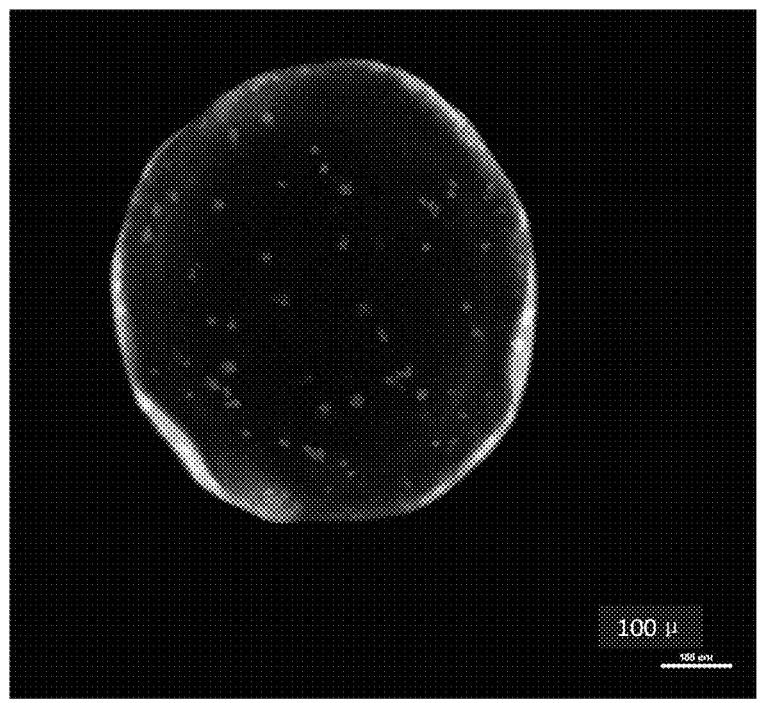

FIG. 8 is a photograph of a bio-block containing Rhesus adipose-derived mesenchymal stem cells taken by a laser confocal microscopy in Example 1, wherein the green fluorescence represents the shell and the red fluorescence represents the adipose-derived mesenchymal stem cells.

Figure 9:
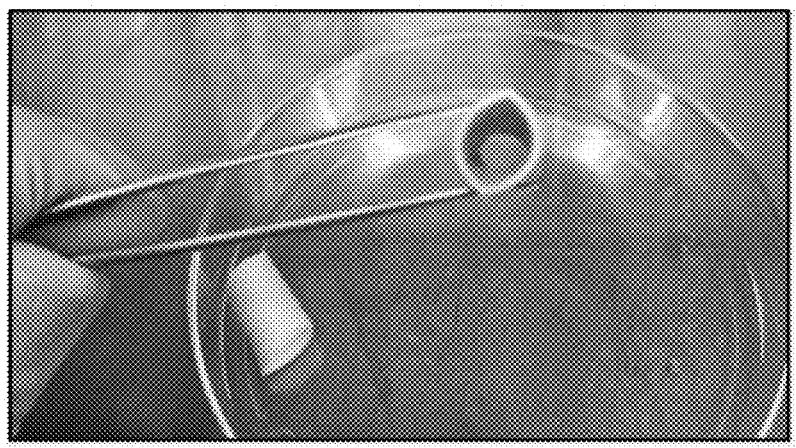

FIG. 9 is a photograph of an artificial blood vessel progenitor obtained in Example 2.

Figures 10A, 10B, 10C:
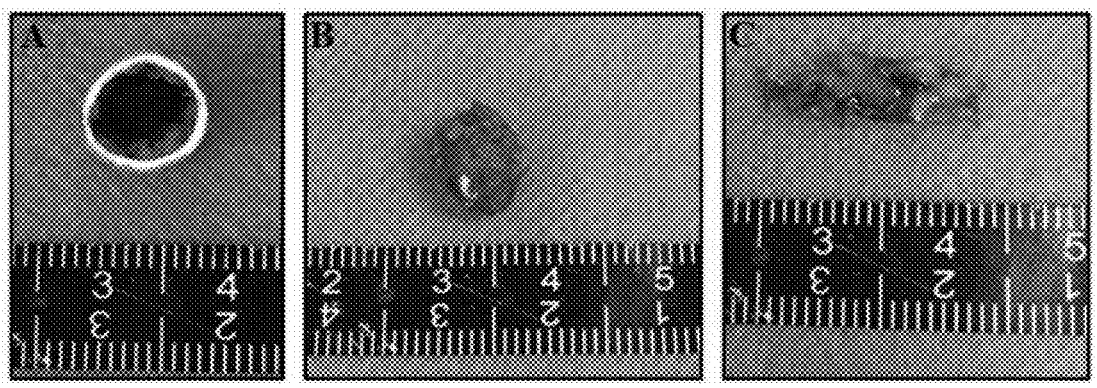

FIG. 10A to FIG. 10C show the artificial blood vessel obtained after 5 days of implantation of the artificial blood vessel progenitor prepared in Example 2 into a Rhesus monkey. FIG. 10A shows the whole morphology of the artificial blood vessel. FIG. 10B shows the tissue obtained by removing the tubular support, and FIG. 10C shows the morphology of the tissue obtained by longitudinal cutting. As can be seen from the figure, an endothelial tissue has formed on the surface of the tubular support.

Figures 11A, 11B:
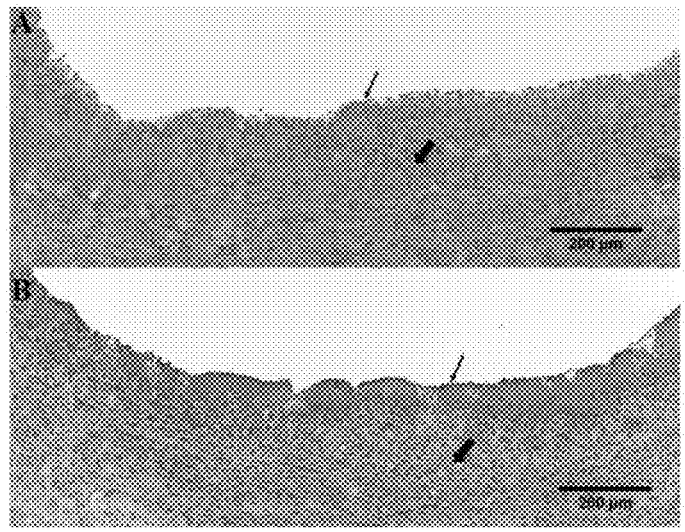

FIG. 11A to FIG. 11B show the result of HE staining of an artificial vascular tissue in Example 2, FIG. 11A involves in a normal blood vessel, and FIG. 11B involves in an artificial blood vessel. As shown in the figures, the artificial blood vessel and the normal blood vessel have a similar arrangement of cells, a similar layer of endothelial cells (as indicated by the thin arrow) and a similar layer of smooth muscle cells (as indicated by the thick arrow).

Figures 12A, 12B:
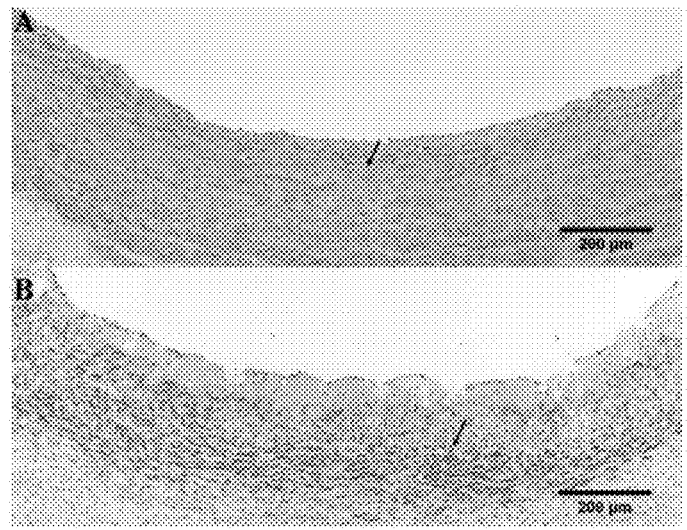

FIG. 12A to FIG. 12B show the result of α-SMA staining of an artificial vascular tissue in Example 2, wherein α-SMA-positive cells are smooth muscle cells. FIG. 12A involves in a normal blood vessel, and FIG. 12B involves in an artificial blood vessel. As shown in the figures, some adipose-derived mesenchymal stem cells of the artificial blood vessel differentiate into smooth muscle cells, and show similar cell morphology, alignment and directionality to a normal blood vessel.

Figures 13A, 13B:
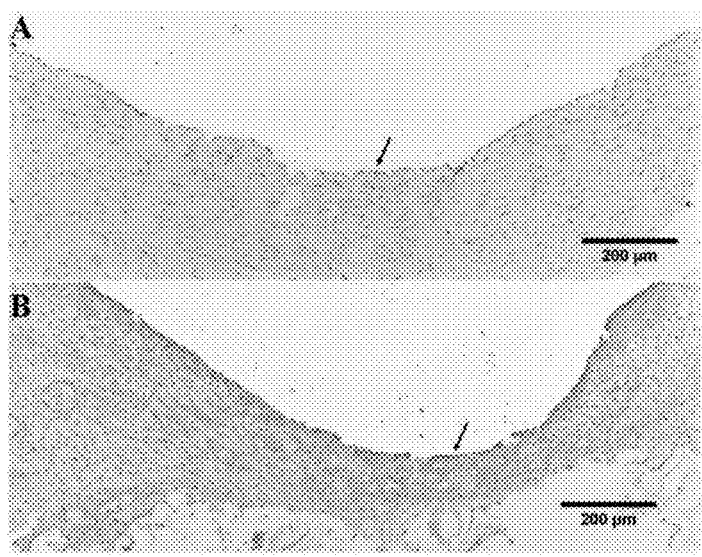

FIG. 13A to FIG. 13B show the result of CD31 staining of an artificial vascular tissue in Example 2, wherein CD31-positive cells are endothelial cells. FIG. 13A involves in a normal blood vessel, and FIG. 13B involves an artificial blood vessel. As shown in the figures, on the side that is in contact with blood, some adipose-derived mesenchymal stem cells of the artificial blood vessel differentiate into endothelial cells, and show similar cell morphology and alignment to a normal blood vessel.

Figures 14A, 14B:
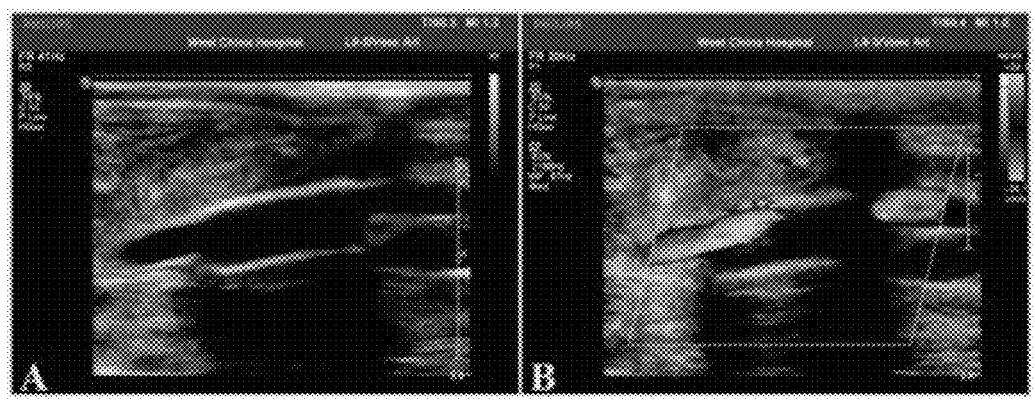

FIG. 14A to FIG. 14B show the morphology and blood flow direction of an artificial blood vessel in Example 3. FIG. 14A shows the results of ultrasonography, and it can be seen from the figure that the lumen of the artificial blood vessel is unobstructed. FIG. 14B shows the results of color Doppler imaging, and the results show that blood flow on both sides of the artificial blood vessel is in the same direction, providing that the blood vessel is unobstructed.

Figures 15A, 15B, 15C:
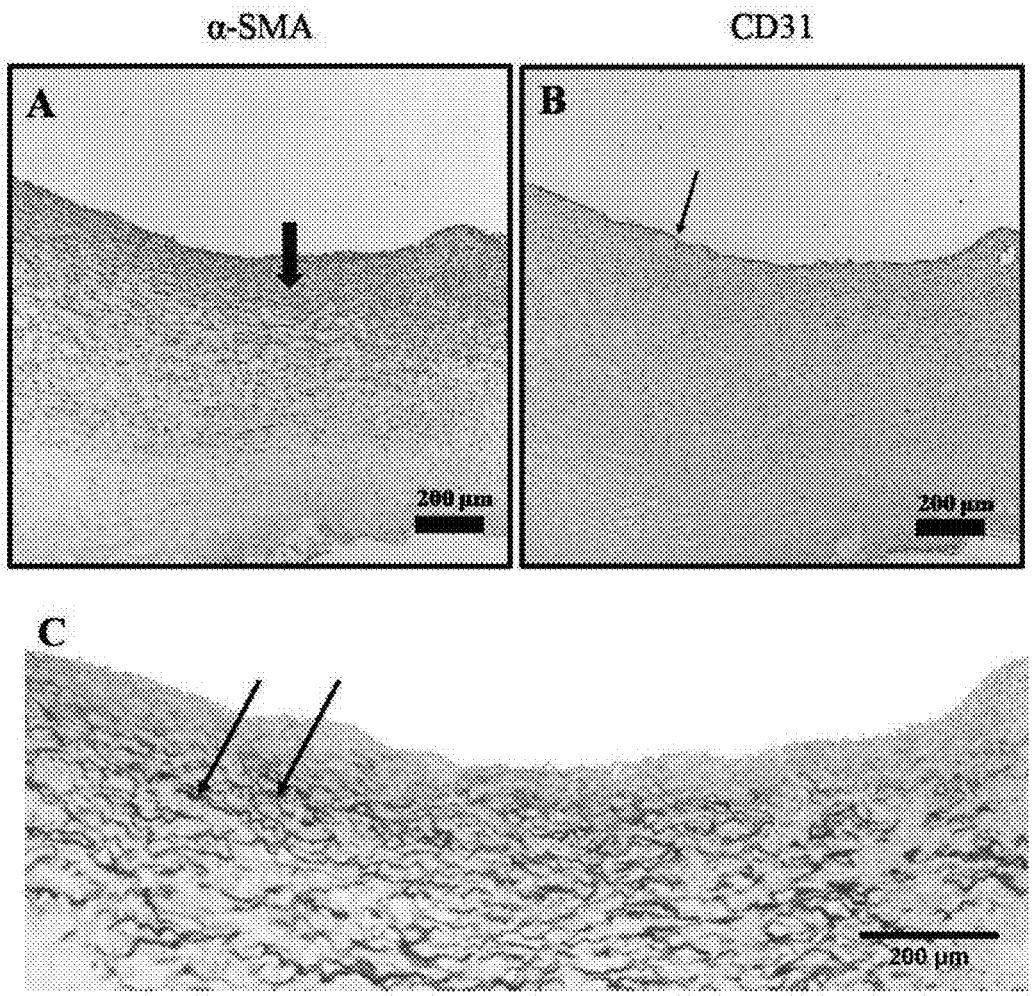

FIG. 15A to FIG. 15C show the result of immunohistochemical staining of an artificial blood vessel in Example 3. FIG. 15A shows the α-SMA staining results. As indicated by the thick arrow in the figure, some adipose-derived mesenchymal stem cells differentiate into smooth muscle cells in the artificial blood vessel. FIG. 15B shows the CD31 staining results. As indicated by the thin arrow in the figure, some adipose-derived mesenchymal stem cells differentiate into endothelial cells in the artificial blood vessel. FIG. 15C shows the Sirius red staining results. As shown in the figure, the artificial blood vessel forms a collagen structure similar to that of a normal blood vessel.

Figures 16A, 16B:
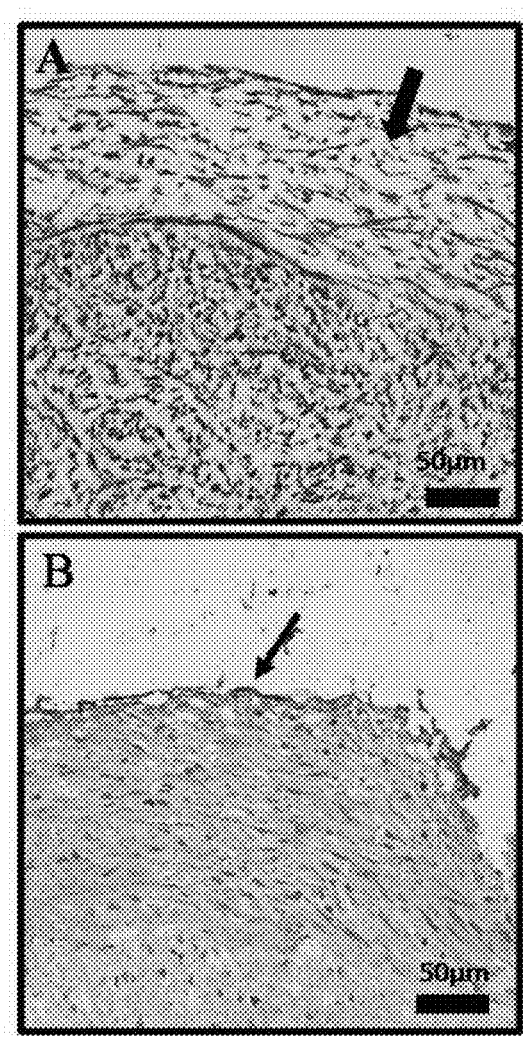

FIG. 16A and FIG. 16B show the immunohistochemical staining results of a sample taken out after 14 days of implantation of an artificial blood vessel progenitor into a Rhesus monkey in Example 4.

FIG. 16A shows the result of α-SMA staining. As indicated by the thick arrow in the figure, some adipose-derived mesenchymal stem cells differentiate into smooth muscle cells in the artificial blood vessel.

FIG. 16B shows the result of CD31 staining. As indicated by the thin arrow in the figure, some adipose-derived mesenchymal stem cells differentiate into endothelial cells in the artificial blood vessel.

Figures 17A, 17B, 17C:
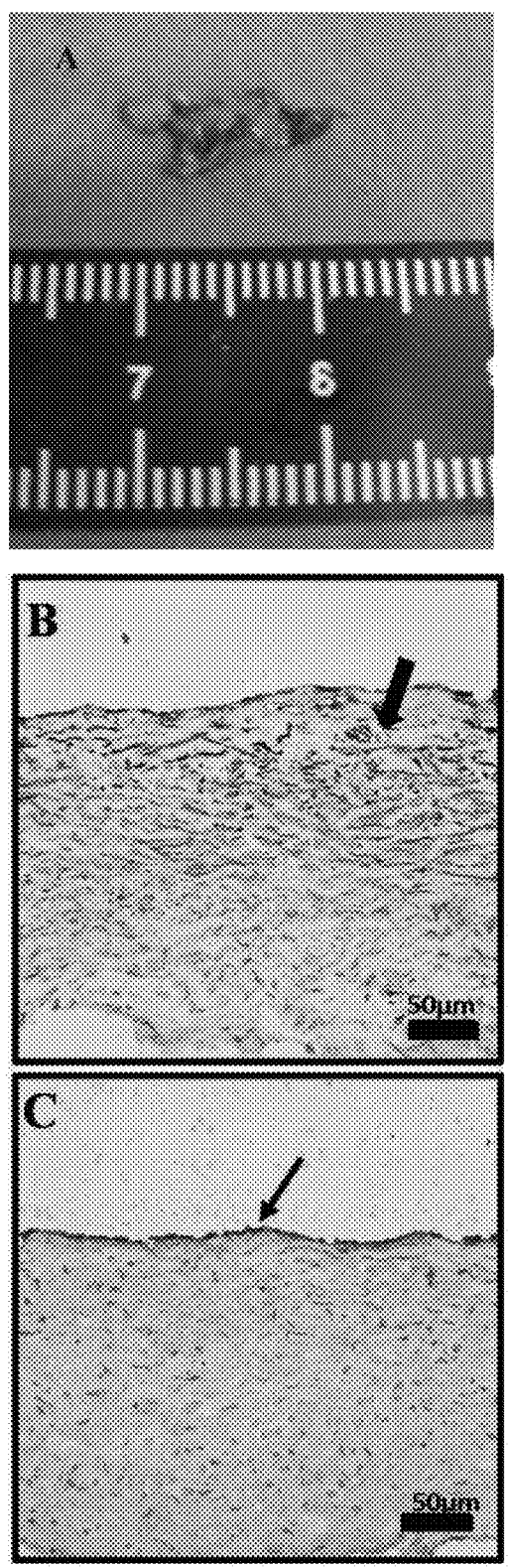

FIG. 17A to FIG. 17C show the cross-sectional view of an artificial blood vessel obtained after 14 days of implantation of an artificial blood vessel progenitor into a Rhesus monkey in Example 6, and the immunohistochemical staining results of the artificial blood vessel.

FIG. 17A shows the cross-sectional view of an artificial blood vessel obtained after 14 days of implantation of an artificial blood vessel progenitor into a Rhesus monkey.

FIG. 17B shows the result of α-SMA staining. As indicated by the thick arrow in the figure, some adipose-derived mesenchymal stem cells differentiate into smooth muscle cells in the artificial blood vessel.

FIG. 17C shows the result of CD31 staining. As indicated by the thin arrow in the figure, some adipose-derived mesenchymal stem cells differentiate into endothelial cells in the artificial blood vessel.

Figures 18A, 18B, 18C, 18D:
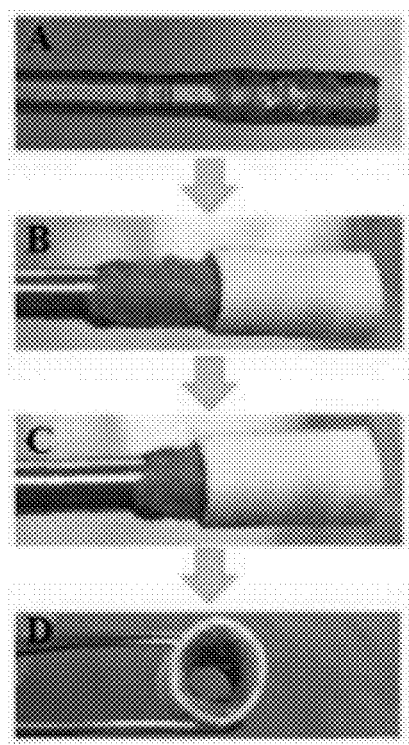

FIG. 18A to FIG. 18D show a method of preparing an artificial blood vessel progenitor in Example 7. FIG. 18A: bio-blocks are printed on a rotary rod to form a tubular biological construct; FIG. 18B and FIG. 18C: an artificial blood vessel is sleeved from the left to the right over the tubular biological construct; FIG. 18D: the artificial blood vessel and the tubular biological construct are adhered together to form an artificial blood vessel progenitor.

FIG. 19A to FIG. 19D depict a method in Example 8 of preparing an artificial blood vessel progenitor by using a degradable polylactic acid tubular support and bio-blocks prepared in Example 1.

Figures 19A, 19B, 19C, 19D:
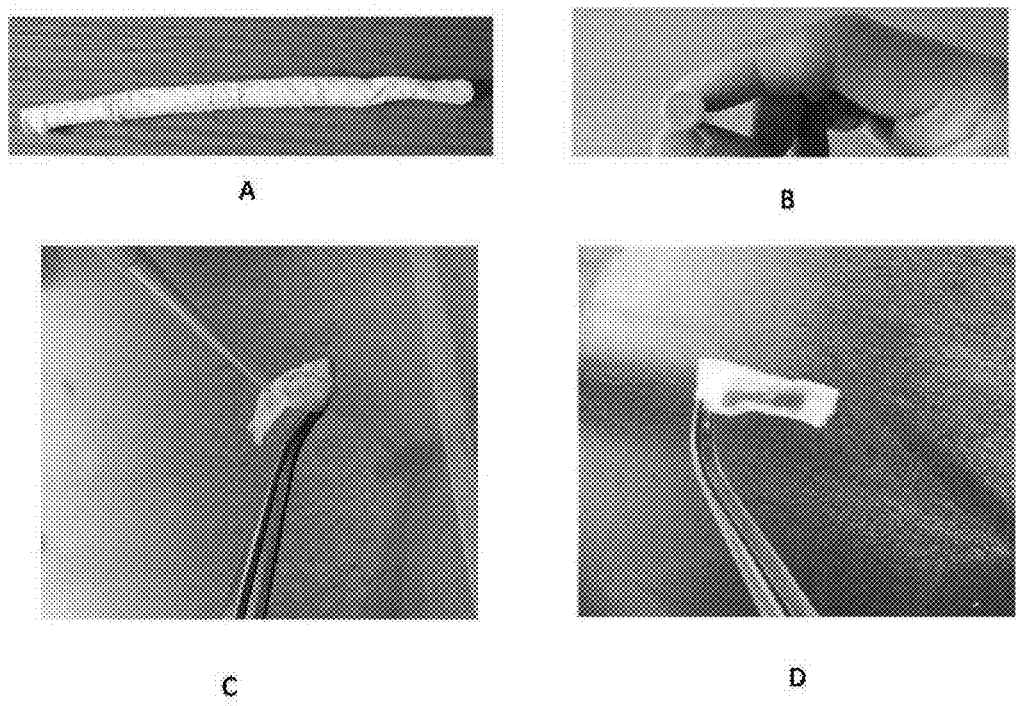

FIG. 19A and FIG. 19B show a tubular solid support made of polylactic acid as a base material by an electrospinning process.

FIG. 19C shows the following procedures: cutting the polylactic acid tubular support, dropping a medical adhesive on one side of the tubular support, and placing bio-blocks on corresponding position of the other side of the tubular support.

FIG. 19D shows that the medical adhesive can permeate the tube wall so that the bio-blocks and the inner wall of the tubular support are adhered together to obtain an artificial blood vessel progenitor.

The above procedures are only for the convenience of observation and photographing. In a practical preparation process, a medical adhesive is dropped on the outer wall of a polylactic acid tubular solid support so that the medical adhesive permeates into the inner wall. The medical adhesive can permeate the wall of the electrospun polylactic acid, whereby the bio-blocks are immobilized. The above results show that, on the one hand, polylactic acid can be used as a solid support material, on the other hand, a medical adhesive can permeate through the wall of a solid support obtained by electrospinning due to its permeability from porous structure, and the medical adhesive can be dropped on one side of the solid support and bio-blocks can be placed on the other side so as to immobilize the bio-blocks, thereby obtaining an artificial tissue progenitor.

Figures 20A, 20B, 20C, 20D, 20E, 20F, 20G:
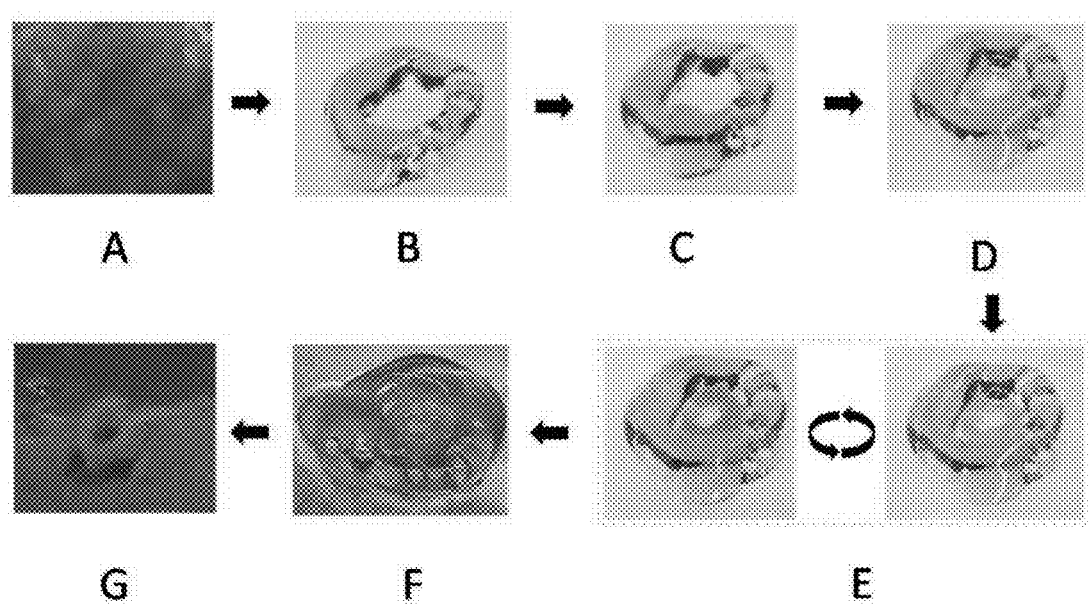

FIG. 20A to FIG. 20G show the experimental procedures and experimental results for the preparation of a tubular three-dimensional construct using bio-blocks, fibrinogen and thrombin in Example 9, wherein FIG. 20A shows that fibrinogen is adhered/assembled on the surface of the bio-blocks; FIG. 20B shows an annular auxiliary structure is constructed with an auxiliary material (optional step); FIG. 20C shows that a second agent is added dropwise along the annular auxiliary structure to draw an annular pattern; FIG. 20D shows that an assembly unit is placed on the annular pattern to form an annular structure; FIG. 20E shows that, an annular pattern is drawn on upper surface of the annular structure with a second agent and then an assembly unit is placed on the annular pattern (optionally, this step can be repeated for one or more times to construct a construct containing a multilayer structure); FIG. 20F shows the resulting tubular structure; FIG. 20G shows the removal of the auxiliary structure (optional step). The experimental results show that the method of the present invention can be used to construct a tubular three-dimensional construct rapidly, multidirectionally and accurately.

Figures 21A, 21B:
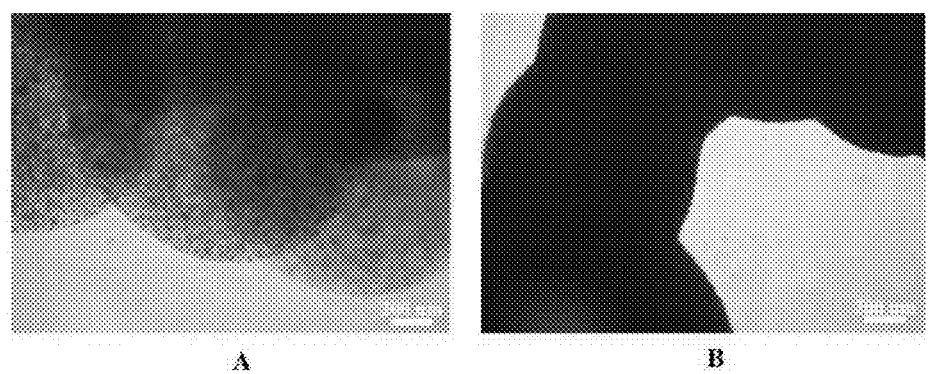

FIG. 21A to FIG. 21B show the microscopic observations of a tubular structure obtained immediately in Example 9 (FIG. 21A) and a cultured tubular structure (FIG. 21B), The results show that in the immediately prepared tubular structure, the bio-blocks have not yet fused with each other, and the cells are uniformly distributed in each bio-block. In the cultured tubular structure, the bio-blocks are completely fused and closely connected with each other, and an intact biological construct is formed.

Figure 22:
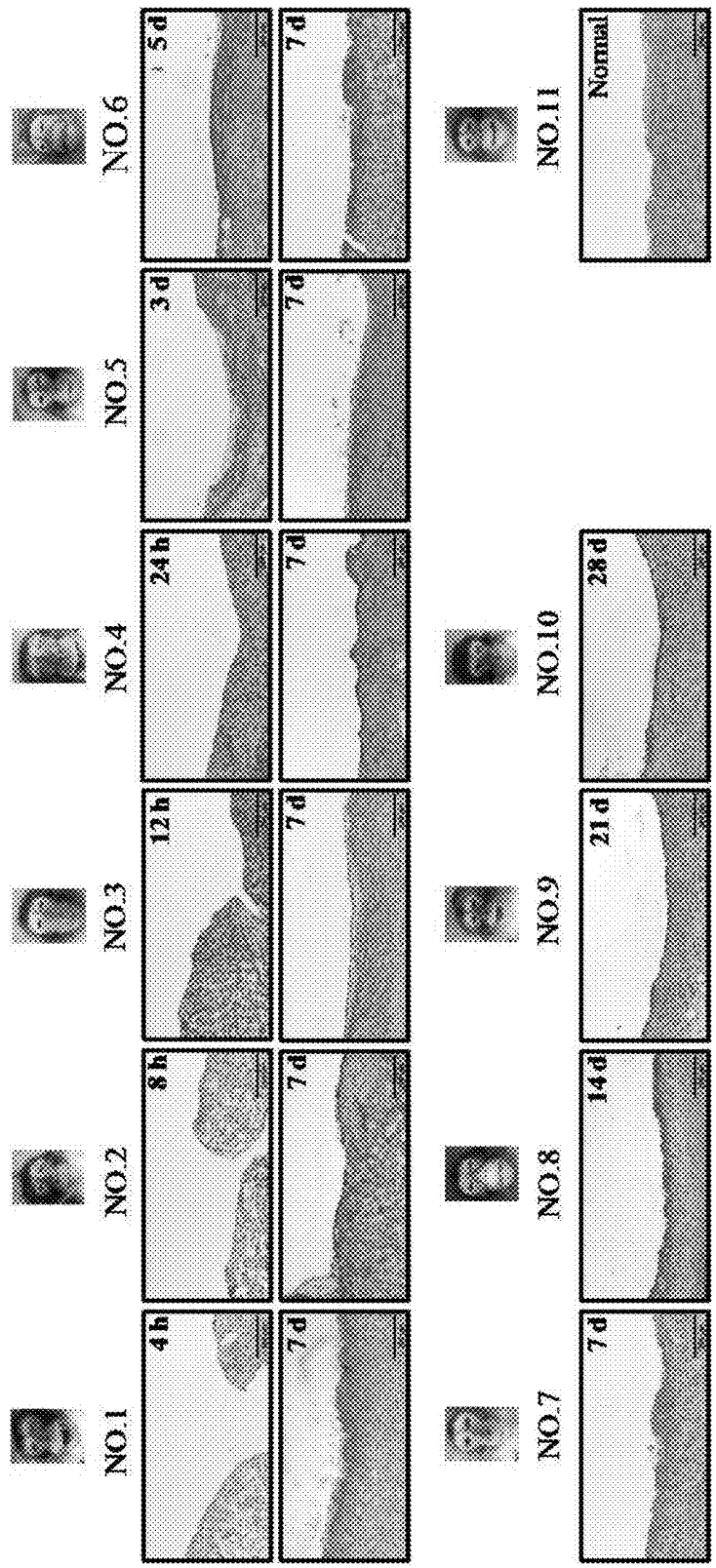

FIG. 22 shows the results of observing and determining the tissue structure of a vascular implant by using HE staining method in Example 10, wherein the scales in the pictures are 200 μm. The results show that after 4 hours of implantation, there are still gaps between the bio-blocks, and the bio-blocks are independent and not connected to each other. After 8 hours to 24 hours of implantation, the bio-blocks are gradually fused together. With the increase of implantation time, an artificial blood vessel formed by fusion of bio-blocks gradually forms a histological structure similar to that of a normal blood vessel.

Figure 23:
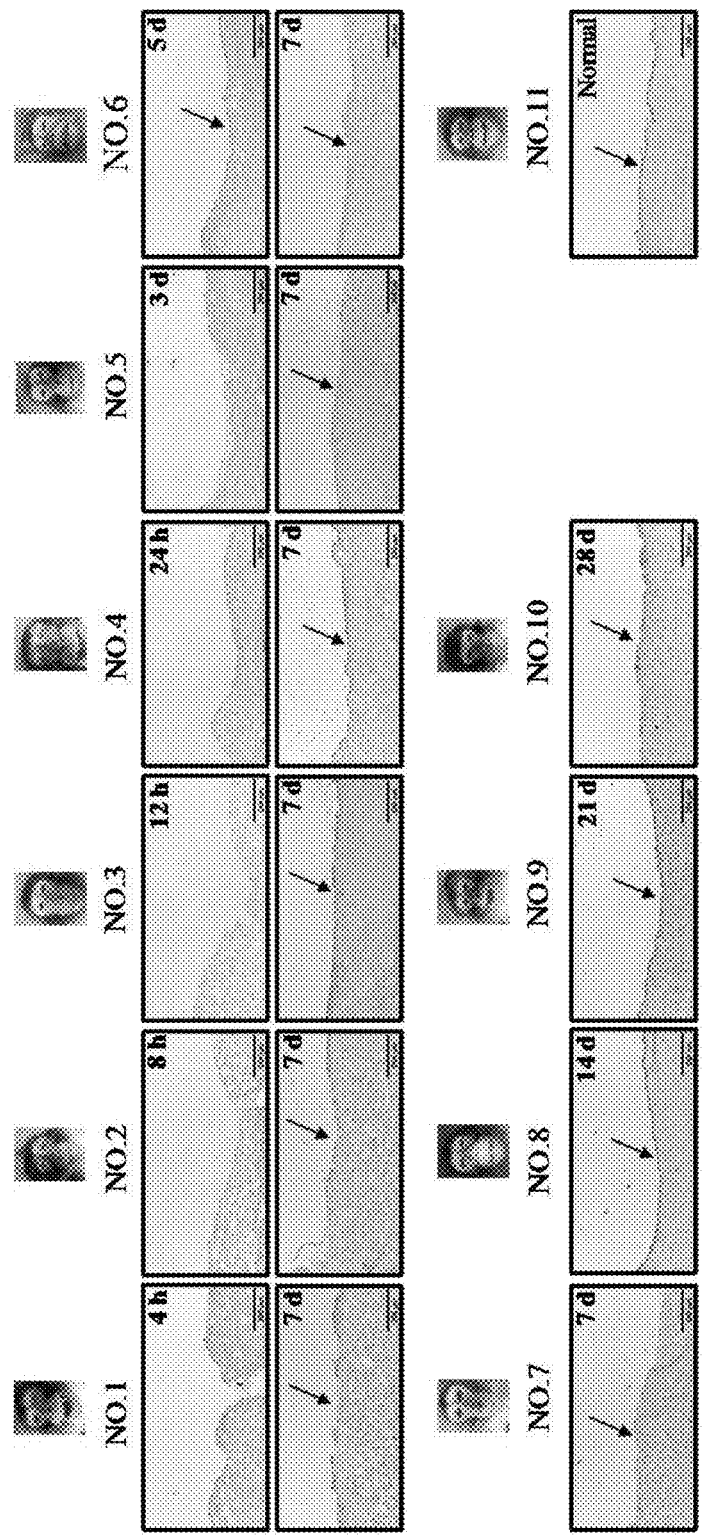
Figure 24:
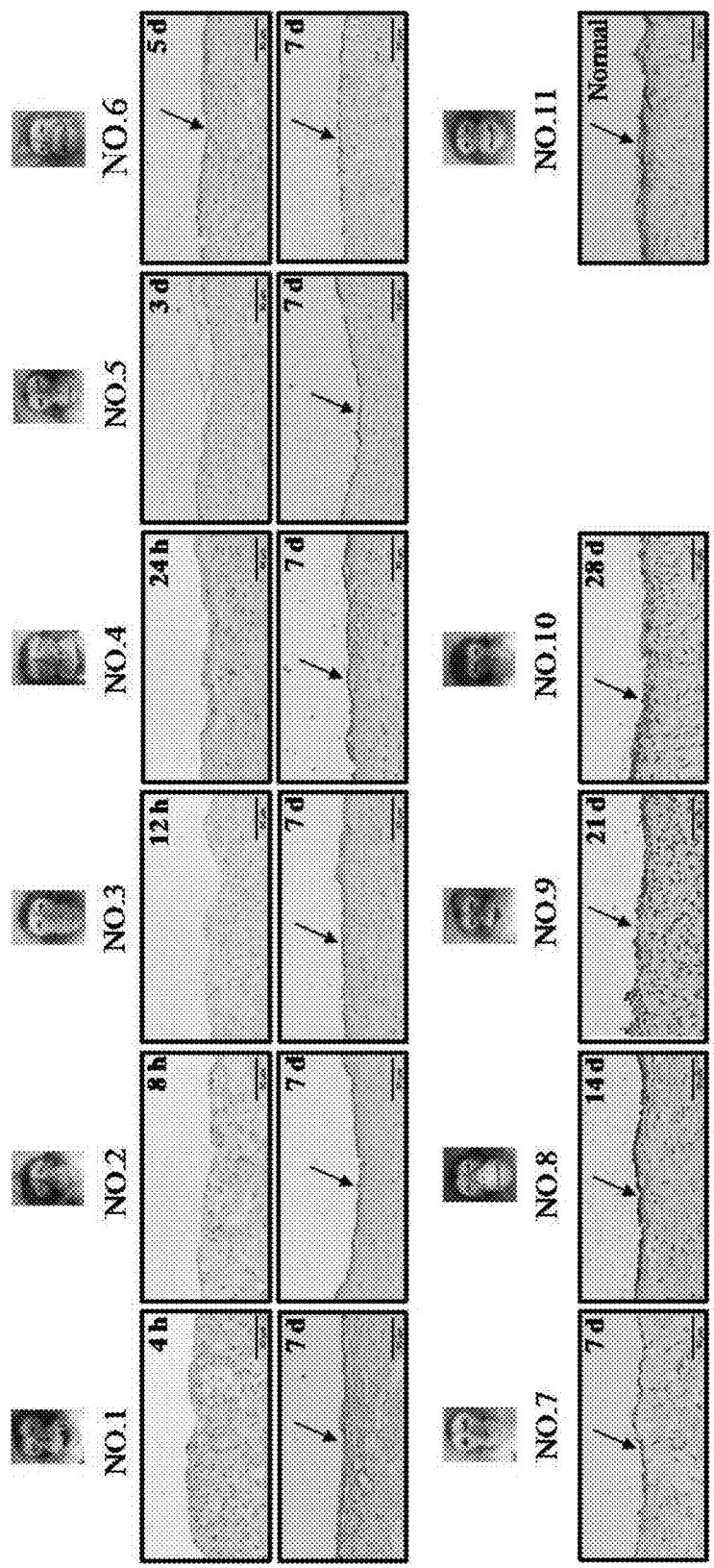

FIG. 23 and FIG. 24 show the results of testing the expression of CD31 in a vascular implant using an immunohistochemical staining method in Example 10. FIG. 23 shows the results magnified by 100 folds with the scale of 200 μm. FIG. 24 shows the results magnified by 400 folds with the scale of 50 μm. The results show that, after 5 days of implantation, endothelial cells appear on the surface on which the vascular implant contacts with blood; with the increase of implantation time, the number of endothelial cells increases continuously. On the $28^{th}$ day, a relatively intact layer of endothelial cells that is similar to that of a normal blood vessel is formed.

Figure 25:
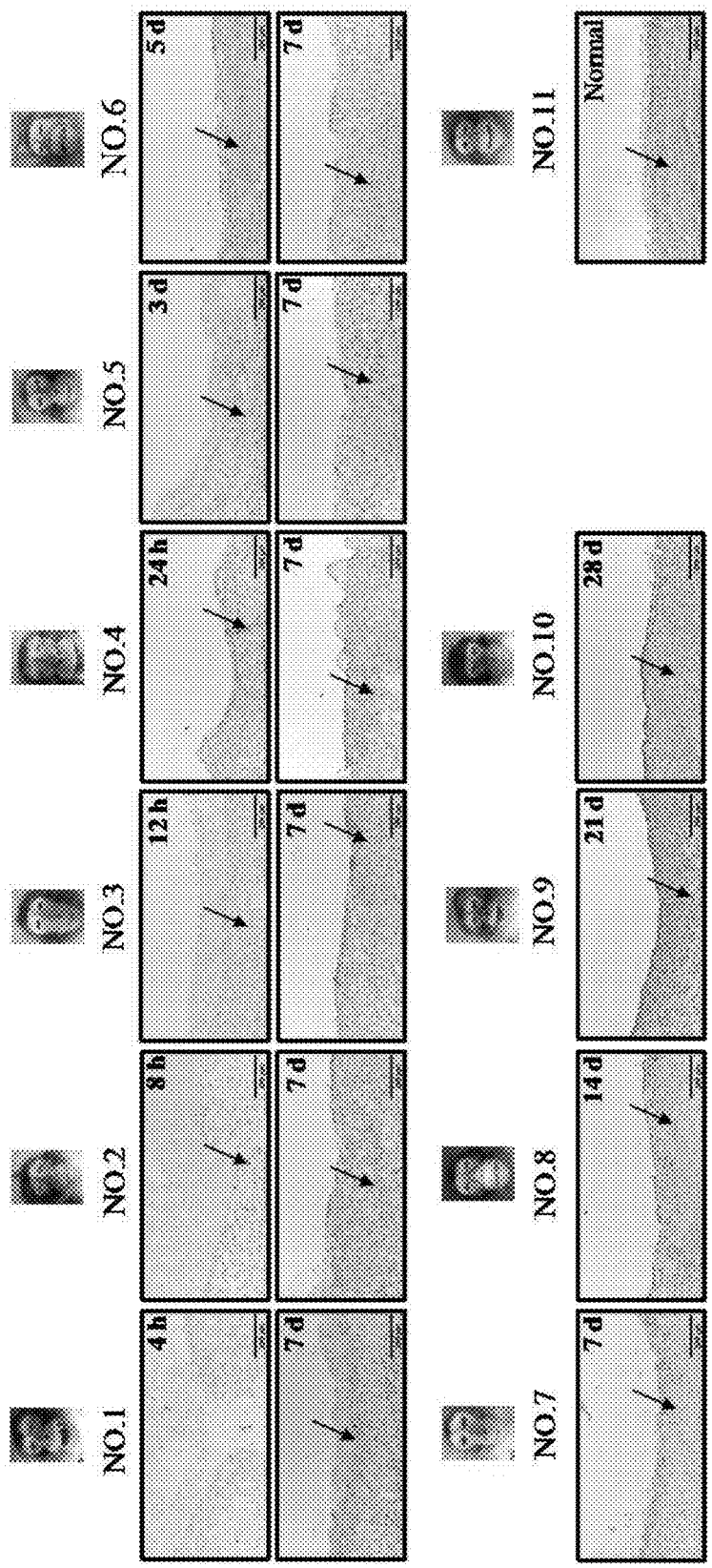

FIG. 25 shows the results of testing the expression of α-SMA in a vascular implant using an immunohistochemical staining method in Example 10, wherein the scale in the figure is 200 μm. The results show that, after 8 hours of implantation, the adipose-derived mesenchymal stem cells encapsulated in the bio-blocks begin to differentiate into smooth muscle cells and express α-SMA; after 3 days of implantation, the morphology of adipose-derived mesenchymal stem cells gradually change into that of smooth muscle cells and the expression of α-SMA further increases; with the increase of implantation time, the number of smooth muscle cells gradually increases, and a layer of smooth muscle cell layer that is similar to that of a normal blood vessel is formed.

Figure 26:
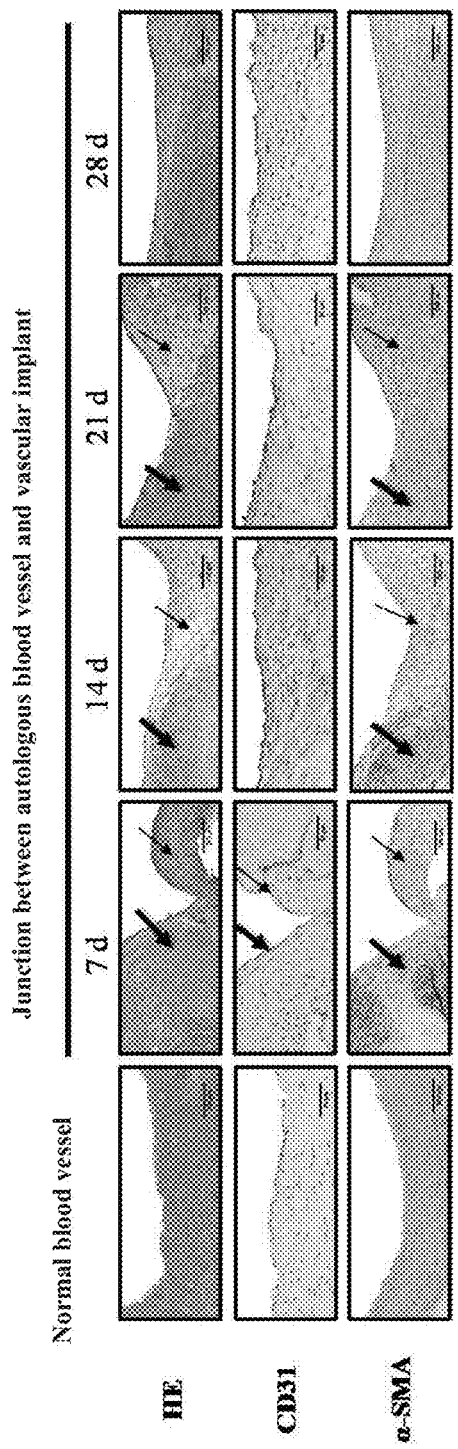

FIG. 26 shows the results of observation of the tissue structure in the junction between an autologous blood vessel of a Rhesus monkey and an vascular implant using HE staining method and the results of testing expressions of CD31 and α-SMA using immunohistochemical staining method, respectively, in Example 11.

The pictures in the first row are the testing results using the HE staining method, and the scale of the figures is 200 μm; the pictures in the second row are the testing results of CD31, and the scale of the figures is 50 μm; and the pictures in the third row are the testing results of α-SMA, and the scale of the figures is 200 μm. The thick arrows in the figures indicate autologous blood vessels and the thin arrows indicate the vascular implants.

The results show that the vascular implant is connected to the autologous blood vessel of the Rhesus monkey on $7^{th}$ day after implantation, but there is significant difference in tissue structure between them from each other, the layer of endothelial cells is continuous but not intact, and the layer of smooth muscle cells is discontinuous. As the implantation time increases, the vascular implant continuously fuses to the autologous blood vessel of the Rhesus monkey; on the $28^{th}$ day after implantation, the vascular implant and the autologous blood vessel of the Rhesus monkey fuse together, the layer of endothelial cells and the layer of smooth muscle cells are continuous and intact, and form a tissue structure similar to that of a normal blood vessel.

Figure 27:
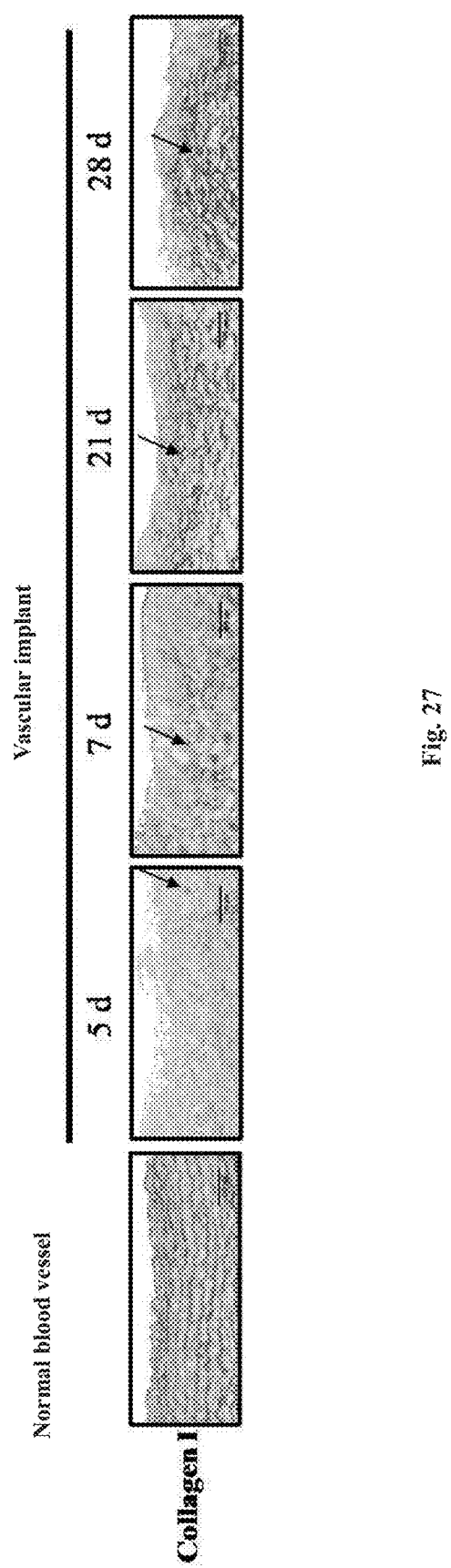

FIG. 27 shows the results of staining vascular collagen using a Sirius Red staining process in Example 12, and the scale of the figures is 100 μm. The results show that: the expression of the collagen begin to appear after 5 days of the implantation; as the implantation time increases, the expressed collagen gradually increases and starts to delaminate to form a collagen structure similar to that of a normal blood vessel.

Figure 28:
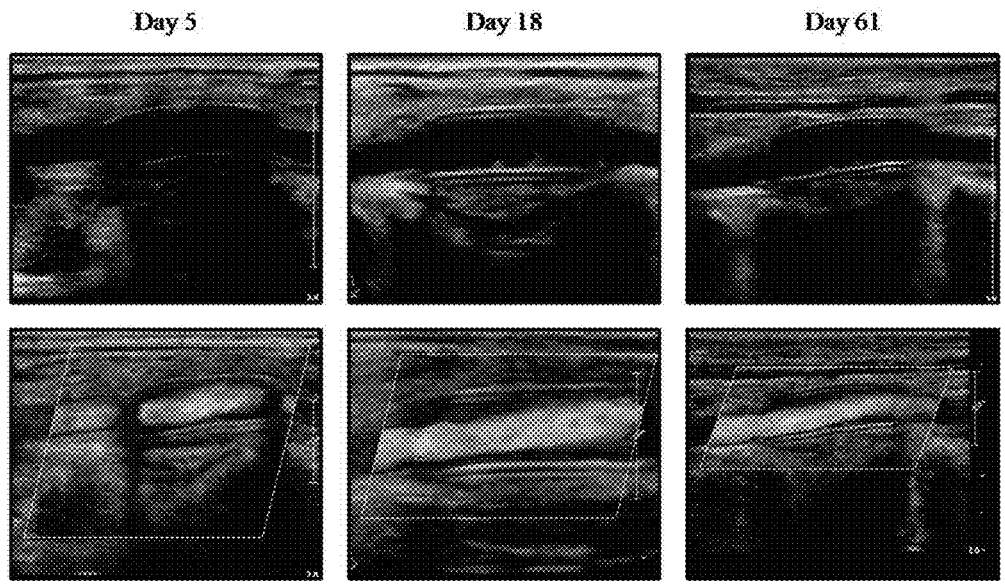

FIG. 28 shows the results of the ultrasonography (the pictures in the first row) and the color Doppler imaging (the pictures in the second row) on a vascular implant in Example 13. The results show that: the blood vessels in the vascular implant are unblocked and blood flow therein is continuous, the inner surface of lumen is smooth without thrombosis or abnormal proliferation, and there is no stenosis at the junction with the normal blood vessel.

Figure 29:
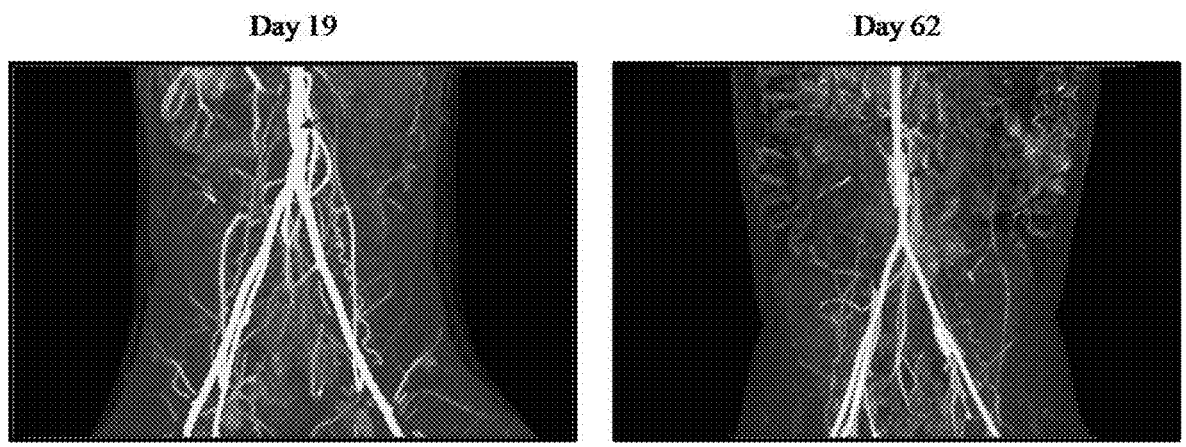

FIG. 29 shows the results of enhanced CT examination on the vascular implant in Example 14. The results show that, in the vascular implant, the blood flows smoothly without blockage.

Figures 30A, 30B, 30C, 30D:
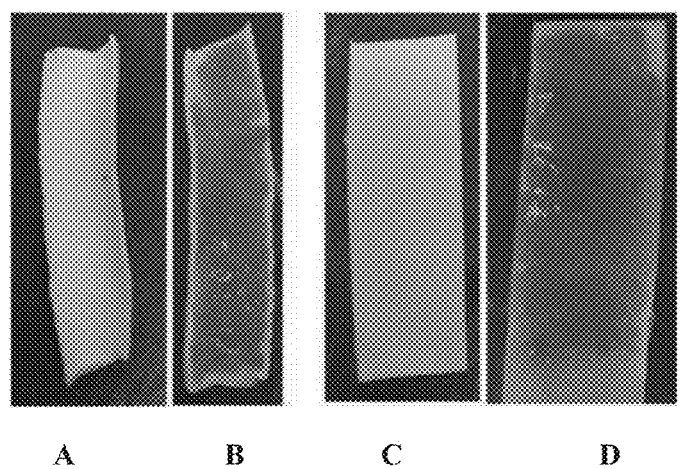

FIG. 30A and FIG. 30B show an expanded polytetrafluoroethylene sheet-like solid support and a vascular patch progenitor formed by 3D printing bio-blocks thereon, respectively, in Example 15.

FIG. 30C and FIG. 30D show a polycaprolactone sheet-like solid support and a vascular patch progenitor formed by 3D printing microcapsules thereon, respectively, in Example 16.

Figures 31A, 31B:
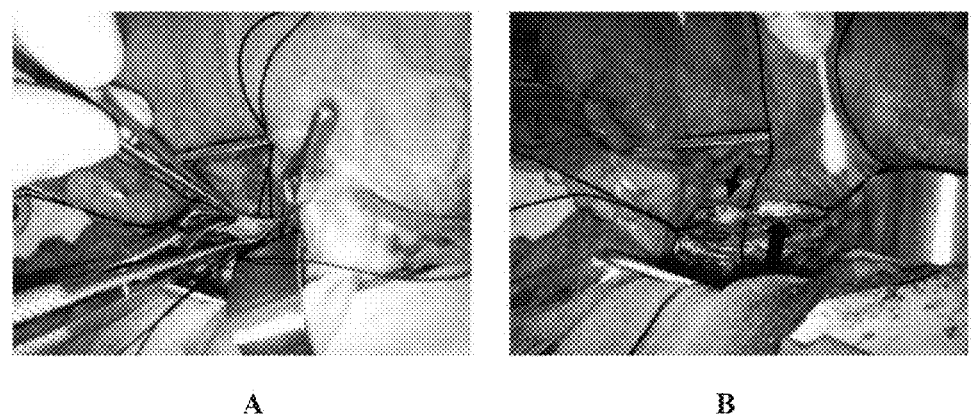

FIG. 31A and FIG. 31B show the creation of a vascular defect in the abdominal aorta of a Rhesus monkey and the suture of a vascular patch progenitor to the defect site respectively, in Example 17. In FIG. 31B, what is indicated by the thick arrow is a vascular patch progenitor containing bio-blocks prepared in Example 15, and what is indicated by the thin arrow is a vascular patch progenitor containing microcapsules prepared in Example 16.

Figures 32A, 32B:
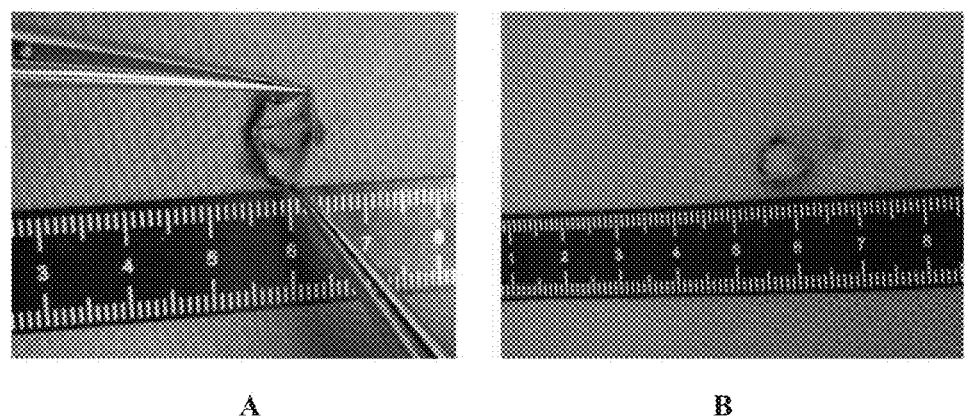

FIG. 32A and FIG. 32B show a blood tissue formed from a vascular patch progenitor containing bio-blocks or from a vascular patch progenitor containing microcapsules after 7 days of implantation, respectively, in Example 17. As shown in the figures, the bio-blocks or microcapsules in the patch are fused together to form an intact intima.

FIG. 33A to FIG. 33D show the result of CD31 and α-SMA immunohistochemical staining of the vascular tissue in Example 17.

Figures 33A, 33B, 33C, 33D:
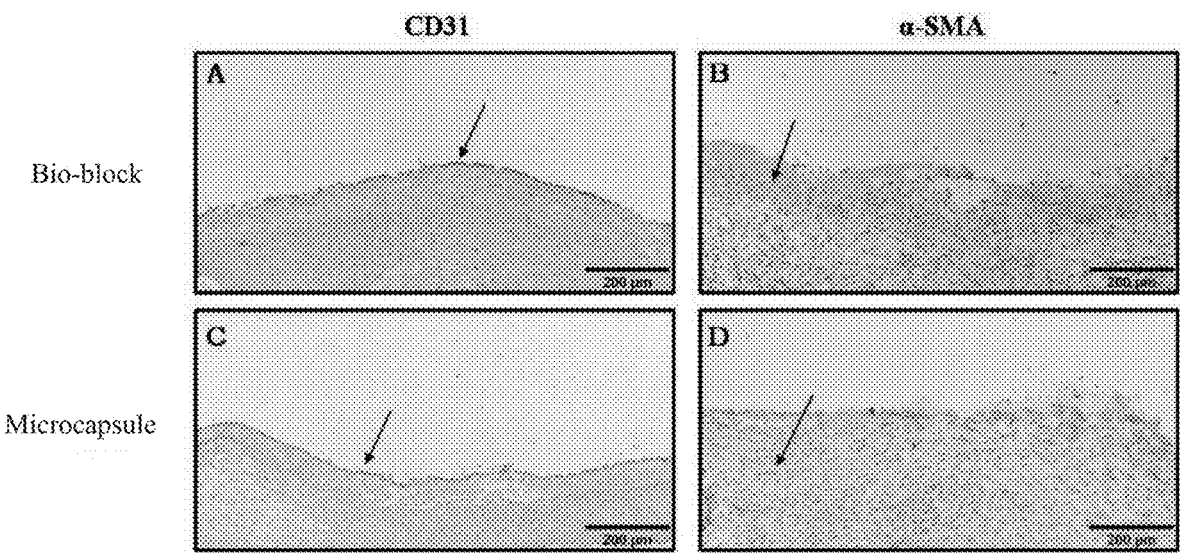

FIG. 33A and FIG. 33B show the examination result of a vascular tissue formed from a vascular patch progenitor containing bio-blocks. The results show that the adipose-derived mesenchymal stem cells in the bio-blocks differentiate into endothelial cells (FIG. 33A) and smooth muscle cells (FIG. 33B), after 7 days of implantation.

FIG. 33C and FIG. 33D show the examination result of a vascular tissue formed from a vascular patch progenitor containing microcapsules. The results show that the adipose-derived mesenchymal stem cells in the microcapsules differentiate into endothelial cells (FIG. 33C) and smooth muscle cells (FIG. 33D), after 7 days of implantation.

Figure 34:
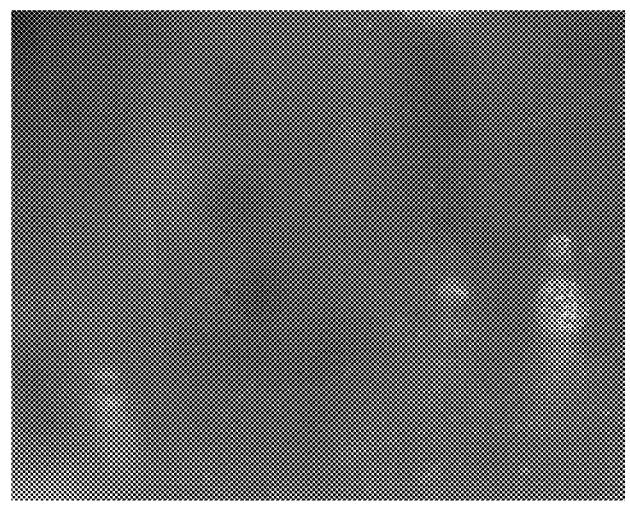

FIG. 34 shows the state of bio-blocks in the elasticity modulus test in Example 18.

Figure 35:
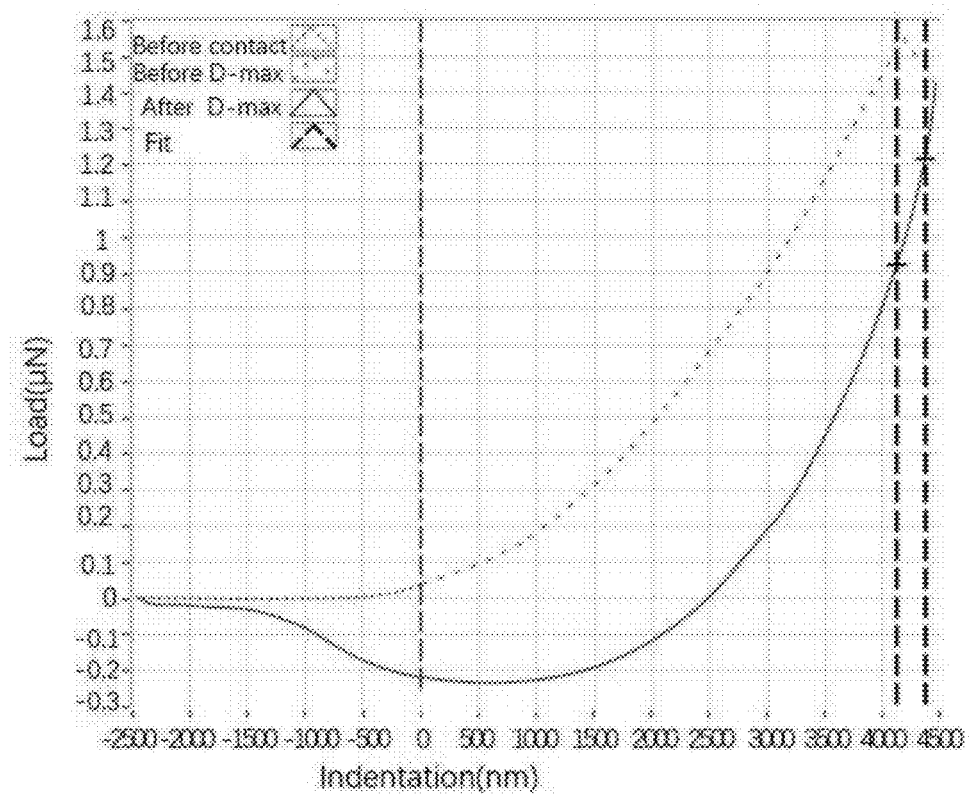

FIG. 35 shows the stress-strain curve of bio-blocks prepared in Example 18, wherein the effective Young's modulus of the bio-blocks is of 24.77 kPa.

Figure 36:
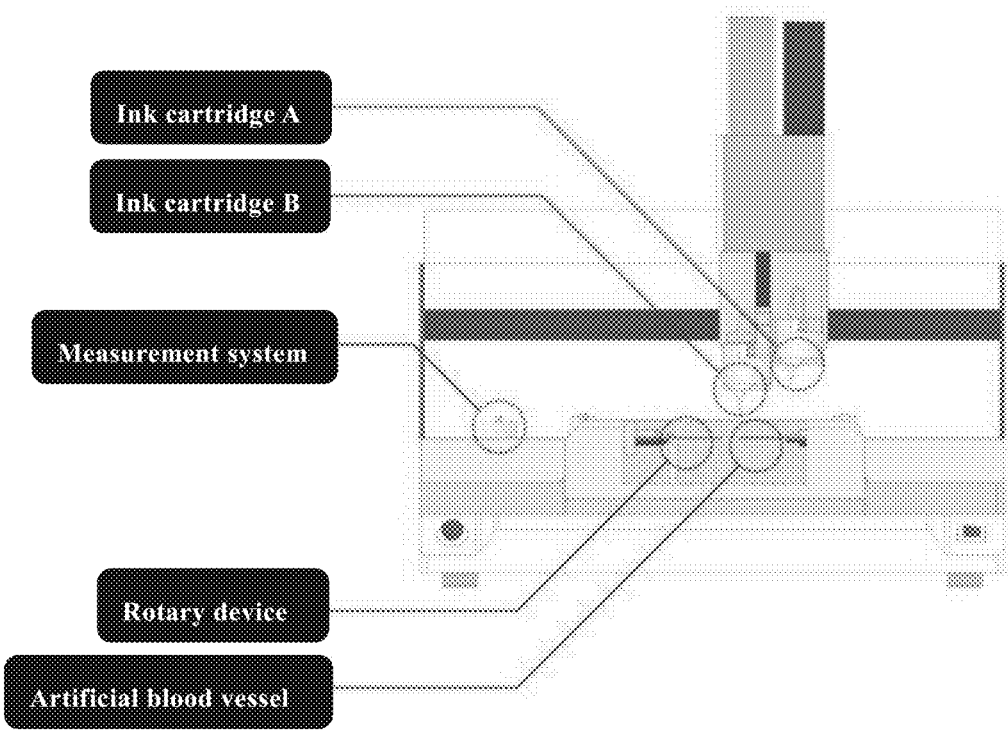

FIG. 36 schematically shows the main structure of a 3D bio-printer used in Example 19.

Figure 37:
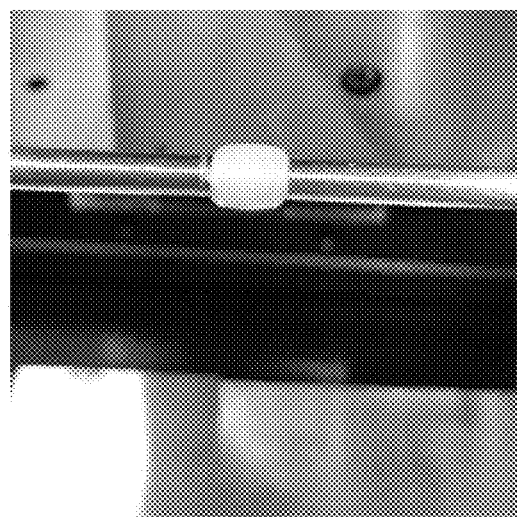

FIG. 37 shows a tubular biological construct formed on the rotary rod of a rotary device, having a length of 20 mm and a thickness of about 1 mm, in Example 19.

Figure 38:
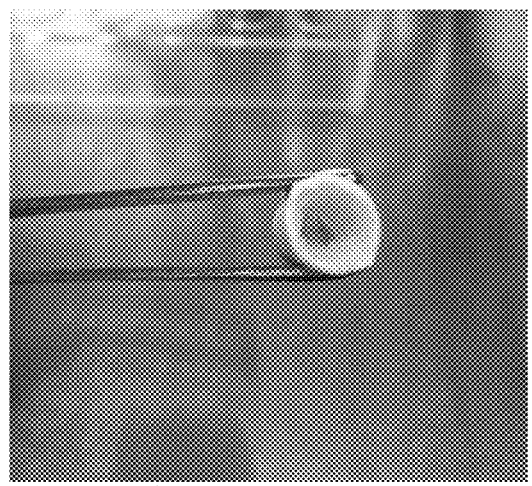

FIG. 38 shows an artificial blood vessel progenitor prepared in Example 19.

Figure 39:
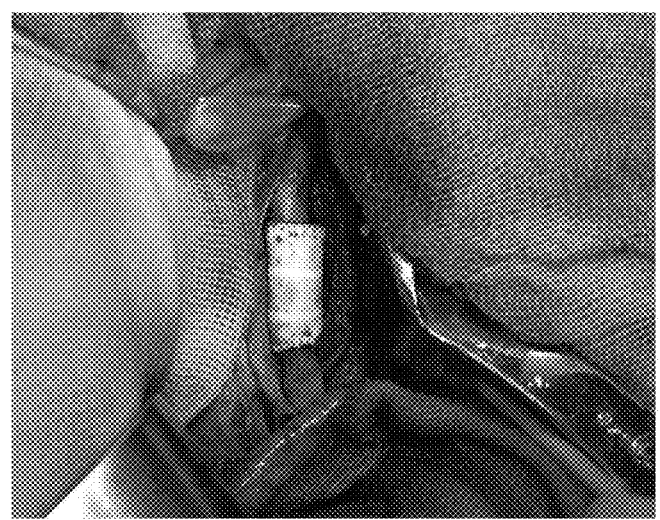

FIG. 39 shows an artificial blood vessel progenitor implanted in a Rhesus monkey in Example 19.

Figure 40:
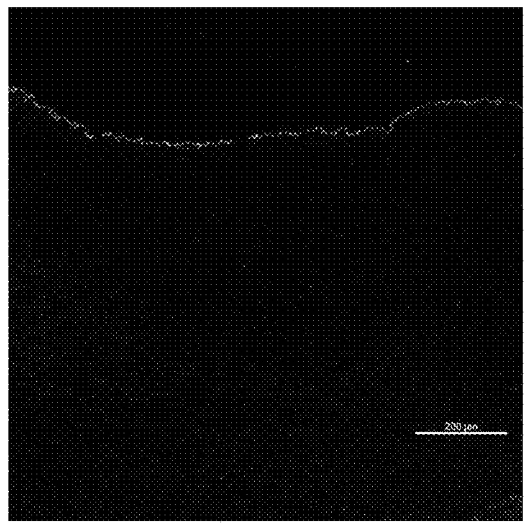

FIG. 40 shows a fluorescence photomicrograph of a vascular implant, wherein vascular endothelial cells are fluorescently labelled with green fluorescence, and the scale of the figure is 200 μm, in Example 19. As shown in the figure, the vascular implant forms an intact layer of endothelial cells.

Figure 41:
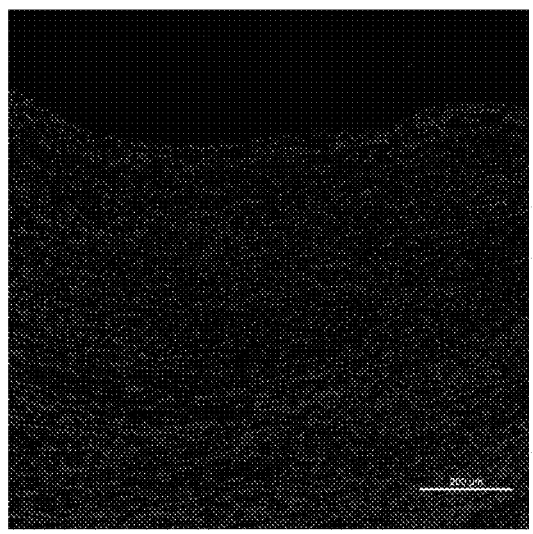

FIG. 41 shows a fluorescence photomicrograph of a vascular implant, wherein vascular smooth muscle cells are fluorescently labeled with red fluorescence, and the scale of the figure is 200 μm, in Example 19. As shown in the figure, the vascular implant forms an intact layer of smooth muscle cells.

FIG. 42A to FIG. 42H show a 3D bio-printer used in Example 20 (FIG. 42A) and the steps of printing in Example 20 (FIGS. 42B-H).

Figures 42A, 42B, 42C, 42D, 42E, 42F, 42G, 42H:
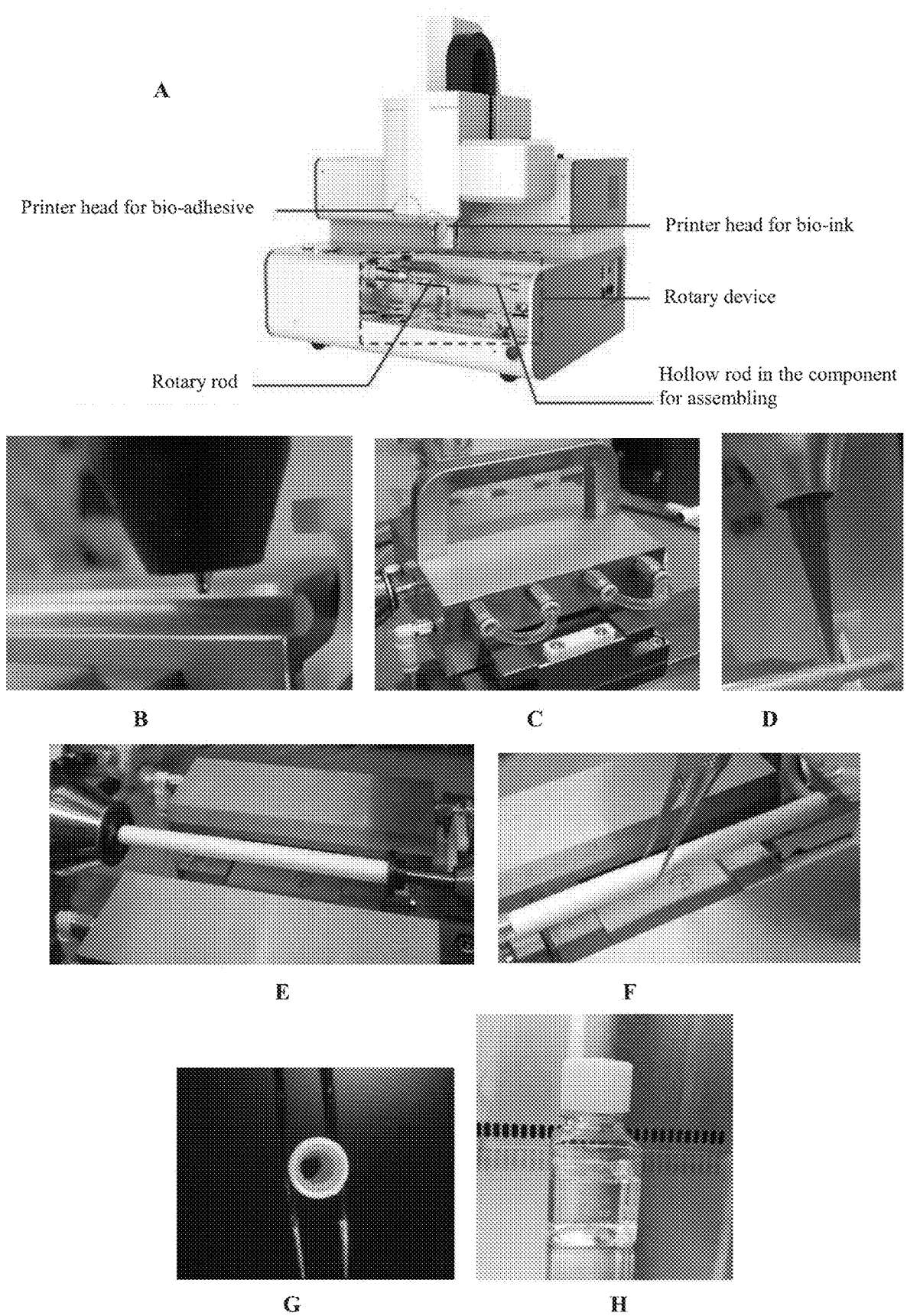

As shown in FIG. 42A, the 3D bio-printer comprises two printer heads for injecting bio-ink and bio-adhesive respectively; the 3D bio-printer further comprises a rotary device, which comprises a rotary rod covered with an elastic film on the outer wall and comprises a component (comprising a hollow rod) for assembling.

FIGS. 42B-H show the following steps in order:

(1) the bio-ink is extruded through the printer head form a bio-ink coating on the elastic film on the rotary rod (FIG. 42B);

(2) the bio-ink coating on the rotary device is subjected to a preforming process at low temperature (2° C., 25 min) (FIG. 42C);

(3) the bio-adhesive is evenly printed onto the bio-ink coating through the printer head (FIG. 42D);

(4) after printing the bio-adhesive, a Gore artificial blood vessel was immediately covered outside the bio-ink coating via the component for assembling (FIG. 42E);

(5) after assembling, the elastic film was expanded by filling with air, making the bio-ink contact with the inner wall of Gore artificial blood vessel, and making them stick together by the bio-adhesive; the expanding is continued for 10 s;

(6) the assembled blood vessel progenitor was removed from the rotary device (FIGS. 42F-G);

(7) the blood vessel progenitor was immersed in blood vessel preservation solution (FIG. 42H).

Figure 43:
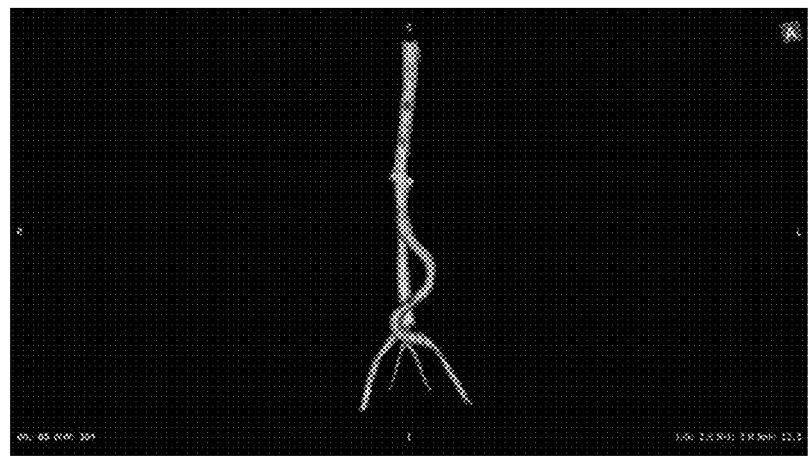

FIG. 43 shows the CT examination result of Example 21, 7 days after the operation. The result shows that the blood flows smoothly.

Figure 44:
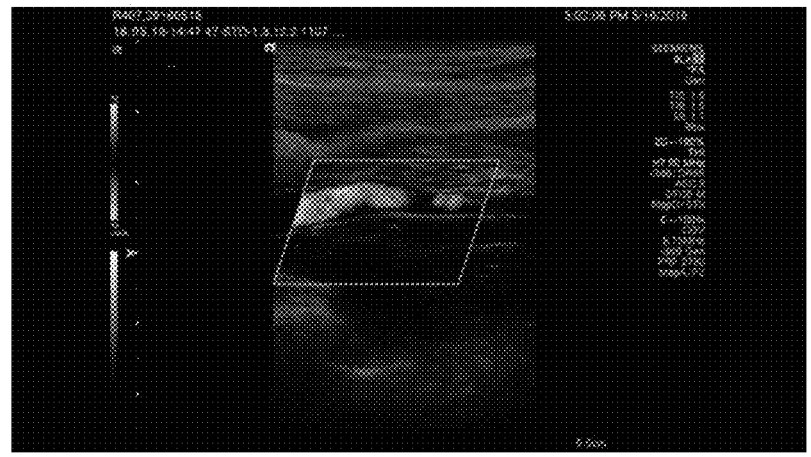

FIG. 44 shows the result of color Doppler imaging 7 days after the operation of Example 21, and the result shows that blood flowed on both sides of the artificial blood vessel is in the same direction, providing that the blood vessel is unobstructed and there is no abnormal proliferation or stenosis.

Figure 45:
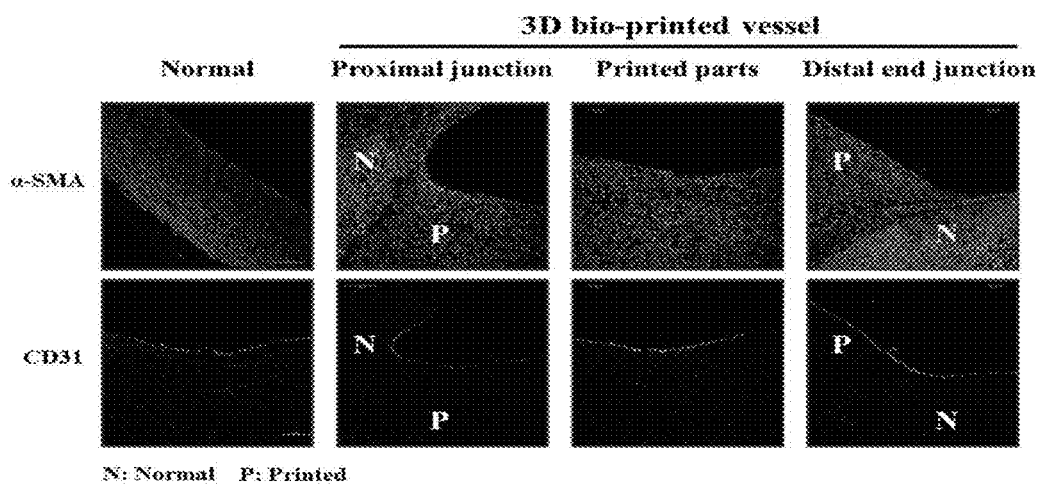

FIG. 45 shows the results of immunofluorescence test 63 days after the operation of Example 21, wherein α-SMA was used for labelling smooth muscle cells and CD31 was used for labelling endothelial cells. The results showed that 63 days after the implantation, the artificial blood vessel progenitor formed intact layers of endothelial cells and smooth muscle cells and fused with the autologous blood vessel.

DETAILED DESCRIPTION OF THE INVENTION

In the present invention, the scientific and technical terms used herein have the meaning as commonly understood by a person skilled in the art unless otherwise specified. Also, the laboratory procedures of cell culture, molecular genetics, nucleic acid chemistry and immunology used herein all are routine procedures widely used in corresponding fields. In the meantime, in order to understand the present invention preferably, definitions and explanations of related terms are provided below.

As used in this specification and the annexed claims, the singular forms "a", "an" and "the" include plural referents unless it is clearly specified in the context otherwise. In addition, any reference to "or" herein is intended to include "and/or" unless stated otherwise.

As used herein, the term "microcapsule" refers to a microstructure (e.g., a micrometer-scale to millimeter-scale structure) containing a cell and a biocompatible material, wherein the cell is encapsulated within the biocompatible material. The microcapsule of the present invention has a stable structure under a physiological condition (e.g., at 4-37° C., e.g., at a pH of between 6 and 8, e.g., with fluid shear under a physiological condition). In some preferred embodiments, the microcapsule has a mechanical strength that avoids breakage of the microcapsules during aspiration or compression.

As used herein, the term "tissue" refers to a cell aggregation composing of cell populations that have the same or similar morphology and the same function, and often also contains non-cellular materials (called as intercellular substances such as matrices, fibers, etc.). A tissue comprises one or more cells.

As used herein, the term "organ" refers to a structure that composes of different cells and tissues and can be used to accomplish one certain or some particular functions. An organ comprises one or more tissues.

As used herein, the term "artificial tissue" refers to a tissue that is not formed through a generation or development process of a native tissue. The artificial tissue may be a human-made tissue, for example, a tissue obtained by culturing an artificial tissue progenitor.

As used herein, the term "artificial tissue progenitor" refers to an object comprising a solid support and a plurality of microcapsules of the present invention, wherein at least one microcapsule is attached to the solid support. In certain embodiments, the artificial tissue progenitor comprises a solid support and a biological construct that is constructed from microcapsules. In certain embodiments, the artificial tissue progenitor of the present invention is capable of forming an artificial tissue following steps of culturing, inducing, and the like.

In the present invention, the term "biological construct" refers to an object constructed by using the microcapsules of the present invention, which may have a two-dimensional or three-dimensional structure and may be used to prepare an artificial tissue progenitor.

As used herein, the term "attach to" means that no relative displacement occurs. In certain embodiments, that a microcapsule or biological construct is attached to a solid support means that the microcapsule or biological construct is bound to the solid support.

As used herein, the term "solid support" refers to a shaped object to which a microcapsule or a biological construct made of microcapsules is attached in the artificial tissue progenitor of the present invention. The solid support can provide a corresponding area for the biological construct to be fully attached thereto.

As used herein, the term "lumen" refers to an organ that is tubular in shape and has a hollow cavity, such as, a circulatory lumen, digestive lumen, respiratory lumen, urinary lumen, or genital lumen, for example, blood vessels, esophagus, trachea, stomach, bile duct, gut (including small intestine and large intestine, such as duodenum, jejunum, ileum, cecum (including appendix), ascending colon, right colic flexure, transverse colon, left colic flexure, descending colon, sigmoid colon, rectum), fallopian tube, vas deferens, ureter, bladder or lymphatic vessel).

As used herein, the term "artificial lumen" includes a lumen that is not formed by a generation or development process of a native tissue, and a sheet-like artificial tissue that is capable of forming a lumen together with a native tissue. The artificial lumen can be obtained by culturing the artificial tissue progenitor of the present invention.

As used herein, the term "artificial blood vessel" refers to a human-made vascular substitute that is typically in the form of a tube. In some embodiments, an artificial blood vessel is used to reconstruct or repair stenosed, occluded, dilated, damaged, or deformed blood vessels. In some embodiments, the artificial blood vessel is obtained by culturing (e.g., culturing in vitro or in vivo) a tubular artificial tissue progenitor of the invention.

As used herein, the term "vascular patch" refers to an object used to repair damaged blood vessels, which is typically in the form of a sheet. Vascular patch can be used to repair vascular fistula caused by hemangioma, vascular stenosis and the like, and is usually applied in large vessels such as aorta etc. In general, a vascular patch is required to be easily sutured and to stanch. A vascular patch can be applied to patients with defective vascular wall but without the need for total vascular resection. In some embodiments, the vascular patch is obtained by culturing (e.g., culturing in vitro or in vivo) a sheet-like artificial tissue progenitor of the present invention.

As used herein, the term "lumen implant" refers to an object that can be implanted into a subject for replacement, reconstruction or repair of lumens of the subject, comprising one or more artificial tissue progenitors (e.g., tubular artificial tissue progenitors or sheet-like artificial tissue progenitors) of the present invention or one or more artificial lumens. In some embodiments, the lumen implant of the present invention comprises a plurality of tubular artificial tissue progenitors (or artificial lumens), and the tubular artificial tissue progenitors (or artificial lumens) is in fluid communication. The lumen implant of the present invention may have a linear tubular structure or a branched tubular structure, for example, may be an X-shaped tube, a Y-shaped tube or a T-shaped tube. In some embodiments, the luminal implant is a blood vessel implant. In certain embodiments, the lumen implant further comprises a pharmaceutically active ingredient, a sensing device and/or a conditioning device.

As used herein, the term "mechanical protection" means that microcapsules have a certain mechanical strength (for example, a mechanical strength that avoids breakage of the microcapsules during aspiration or extrusion) so as to reduce or avoid the environmentally mechanical damage to the cells encapsulated therein. In addition, when microcapsules are used to prepare an artificial tissue progenitor for transplantation or repair of a lumen, the microcapsules can prevent the cells encapsulated therein from being washed away by the fluid in the lumen, which facilitates the conversion of the artificial tissue progenitor into a normal tissue.

As used herein, the term "mechanical protection" means that microcapsules (e.g., bio-blocks) can protect cells encapsulated therein from damages caused by mechanical force (including shear and squeezing pressure) during handling of cells (e.g., during 3D bio-printing). After implanted into a body, an artificial tissue progenitor (e.g., an artificial blood vessel progenitor) constructed with microcapsules progenitor can protect the cells encapsulated in the microcapsules from being washed away by a fluidizing body fluid (e.g., blood flow), and facilitate the conversion of an artificial tissue into a normal tissue.

As used herein, the term "biocompatible material" refers to such a material and its degradation product is non-toxic to a cell and is compatible with a host after implanted into the host (e.g., a human body), without resulting in significant or a serious side effect, for example, it does not cause a toxic effect in a host (e.g., a human tissue) and does not cause an immunologic rejection, an allergic reaction or an inflammatory response etc. in the host.

As used herein, the term "biodegradable material" refers to such a material that can be degraded and absorbed by a cell or an organism, and degradation products thereof are biocompatible. The material can be of a natural origin (e.g., from an animal or a plant) or can be synthetic.

As used herein, the term "bio-material" refers to a natural or artificial material that can be used to diagnose, repair or enhance the function of a human tissue or an organ, and it can be used to replace or repair a living tissue, and perform, enhance or replace a lost certain function of a tissue due to a disease or an injury etc. Biomaterials mainly include metal materials (e.g., alkali metals and alloys thereof), inorganic materials (e.g., bioactive ceramics, hydroxyapatite, etc.) and organic materials. The organic materials mainly include polymer materials. Depending on the use of a material, the biomaterials can be divided into bioinert, bioactive and biodegradable materials.

As used herein, the term "viscosity" refers to a measurement of the viscosity of stickiness of a fluid and represents an internal frictional phenomenon resulted from dynamics of the fluid. Two plates with an area of 1 m² are immersed in a liquid and the distance between the two plates is 1 m. If a shear stress of 1 N is applied to one of the plates so that the relative velocity between the two plates is 1 m/s, the viscosity of the liquid is 1 Pa·s.

As used herein, the term "bio-printing" refers to printing by utilizing a biological material (including but not limited to a biological molecule such as protein, lipid, nucleic acid and metabolite; cell such as cell solution, cell-containing gel, cell suspension, cell concentrate, multicellular aggregate and multicellular bodie; subcellular structure such as organelle and cell membrane; biomolecule-related molecule such as synthetic biomolecule or analogue of a biomolecule). As used herein, the term "printing" refers to a process of depositing a material in a predetermined pattern. In some preferred embodiments, microcapsules are printed by either an extrusion printing process or a modular printing process. Preferably, the microcapsules are printed by using a modular printing process. As used herein, the term "modular printing process" refers to a method for performing printing by imbibing/grasping a module (e.g., a microcapsule of the present invention, such as a bio-block) and precisely positioning/arranging it. Since the microcapsules used in the present invention encapsulate a cell, such a modular printing process is also referred to herein as a "modular bio-printing process". In the present invention, bio-printing is preferably performed by a method that matches an automated or semi-automated, computer-assisted, three-dimensional prototype device (such as a bio-printer). However, in the present invention, the "printing" (e.g., bio-printing) may be performed by various methods, including but not limited to printing by using a printer (e.g., a 3D printer or a bio-printer), printing by using an automated or non-automated mechanical process (instead of a printer), printing by means of manual placement or manual deposition (e.g., by using a pipette).

As used herein, the term "alginic acid" refers to a class of polysaccharides extracted from brown algae, which is a random block copolymer of beta-1,4-D-mannuronic acid (M unit) and alpha-1,4-L-guluronic acid (G unit), In general, M and G units in alginic acid are linked into the block copolymer via 1, 4 glycosidic bond in the way of M-M, G-G or M-G. Alginic acid has an empirical formula $(C_6H_8O_6)_n$, which typically has a molecular weight of 4 kDa to 1500 kDa. As used herein, the term "alginate" refers to a salt formed from alginic acid including, but not limited to, sodium alginate, calcium alginate, strontium alginate, barium alginate and the like.

As used herein, the term "oxidized alginate" refers to a product formed by an oxidation reaction of an alginate (e.g., sodium alginate). In general, the oxidation reaction will allow the hydroxyl groups of some of uronic acid units in the alginate (e.g., sodium alginate) to be oxidized into aldehyde groups.

As used herein, the term "degree of oxidation" refers to a molar fraction of oxidized uronic acid units in the total uronic acid units of an alginic acid or alginate.

As used herein, the "tackifier" refers to an agent that is used to adjust the viscosity of a liquid or semi-solid (e.g., a gel). As described herein, the second agent of the present invention preferably has a viscosity suitable for drawing a pattern or for coating. Therefore, in some preferred embodiments, the viscosity of the second agent can be conveniently adjusted by using a tackifier.

As used herein, the term "bio-block" refers to a base unit that can be used for bio-printing and other purposes, wherein the bio-block comprises a cell, a core encapsulating the cell, and a shell enclosing the core, wherein the core and the shell are each independently made from a biodegradable material. In some preferred embodiments of the present invention, the biodegradable material in the core and the shell can reduce or prevent the cell in the bio-block from being mechanically damaged during handling and can provide a controlled release of a substance (e.g., a nutrient, an extracellular matrix, a cytokine, a pharmaceutically active ingredient, etc.) to promote cell activity and function (proliferation, differentiation, migration, secretion or metabolism) or to maintain cell stemness. In some preferred embodiments of the invention, the bio-block or the shell of a bio-block has a certain mechanical strength so that a three-dimensional deposition can be achieved. In the present invention, it is particularly preferred that the bio-block and the shell thereof have suitable mechanical protection properties (e.g., suitable hardness and/or modulus of elasticity). In some preferred embodiments, the shell is also capable of providing a microenvironment, such as a nutrient, for life activity of the cell.

As used herein, the term "bio-ink" refers to a liquid, semi-solid (e.g., gel) or solid composition that contains one or more microcapsules (e.g., bio-blocks) of the present invention. For example, the bio-ink of the present invention may be a solution, a suspension, a gel or a concentrate containing the microcapsule (e.g., bio-block). In the present invention, the bio-ink can be used for bio-printing to create specific geometries; and preferably, the resulting geometries can be further stacked so as to form a biological construct with a specific shape and structure. In addition, the cell within the microcapsule (e.g., bio-block) in a bio-ink is capable of performing a variety of desired life activities before, during, and/or after bio-printing. In a preferred embodiment, the cell within the microcapsule (e.g., bio-block) is dormant prior to bio-printing and grow and proliferate after bio-printing to form a stable biological construct. In a preferred embodiment, the bio-ink is an extrudable composition. As used herein, the term "extrudable" means that a composition can be shaped by being forced (e.g., under pressure) to pass through a nozzle or orifice.

As used herein, the term "bio-adhesive" refers to an adhesive which can be used for a living organism. Besides being able to realize the binding function, it is particularly preferred that such adhesive has at least one property selected from the group consisting of: (1) it is safe, reliable, non-toxic, non-carcinogenic, non-teratogenic and non-mutagenic; (2) it has a good biocompatibility, and does not hinder the self-healing of organic tissues; (3) it can be used under the conditions of bloods and tissue fluids; (4) it can realize fast adhesion under normal temperature and normal pressure; (5) it has good adhesive strength and durability, wherein the adhered portion has a certain elasticity and toughness; (6) it is non-irritable to organic tissues during use; (7) after the adhesive effect is achieved, relevant components can be gradually degraded and absorbed; and (8) the adhered portion can allow cells to be migrated through. A bio-adhesive may comprise a synthetic polymer (e.g. cyanoacrylate) or other material (e.g. a protein) as main ingredient.

Figure 1:
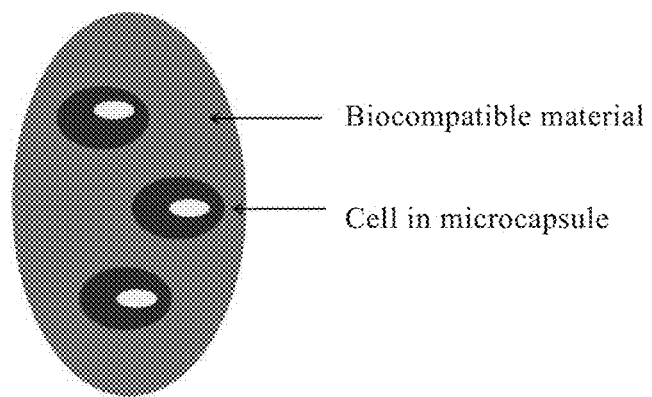
FIG. 1 schematically depicts an exemplary structure of a microcapsule of the present invention, comprising cells and a biocompatible material that encapsulates the cells; in a preferred embodiment, the cells may be homogeneously dispersed in the microcapsule or may be aggregated together and located inside the microcapsule.

In one aspect, the present application relates to an artificial tissue progenitor comprising a solid support and a plurality of microcapsules, wherein at least one microcapsule is attached to the solid support and the microcapsule comprises a cell and a biocompatible material encapsulating the cell. FIG. 1 schematically depicts an exemplary structure of microcapsule of the present invention. In a preferred embodiment, the cells may be homogeneously dispersed in a microcapsule or may be aggregated together and located inside the microcapsule.

In some preferred embodiments, the artificial tissue progenitor is a lumen (e.g., a circulatory lumen, digestive lumen, respiratory lumen, urinary lumen, or genital lumen) progenitor.

In some preferred embodiments, the lumen is a lumen containing epithelial cells (e.g., blood vessel, esophagus, trachea, stomach, bile duct, gut (including small intestine and large intestine, such as duodenum, jejunum, ileum, cecum (including appendix), ascending colon, right colic flexure, transverse colon, left colic flexure, descending colon, sigmoid colon, rectum), fallopian tube, vas deferens, ureter, bladder or lymphatic vessel).

In some preferred embodiments, the artificial tissue progenitor is tubular (e.g., a tube with or without an opening at side wall). A tubular artificial tissue progenitor without an opening at side wall can be used to replace a stenosed, occluded, dilated, damaged or deformed lumen, or to construct a lumen bypass (e.g., a blood vessel bypass). A tubular artificial tissue progenitor with an opening at side wall can be used to repair a broken lumen.

In some preferred embodiments, the artificial tissue progenitor is sheet-like (e.g., planar sheet or curved sheet). A sheet-like artificial tissue progenitor can be used to repair a broken lumen.

In some preferred embodiments, the plurality of the microcapsules constitutes one or more biological constructs.

In some preferred embodiments, the one or more biological constructs is attached to the solid support.

In some preferred embodiments, the microcapsules of the present invention have a stable structure under a physiological condition (e.g., at 4-37° C., e.g., at a pH of between 6 and 8, e.g., with fluid shear under a physiological condition). In some preferred embodiments, the microcapsules have a mechanical strength that avoids breakage of the microcapsules during aspiration or compression. In some preferred embodiments, the microcapsules provide mechanical protection for the encapsulated cell.

In some preferred embodiments of the invention, the microcapsules are capable of reducing or avoiding mechanical damage to the cells encapsulated in the microcapsules during handling (e.g., bio-printing). In some preferred embodiments, the microcapsules of the present invention are capable of reducing mechanical damage to the cells during bio-printing. For example, in some preferred embodiments, the microcapsules of the present invention are capable of reducing mechanical damage to the cells by at least 5%, 10%, 15%, 20%, 25%, 30%, 40%, 50%, 70%, 80% or 90%, as compared to directly bio-printing of cells using same bio-printer under same printing conditions. In some preferred embodiments, the microcapsules of the present invention are capable of maintaining the biological activity (e.g., proliferation, differentiation, migration, secretion and/or metabolism) of the cells within the microcapsules during bio-printing. In some preferred embodiments, at least 80%, 85%, 87.5%, 90%, 92.5%, 95% or 98% of cells within the microcapsule survive for at least 24 hours after bio-printing. In some preferred embodiments, at least 90% of the cells within the microcapsule survive for at least 3 hours, 6 hours, 12 hours, 1 day, 2 days, 4 days or 7 days after bio-printing. In some preferred embodiments, at least 80%, 85%, 87.5%, 90%, 92.5%, 95% or 98% of the cells within the microcapsule are capable of proliferating and/or differentiating after 24 hours of bio-printing. In some preferred embodiments, at least 80%, 85%, 87.5%, 90%, 92.5%, 95% or 98% of the cells within the microcapsules have normal metabolism after 24 hours of bio-printing. In some preferred embodiments, at least 80%, 85%, 87.5%, 90%, 92.5%, 95% or 98% of the cells within the microcapsule are capable of migrating after 24 hours of bio-printing. In some preferred embodiments, at least 80%, 85%, 87.5%, 90%, 92.5%, 95% or 98% of the cells within the microcapsule are capable of secreting after 24 hours of bio-printing.

In some preferred embodiments, the microcapsule provides a microenvironment for life activity of the cell. In some preferred embodiments, the microcapsule provides a spatial structure and microenvironment suitable for cell adhesion and extension such that the cells are capable of performing normal proliferation, differentiation, migration, secretion or metabolism within the structure. The microenvironment refers to an environment in which a cell grows, and contains elements including physical factors, such as spatial structure, mechanical strength, temperature, humidity, osmotic pressure and the like, chemical factors, such as pH, ionic strength and the like, and biological factors, including cells, cytokines and the like. These elements together form an environment for life activity of the cell and dynamically regulate the proliferation, differentiation, migration, secretion and metabolism of the cell that grows in this environment. In some preferred embodiments, the microcapsule is capable of providing a nutrient for the life activity of the cell.

In some embodiments of the present invention, the microcapsule is a bio-block.

The bio-block of the present invention comprises: a cell, a core enwrapping the cell, and a shell coating the core, wherein the core and the shell are each independently made from a biodegradable material. In some preferred embodiments of the present invention, the biodegradable material in the core and the shell is capable of reducing or avoiding mechanical damage to the cell in the bio-block during handling and is capable of providing a controlled release of a substance (e.g., a nutrient, an extracellular matrix, a cytokine, a pharmaceutically active ingredient, etc.) to promote cell activity and function (proliferation, differentiation, migration, secretion or metabolism) or to maintain cell stemness.

In some preferred embodiments, the core of the bio-block provides a spatial structure and microenvironment suitable for cell adhesion and extension such that the cell is capable of performing normal proliferation, differentiation, migration, secretion or metabolism within the structure. The microenvironment refers to an environment in which a cell grows and contains elements including physical factors, such as spatial structure, mechanical strength, temperature, humidity, osmotic pressure and the like, chemical factors, such as pH, ionic strength and the like, and biological factors, including cells, cytokines and the like. These elements together form an environment for life activity of the cell and dynamically regulate the proliferation, differentiation, migration, secretion and metabolism of the cell that grows in this environment. In some preferred embodiments, the core is capable of providing a microenvironment for the life activity of the cell, e.g., a spatial structure, a nutrient, and the like.

In some preferred embodiments, the shell of a bio-block provides mechanical protection for the enwrapped cells. In some preferred embodiments, the bio-block or the shell of the bio-block has a certain mechanical strength so that a three-dimensional packing can be achieved. In the present invention, it is particularly preferred that the bio-block and the shell thereof have a suitable mechanical protection property (e.g., suitable hardness and/or modulus of elasticity). On one hand, the cell in a bio-block is easily impaired or die due to damage caused by external pressure or shear force during handling. Therefore, if the hardness and/or modulus of elasticity of a bio-block and the shell thereof are too low, then the survival rate of the cell within the bio-block will be reduced significantly after manual handling, resulting in a limited application of the bio-block or a need of using a large quantity of cells. On the other and, if the hardness and/or modulus of elasticity of a bio-block and the shell thereof are too high, the extension and migration of the cell in the bio-block will be restricted, and the establishment of cell connection among the cells in different bio-blocks will be hindered, which is not conducive to the construction of an organic whole (e.g., an artificial tissue). Accordingly, a suitable mechanical protection property not only enables various handlings of the bio-blocks of the present invention to be carried out, but also facilitates extension and migration of cells and establishment of cell connection, and facilitates formation of an organic construct (e.g., an artificial tissue), thus is particularly preferred.

FIG. 2A to FIG. 2E schematically depict an exemplary structure of a bio-block of the present invention, which comprises a cell, a core encapsulating the cell, and a shell enclosing the core.

In particular, FIG. 2A schematically depicts a structure of a bio-block of the present invention, which comprises one core and one shell, wherein cells are encapsulated in the core, and the shell is located outside the core and encloses the core.

FIG. 2B schematically depicts a structure of a bio-block of the present invention, which comprises, in order from the inside to the outside, a core encapsulating cells, a first shell enclosing the core, and a second shell enclosing the first shell.

FIG. 2C schematically depicts a structure of a bio-block of the present invention, which comprises, in order from the inside to the outside, a first core encapsulating cells, a second core located outside the first core and encapsulating cells, and a first shell enclosing the first core and the second core.

FIG. 2D schematically depicts a structure of a bio-block of the present invention, which comprises, in order from the inside to the outside, a first core encapsulating cells, a second core located outside the first core and encapsulating cells, a first shell enclosing the first core and the second core, and a second shell enclosing the first shell.

FIG. 2E schematically depicts a structure of a bio-block of the present invention, which comprises, in order from the inside to the outside, a first core encapsulating cells, a first shell enclosing the first core, a second core encapsulating cells, and a second shell enclosing the second core.

For a detailed description of bio-blocks, please see, for example, Chinese Patent Application No. 201610211570.4 and PCT International Application No. PCT/CN2016/078678, each of which is incorporated herein by reference in its entirety.

The size of the microcapsule of the present invention can be selected according to actual needs without particular limitation. The size of a spherical microcapsule can usually be clearly defined by its diameter. Under strictly defined circumstances, the term "diameter" cannot be used to describe a non-spherical structure. However, in the present invention, the term "diameter" is used to describe the size of a non-spherical microcapsule. In this case, the term "diameter" means the diameter of a spherical microcapsule having the same volume as a non-spherical microcapsule. In other words, in the present invention, the diameter of a spherical microcapsule is used to describe the size of a non-spherical microcapsule having the same volume. Accordingly, in some preferred embodiments, the size (i.e., the diameter defined herein) of the microcapsules of the present invention may be 20-2000 µm, such as 30-1900 µm, 40-1800 µm, 50-1700 µm, 60-1600 µm, 70-1500 µm, 80-1400 µm, 90-1300 µm, 100-1200 µm, 200-1000 µm, 300-800 µm, 400-600 µm or 100-500 µm. In some preferred embodiments, the size (i.e., the diameter defined herein) of the microcapsules of the present invention may be 20-30, 30-50, 50-100, 100-150, 150-200, 200-250, 250-300, 300-350, 350-400, 400-450, 450-500, 500-600, 600-700, 700-800, 800-900, 900-1000, 1000-1500, 1500-2000, 20-50, 20-100, 100-200, 200-400, 500-600, 600-800, 800-1000 or 1000-2000 µm. In some preferred embodiments, the size (i.e., the diameter as defined herein) of the microcapsules of the invention is at least 20, 30, 50, 100, 120, 150, 200, 250, 300, 350, 400, 450, 500, 600, 700, 800, 900, 1000, 1500 or 2000 µm.

The shape of the microcapsule of the present invention may be selected according to actual needs without particular limitation. For example, the microcapsule of the present invention may be spherical or of desired shape (e.g., cube, rectangular prism, hexagonal prism, cylinder, or irregular shape). For example, some shapes (e.g., sphere, cube, rectangular prism, hexagonal prism) may be used to achieve a close packing of microcapsules in a construct.

In some preferred embodiments, the microcapsule of the present invention is solid or semi-solid. In some preferred embodiments, the microcapsule of the present invention is in a gel state. For example, the core and/or the shell of the microcapsule of the present invention may be in a gel state. In some preferred embodiments, the microcapsule of the invention comprises a hydrogel. In some preferred embodiments, the hydrogel includes alginate, agarose, gelatin, chitosan, or other water-soluble or hydrophilic polymers.

In some preferred embodiments, the microcapsules of the invention are present in the form of a mixture. In such embodiments, a microcapsule can be contacted or fused with another microcapsule in the mixture. In some preferred embodiments, the microcapsules of the present invention are an isolated microcapsules. For example, in some embodiments, a microcapsule is not in direct contact with other microcapsule. In some preferred embodiments, the isolated microcapsules of the present invention are provided in a container.

The microcapsule of the present invention may be prepared by a variety of methods. For example, in some preferred embodiments, the microcapsule of the present invention may be prepared by using a method for making a microsphere, for example, by using an encapsulator for preparation. In some preferred embodiments, the microcapsule of the present invention is prepared under aseptic conditions. In some preferred embodiments, the microcapsule of the present invention is prepared in a GMP workshop. In some preferred embodiments, the microcapsule of the present invention is prepared just prior to use. In some preferred embodiments, the microcapsule of the invention is stored at 4° C. after preparation, for example, for 3 hours, 6 hours, 12 hours, 1 day, 2 days or 3 days.

The type of cells contained in the microcapsules of the present invention may be selected according to actual needs without particular limitation. In some preferred embodiments, the microcapsules contain epithelial cells, such as endothelial cells (e.g., vascular endothelial cells), smooth muscle cells (e.g., vascular smooth muscle cells), and/or undifferentiated cells.

In some preferred embodiments, the cells in the microcapsules are undifferentiated cells, such as stem cells (e.g., adipose-derived mesenchymal stem cells, bone marrow mesenchymal stem cells, induced pluripotent stem cells or embryonic stem cells).

In some preferred embodiments, the undifferentiated cells are capable of differentiating into epithelial cells (e.g., endothelial cells) and/or smooth muscle cells.

In some preferred embodiments, the undifferentiated cells are selected from one or more of stem cells (e.g., adipose-derived mesenchymal stem cells, bone marrow mesenchymal stem cells, induced pluripotent stem cells or embryonic stem cells) and progenitor cells (e.g., endothelial progenitor cells).

The source of the cells contained in the microcapsules of the present invention may be selected according to actual needs without particular limitation. In some preferred embodiments, the cells are obtained from an animal, for example a mammal, e.g., a human, an ape, a monkey, a gorilla, a cattle, a pig, a dog, a sheep or a goat.

In some preferred embodiments, the cells are derived from a tissue selected from the group consisting of connective tissue (e.g., loose connective tissue, dense connective tissue, elastic tissue, reticular connective tissue and adipose tissue), muscle tissue (e.g., skeletal muscle, smooth muscle and myocardium), genitourinary tissue, gastrointestinal tissue, lung tissue, bone tissue, nervous tissue and epithelial tissue (e.g., simple epithelium and stratified epithelium), endoderm-derived tissue, mesoderm-derived tissue and ectoderm-derived tissue.

The number of cells contained in the microcapsules of the present invention may be selected according to actual needs without any particular limitation. For example, the core of a microcapsule of the present invention may comprise $1-10^6$ cells, for example 10-900, 20-800, 30-700, 40-600, 50-500, 60-400, 70-300, 80-200, 10-100, $10-10^3$, $10-10^4$, $10-10^5$ or $10-10^6$ cells. In some preferred embodiments of the present invention, a microcapsule of the present invention may comprises at least 1, 2, 4, 6, 8, 10, 15, 20, 25, 30, 40, 50, 60, 70, 80, 90, 100, 150, 200, 300, 400, 500, 600, 700, 800, 900, 1000, 2000, 3000, 4000, 5000, 6000, 7000, 8000, 9000, $10^4$, $2\times10^4$, $3\times10^4$, $4\times10^4$, $5\times10^4$, $6\times10^4$, $7\times10^4$, $8\times10^4$, $9\times10^4$, $10^5$, $2\times10^5$, $3\times10^5$, $4\times10^5$, $5\times10^5$, $6\times10^5$, $7\times10^5$, $8\times10^5$, $9\times10^5$ or $10^6$ cells. In some preferred embodiments of the present invention, a microcapsule of the present invention may comprises 1-2, 2-4, 4-6, 6-8, 8-10, 10-15, 15-20, 20-25, 25-30, 30-40, 40-50, 50-60, 60-70, 70-80, 80-90, 90-100, 100-150, 150-200, 200-300, 300-400, 400-500, 500-1000, 1000-2000, 2000-3000, 3000-4000, 4000-5000, $5000-10^4$, $10^4-2\times10^4$, $2\times10^4-3\times10^4$, $3\times10^4-4\times10^4$, $4\times10^4-5\times10^4$, $5\times10^4-10^5$, $10^5-2\times10^5$, $2\times10^5-3\times10^5$, $3\times10^5-4\times10^5$, $4\times10^5-5\times10^5$, $5\times10^5-10^6$ 1-10, 2-10, 2-5, 5-10, 10-20, 20-30, 30-50, 2-25, 25-50, 2-50, 50-100, 100-200, 50-250, 250-500, 500-2000, 2-100, 2-500 or 2-2000 cells.

In some preferred embodiments, in addition to epithelial cells (e.g., endothelial cells), smooth muscle cells and/or undifferentiated cells as described above, the cells encapsulated in a microcapsule further include additional cells. In some preferred embodiments, the additional cells are derived from a tissue selected from the group consisting of connective tissue (e.g., loose connective tissue, dense connective tissue, elastic tissue, reticular connective tissue and adipose tissue), muscle tissue (e.g., skeletal muscle, smooth muscle and myocardium), genitourinary tissue, gastrointestinal tissue, lung tissue, bone tissue, neural tissue and epithelial tissue (e.g., simple epithelium and stratified epithelium), endoderm-derived tissue, mesoderm-derived tissue and ectoderm-derived tissue. In some preferred embodiments, the additional cells are selected from a group consisting of muscle cells (e.g., skeletal muscle cells, cardiomyocytes, smooth muscle cells and myoblasts), connective tissue cells (e.g., osteocytes, chondrocytes, fibroblasts and cells differentiate to osteoblasts, chondrocytes or lymphoid tissue), myeloid cells, skin cells, epithelial cells, breast cells, vascular cells, blood cells, lymphocytes, neural cells, Schwann cells, gastrointestinal cells, hepatocytes, pancreatic cells, lung cells, tracheal cells, corneal cells, urogenital cells, renal cells, adipocytes, parenchymal cells, pericytes, mesothelial cells, stromal cells, endoderm-derived cells, mesodermal-derived cells, ectoderm-derived cells, cancer-derived cells, cell lines and any combination thereof.

In some preferred embodiments, a microcapsule of the present invention comprises a cell and a core encapsulating the cell. In some preferred embodiments, the core provides a microenvironment for life activity of the cell. In some preferred embodiments, the microcapsule provides a spatial structure and microenvironment suitable for cell adhesion and extension such that the cell is capable of performing normal proliferation, differentiation, migration, secretion or metabolism within the structure or maintaining stemness. The microenvironment refers to an environment in which a cell grows and contains elements including physical factors, such as spatial structure, mechanical strength, temperature, humidity, osmotic pressure and the like, chemical factors, such as pH, ionic strength and the like, and biological factors, including cells, cytokines and the like. These elements together form an environment for life activity of the cell and dynamically regulate the proliferation, differentiation, migration, secretion and metabolism of the cell that grows in this environment or maintain cell stemness. In some preferred embodiments, the core is capable of providing a nutrient for the life activity of the cell.

In some preferred embodiments, the core is made from a biocompatible material.

In some preferred embodiments, the microcapsule further comprises a shell enclosing the core.

In some preferred embodiments, the shell of a microcapsule provides mechanical protection for the encapsulated cell. In some preferred embodiments, the microcapsule or the shell of a microcapsule has a certain mechanical strength so that a three-dimensional packing can be achieved. In the present invention, it is particularly preferred that the microcapsule and the shell thereof have suitable a mechanical protection property (e.g., suitable hardness and/or modulus of elasticity). On one hand, the cell in a microcapsule is easily impaired or die due to damage caused by external pressure or shear force during handling (e.g., during 3D printing). Therefore, if the hardness and/or modulus of elasticity of the microcapsule and the shell thereof are too low, then the survival rate of cell within the microcapsule will be reduced significantly after manual handling, resulting in a limited application of the microcapsule or a need of using a large quantity of cells. On the other and, if the hardness and/or modulus of elasticity of the microcapsule and the shell thereof are too high, the extension and migration of the cells in the microcapsule will be restricted, the establishment of cell connection among the cells in different bio-blocks will be hindered, which is not conducive to the construction of an organic whole (e.g., an artificial tissue). Accordingly, a suitable mechanical protection property not only enables various procedures (e.g., 3D bio-printing, or precise arrangement of microcapsules, etc.) of the microcapsules of the present invention to be carried out, but also facilitates extension and migration of cells and establishment of cell connection, and facilitates formation of an organic construct (e.g., an artificial tissue), thus is particularly preferred.

In some preferred embodiments, the core and/or the shell of a microcapsule of the present invention are each optionally treated (for example, treatment with a core fixing solution or a shell fixing solution, to improve the mechanical property of the core or the shell).

In some preferred embodiments, the microcapsule, the core of the microcapsule or the shell of the microcapsule each independently has a hardness of about 0.01, 0.02, 0.03, 0.04, 0.05, 0.06, 0.07, 0.08, 0.09, 0.1, 0.15, 0.2, 0.3, or 0.4 GPa. In some preferred embodiments, the microcapsule, the core of the microcapsule or the shell of the microcapsule each independently has a hardness of 0.01-0.02, 0.02-0.03, 0.03-0.04, 0.04-0.05, 0.05-0.06, 0.06-0.07, 0.07-0.08, 0.08-0.09, 0.09-0.1, 0.1-0.15, 0.15-0.2, 0.2-0.3, 0.3-0.4, 0.01-0.4, 0.01-0.05, 0.05-0.1, 0.1-0.2, 0.2-0.4, 0.05-0.15 or 0.06-0.1 GPa. In some preferred embodiments, the microcapsule, the core of the microcapsule or the shell of the microcapsule each independently has a hardness of 0.01-0.1 GPa or 0.01-0.4 GPa. In some preferred embodiments, the microcapsule, the core of the microcapsule or the shell of the microcapsule has a hardness of about 0.083 GPa. In some preferred embodiments, the microcapsule, the core of the microcapsule or the shell of the microcapsule each independently has a modulus of elasticity of about 0.01, 0.05, 0.1, 0.5, 0.8, 1, 1.2, 1.4, 1.6, 1.8, 2, 2.4, 2.8, 3.2, 4, 10, 20, 30, 40, 50, 80 or 100 MPa. In some preferred embodiments, the microcapsule, the core of the microcapsule or the shell of the microcapsule each independently has a modulus of elasticity of 0.01-0.05, 0.05-0.1, 0.1-0.5, 0.5-0.8, 0.8-1, 1-1.2, 1.2-1.4, 1.4-1.6, 1.6-1.8, 1.8-2, 2-2.4, 2.4-2.8, 2.8-3.2, 3.2-4, 4-10, 10-20, 20-30, 30-40, 40-50, 50-80, 80-100, 0.5-4, 0.5-1, 1-1.5, 1.5-2, 2-3, 0.8-1.6, 1.4-2.4, 0.8-3.2, 0.01-100, 1-100, 10-100 or 0.5-50 MPa. In some preferred embodiments, the microcapsule, the core of the microcapsule or the shell of the microcapsule each independently has a modulus of elasticity of 0.01-1, 0.01-10 or 0.01-100 MPa. The mechanical protection (e.g., hardness and modulus of elasticity) of the core or the shell may be controlled by formulating the components and/or their amounts in the core or in the shell.

In some preferred embodiments, the shell can also provide a microenvironment, e.g., a nutrient, for life activity of the cell. In some preferred embodiments, the shell is made from a biocompatible material.

In some preferred embodiments, the biocompatible materials used to make a core and a shell may be the same or different. However, particularly preferably, the core and the shell have different compositions depending on an expected purpose thereof. Without being limited by theory, it is generally accepted that the shell provides major mechanical protection and that the core provides major nutrients and microenvironment needed for life activity of the cell. Accordingly, in some preferred embodiments, the core has more nutrient as compared with the shell. In some preferred embodiments, the shell has a lower degradation rate and a higher hardness and/or modulus of elasticity as compared with the core. In some preferred embodiments, the shell comprises no cell.

In some preferred embodiments, the core and the shell respectively contain the same biocompatible materials at different weight ratios. In other words, the core and the shell may be made from a same biocompatible material but contain a biodegradable material in different weight ratios.

In some preferred embodiments, the shell is permeable. For example, the shell is permeable to water, oxygen, and a nutrient (saccharide such as glucose, fats, protein, amino acid, short peptide, mineral, vitamin, cytokine, nucleotides and the like).

It is believed that the use of a semipermeable (i.e., selectively permeable) shell may be advantageous because it enables a nutrient such as water, oxygen, glucose, mineral or amino acid to go through the shell into the core and to be provided to the cell, and is capable of blocking the entry of a substance (e.g., an antibody protein from the immune system of a host) that is detrimental to the cell into the core. However, the use of a permeable shell in the microcapsules of the present invention is preferred and advantageous. In particular, the permeable shell enables various nutrients (including macromolecular nutrients and small molecular nutrients such as glucose, fat, protein, amino acid, short peptide, mineral, vitamin, cytokine, nucleotide, etc.) to exchange much easily and smoothly, avoiding that cells in certain local areas cannot get enough nutrients. For example, when the microcapsules of the present invention are used to construct a large-sized artificial tissue, the permeable shell will be able to facilitate exchange of various nutrients and promote the cells in the microcapsules inside/in core area of the artificial tissue to get adequate nutrients. In addition, the permeable shell facilitates signal transduction and establishment of cell connection among cells in different microcapsules. In particular, cells secrete a variety of substances (including certain components of the extracellular matrix and various signaling molecules) during growth to carry out signal transduction and/or substance exchange with adjacent or even distant cells, affecting or regulating the life activity of the cells themselves and of adjacent or even distant cells. Thus, if a selectively permeable shell is used, signal transduction and/or substance exchange among cells may be affected/hindered, for example, certain macromolecular signaling substances (e.g., cytokine proteins) secreted by cells may not go through the shell, which may hinder the signal transduction and the establishment of cell connection among cells in different microcapsules, which is not conducive to the construction of an organic whole (e.g., an artificial tissue). Therefore, the use of a permeable shell is preferred for the microcapsules of the present invention. In the present invention, the expression "permeable shell" refers to a shell through which various small molecules and macromolecular substances (e.g., proteins) are able to freely pass. For example, in some preferred embodiments, the shell is permeable to a molecule having a molecular weight of below 5000 kDa. For example, in some embodiments, the shell is permeable to a molecule having a molecular weight of less than 200 kDa or a molecular weight of from 200 kDa to 300 kDa, from 300 kDa to 400 kDa, from 400 kDa to 500 kDa, from 500 kDa to 800 kDa, from 800 kDa to 1000 kDa, from 1000 kDa to 1500 kDa, from 1500 kDa to 2000 kDa, from 2000 kDa to 3000 kDa, from 3000 kDa to 4000 kDa or from 4000 kDa to 5000 kDa. In some embodiments, the shell is permeable to an immunoglobulin (e.g., IgG, IgM, IgA, IgD, IgE).

In some preferred embodiments, the shell has a channel or a hole for exchange of substances inside and outside a microcapsule. In some preferred embodiments, a nutrient (saccharide such as glucose, fat, protein, amino acid, short peptide, mineral, vitamin, cytokine, nucleotide etc.) diffuse into the microcapsule via the channel or hole. In some preferred embodiments, the channel has a diameter of at least 10 nm, 20 nm, 50 nm, 100 nm, 150 nm, 200 nm, 250 nm, 300 nm, 350 nm, 400 nm or 500 nm. In some preferred embodiments, the diameter of the channel is, for example, of 1 nm-5 µm, 10 nm-2 µm, 100 nm-1 µm, 200-800 nm, or the like. In some preferred embodiments, the hole has a diameter of at least 100 nm, 200 nm, 400 nm, 600 nm, 800 nm, 1000 nm, 1500 nm, 2000 nm, 4000 nm or 5000 nm.

The thickness of the shell of a microcapsule of the present invention may be selected according to actual needs without particular limitation. For example, the shell of a microcapsule of the present invention may have a thickness of 1 to 20 µm, for example 5 to 15 µm, for example 8 to 12 µm. In certain embodiments, the shell of a microcapsule of the present invention may have a thickness of about 0.1 µm, 0.5 µm, 1 µm, 2 µm, 5 µm, 10 µm, 15 µm, 20 µm, 25 µm, 30 µm or 50 µm. In some preferred embodiments, the shell of a microcapsule of the present invention may have a thickness of 0.1-0.5 µm, 0.5-1 µm, 1-2 µm, 2-5 µm, 5-10 µm, 10-15 µm, 15-20 µm, 20-25 µm, 25-30 µm, 30-50 µm, 50-100 µm, 100-200 µm, 200-300 µm, 300-400 µm, 400-500 µm, 0.1-1 µm, 1-5 µm, 1-10 µm, 5-10 µm, 10-20 µm, 10-30 µm, 5-20 µm or 1-20 µm.

In some preferred embodiments, the shell of a microcapsule of the present invention contains no cell.

In some preferred embodiments, the biocompatible material of the present invention includes a biodegradable material.

In the present invention, the use of a biodegradable material in the preparation of a microcapsule is particularly preferred. In particular, using a non-degradable material is disadvantageous for the use of a microcapsule in the preparation of an artificial tissue progenitor. This is because, on one hand, the non-degradable material will be retained in an obtained artificial tissue, thus limiting the use of the artificial tissue; on the other hand, the non-degradable material will hinder the establishment of cell connection among cells in different microcapsules, which is not conducive to the construction of an organic whole (for example, an artificial tissue). Accordingly, the use of a biodegradable material in a shell is particularly advantageous and preferred for the use of a microcapsule in the preparation of an artificial tissue progenitor.

In some preferred embodiment, the biodegradable material is a biomaterial that is degradable.

In embodiments of the present invention, a biodegradable material used for the preparation of a microcapsule may be a naturally occurring material (e.g., a naturally occurring biodegradable materials derived from an animal or a plant, such as collagen, fibrin, chitosan, alginate, starch, hyaluronic acid, laminin, agarose, gelatin, glucose, and any combination thereof), a synthetic material, a material produced by recombination, a modified material or any combination thereof.

In some preferred embodiments, the biodegradable material used for the preparation of a microcapsule is a naturally occurring biodegradable material. In some preferred embodiments, the naturally occurring biodegradable material is selected from the group consisting of collagen, fibrin, chitosan, alginate (e.g., sodium alginate or calcium alginate), starch, hyaluronic acid, laminin, agarose, gelatin, dextran, chitin, cellulose (e.g., bacterial cellulose), silk fibroin, chondroitin sulfate, heparin, fibrinogen, fibronectin, mucopolysaccharide, mucin and any combination thereof. In some preferred embodiments, the biodegradable material used for the preparation of a microcapsule is a modified biodegradable material, such as a modified alginate, for example, an oxidized alginate (e.g., oxidized sodium alginate), a modified gelatin (e.g., a modified gelatin cross-linked with dialdehyde starch (DAS)), a modified cellulose (e.g., carboxymethyl cellulose, oxidized regenerated cellulose), and any combination thereof.

In some preferred embodiments, a biodegradable material used for the preparation of a microcapsule is a synthetic biodegradable material, such as polyphosphazene, polyacrylic acid and a derivative thereof (e.g., polymethacrylic acid, a copolymer of acrylic acid and methacrylic acid), polylactic acid (PLA), polyglycolic acid (PGA), poly(lactic acid-co-glycolic acid) (PLGA), polyorthoester (POE), polycaprolactone (PCL), polyhydroxybutyrate (PHB), polyamine acid (e.g., polylysine), degradable polyurethane (e.g., starch-modified polyurethane), polyhydroxyalkanoate (PHAs), polyhydroxyvalerate (PHV), polybutylene succinate (PBS), polyvinyl alcohol, polydioxanone, poly(1,4-dioxan-2-one), poly(p-dioxanone), polybutylene carbonate or any combination thereof.

In some preferred embodiments, the biodegradable material used for the preparation of a microcapsule can be degraded by an enzyme (e.g., an enzyme secreted by a cell). Different biodegradable materials vary greatly in degradation rate thereof, and the degradation times thereof can range from one month to several years. In the present invention, however, it is particularly preferred that a biodegradable material used for the preparation of a shell is degraded in no more than 1 month, for example, no more than 30 days, no more than 25 days, no more than 20 days, no more than 15 days, no more than 10 days, no more than 5 days, no more than 4 days, no more than 3 days, no more than 2 days or no more than 1 day. For example, a biodegradable material used for the preparation of a microcapsule may be degraded in 1-2 days, 2-3 days, 3-4 days, 4-5 days, 5-10 days, 10-15 days, 15-20 days, 20-25 days or 25-30 days. It is particularly preferred that a biodegradable material used for the preparation of a microcapsule is degraded in less than 10 days. The degradation rate of a biodegradable material is closely related to molecular composition, molecular weight and molecular arrangement (e.g., linear or branched) thereof. In general, the higher the molecular weight and the closer the molecular arrangement, the longer the degradation time. Therefore, the degradation rate of a microcapsule can be controlled by formulating the components and/or their contents of a shell. For example, in order to arrive at a rapid degradation rate, a biodegradable material at a low content (e.g., less than 0.5%, less than 1%, less than 2%, less than 3%, less than 4% or less than 5%), a biodegradable material having a low molecular weight (e.g., less than 500 Da, less than 1 kDa, less than 2 kDa, less than 3 kDa, less than 5 kDa or less than 10 kDa), and/or a biodegradable material with a loose molecular arrangement, may be used; in order to arrive at a slow degradation rate, a biodegradable material at a high content (e.g., higher than 0.5%, higher than 1%, higher than 2%, higher than 3%, higher than 4% or higher than 5%), a biodegradable material having a great molecular weight (e.g., greater than 500 Da, greater than 1 kDa, greater than 2 kDa, greater than 3 kDa, greater than 5 kDa or greater than 10 kDa), and/or a biodegradable material with a close molecular arrangement may be used. In addition, the degradation rate of a biodegradable material can also be adjusted by changing the structure of the microcapsule (for example, multi-layer encapsulation, porous surface, porosity, specific surface area, etc.). Moreover, the degradation rate of a biodegradable material can also be adjusted by changing the polymerization manner for synthesizing the material and a ratio of copolymers, or crosslinking the material. Furthermore, the degradation rate of a biodegradable material used for the preparation of the microcapsule may also be affected by the life activity of the cell.

In the present invention, it is particularly preferred that the cell within a microcapsule are capable of growing, extending, proliferating, migrating and establishing cell connection with a cell within another microcapsule to form an organic construct (e.g., an artificial tissue). Accordingly, in some preferred embodiments, the microcapsule is degraded in a relatively short period of time (e.g., no more than 30 days, e.g., no more than 10 days) to promote establishment of cell connection among cells in different microcapsules, thereby preventing establishment of cell connection among cells in different microcapsules from being hindered or affected. In some preferred embodiments, the microcapsules are degraded in no more than 30 days, no more than 25 days, no more than 20 days, no more than 15 days, no more than 10 days, no more than 5 days, no more than 4 days, no more than 3 days, no more than 2 days or no more than 1 day. For example, the microcapsules are able to be degraded in 1-2 days, 2-3 days, 3-4 days, 4-5 days, 5-10 days, 10-15 days, 15-20 days, 20-25 days or 25-30 days.

Various biodegradable materials are known to a person skilled in the art and their degradation properties have been extensively studied, please see, for example, Alexander D. Augst, Hyun Joon Kong, David J. Mooney, "Alginate Hydrogels as Biomaterials", Macromol. Biosci. 2006, 6, 623-633, which is incorporated herein by reference.

In some preferred embodiments, degradation of a microcapsule provides a microenvironment (e.g., a nutrient) that maintains or promotes the life activity of a cell. In some preferred embodiments, degradation product of a shell is a small molecule compound such as an organic acid, a monosaccharide (e.g., glucose), an oligosaccharide, an amino acids, a lipid and the like. Such degradation product may be involved in metabolic activity of the cell and is used for the synthesis of an extracellular matrix or for conversion of energy required for activity.

In some preferred embodiments, a biodegradable material used for the preparation of a microcapsule and degradation product thereof are non-toxic to a cell, and/or non-immunogenic to a host.

In some preferred embodiments, a biodegradable material used for the preparation of a microcapsule contains an extracellular matrix or an analogue thereof (e.g., elastin). The use of an extracellular matrix or analogue thereof (e.g., elastin) is capable of providing an advantageous microenvironment similar to the microenvironment in vivo for the life activity of the cell within the microcapsule (in particular, for the growth, adhesion and expansion of the cell, and the establishment of cell connection), which is therefore preferred.

In some preferred embodiments, a biodegradable material used for the preparation of a microcapsule is selected from the group consisting of collagen (e.g., type I, type II or type III collagen), fibrin, chitosan, alginate (e.g., sodium alginate or calcium alginate), an oxidized alginate (e.g., oxidized sodium alginate), starch, hyaluronic acid, laminin, elastin, gelatin, dextran, polyamine acid (e.g., polylysine), agarose and any combination thereof. In some preferred embodiments, the microcapsule comprise an alginate (e.g., sodium alginate or calcium alginate), for example, the microcapsule comprises calcium alginate and gelatin, optionally further comprises elastin.

In some preferred embodiments, the microcapsule comprises an alginate (e.g., sodium alginate or calcium alginate) and gelatin.

In some preferred embodiments, the microcapsule comprises an alginate (e.g., sodium alginate or calcium alginate), for example, the microcapsule comprises calcium alginate and gelatin, and optionally further comprises elastin. In some preferred embodiments, the microcapsule comprises an oxidized alginate (e.g., oxidized sodium alginate). In some preferred embodiments, the microcapsule comprises an alginate (e.g., sodium alginate or calcium alginate) and agarose.

In some preferred embodiments, an oxidized alginate (e.g., oxidized sodium alginate and oxidized calcium alginate) may be used for the preparation of a microcapsule, and the degradation rate thereof may be adjusted by controlling oxidation degree of the alginate, whereby the degradation rate of the microcapsule matches with the growth rate of the cell encapsulated therein.

In some preferred embodiments, the microcapsule comprises a core and one or more shells (e.g., 2, 3, 4, or 5).

In some preferred embodiments, the biodegradable material used for the preparation of a core of a microcapsule is selected from the group consisting of collagen (e.g., type I, type II or type III collagen), fibrin, chitosan, alginate (e.g., sodium alginate or calcium alginate), hyaluronic acid, agarose, gelatin, starch, dextran, polyphosphazene, polyacrylic acid and a derivative thereof, polylactic acid (PLA), polyamino acid (e.g., polylysine), biodegradable polyurethane and any combination thereof.

In some preferred embodiments, the biodegradable material used for the preparation of a shell of a microcapsule is selected from the group consisting of alginate (e.g., sodium alginate or calcium alginate), elastin, polyamino acid (e.g., polylysine), oxidized alginate, gelatin, chitosan and any combination thereof.

In some preferred embodiments, the biodegradable material used for the preparation of a core of a microcapsule includes collagen (e.g., type I, type II or type III collagen).

In some preferred embodiments, the biodegradable material used for the preparation of a shell of a microcapsule is selected from polyamino acid (e.g., polylysine) and alginate (e.g., sodium alginate or calcium alginate).

In some preferred embodiments, the microcapsule further comprises an additional agent, such as, a nutrient, an extracellular matrix, a cytokine, and/or a pharmaceutically active ingredient.

In some preferred embodiments, the additional agent is capable of modulating (e.g., promoting) the proliferation, differentiation, migration, secretion and/or metabolism of the cell, or the additional agent is capable of maintaining the stemness of the cell. In some preferred embodiments, the microcapsule comprises at least one (e.g., 1, 2, 3, 4, 5 or more) additional agent that is capable of modulating (e.g., promoting) proliferation, differentiation, migration, secretion and/or metabolism of the cell or additional agent that is capable of maintaining the stemness of the cell. In some preferred embodiments, the microcapsule is capable of releasing the additional agent in a controlled manner.

In some preferred embodiments, the nutrient includes, but is not limited to, a nucleotide, an amino acid, a polypeptide, a carbohydrate (e.g., a monosaccharide, an oligosaccharide or a polysaccharide), a lipid, a vitamin and the like.

In some preferred embodiments, the extracellular matrix is selected from the group consisting of polysaccharides such as glycosaminoglycan and proteoglycan; structural proteins such as collagen and elastin; adhesion proteins such as fibronectin and laminin.

In some preferred embodiments, the cytokine may be a cytokine for regulating and controlling the proliferation, differentiation, migration, secretion and/or metabolism of a cell, including but not limited to:
  a cytokine associated with cell growth, such as insulin, insulin-like growth factor (e.g., IGF-I, IGF-II), transforming growth factor (e.g., TGFα and TGFβ), vascular endothelial growth factor, epidermal growth factor, fibroblast growth factor, platelet-derived growth factor, osteosarcoma-derived growth factor, growth hormone release inhibiting factor, nerve growth factor, interleukin (e.g., IL-1, IL-11, IL-3), erythropoietin, colony stimulating factor, cortisol, thyroxine, or any combination thereof;
  a cytokine associated with cell differentiation such as Oct3/4, Sox2, Klf4, c-Myc, GATA4, TSP1, sodium beta-glycerophosphate, dexamethasone, vitamin C, insulin, IBMX, indomethacin, platelet-derived growth factor BB (PDGF-BB) 5-azacytidine, or any combination thereof;
  a cytokine associated with cell migration such as cyclic adenosine monophosphate, phosphatidylinositol triphosphate, stromal cell-derived factor-1, N-cadherin, nuclear factor κB, osteonectin, thromboxane A2, Ras, or any combination thereof; and/or
  a cytokine associated with cell metabolism such as insulin growth factor 1, TRIP-Br2, DKK-1, sRANKL, OPG, TRACP-5b, ALP, SIRT1 (2-7), PGC-1α, PGC-1β, OPG, IL-3, IL-4, IL-6, TGF-β, PGE2, G-CSF, TNF-α, or any combination thereof.

In some preferred embodiments, the pharmaceutically active ingredient is an agent that is capable of modulating (e.g., promoting) the proliferation, differentiation, migration, secretion and/or metabolism of a cell, or an agent is capable of maintaining the stemness of a cell. In some preferred embodiments, the pharmaceutically active ingredient is selected from the group consisting of rhIL-2, rhIL-11, rhEPO, IFN-α, IFN-β, IFN-γ, G-CSF, GM-CSF, rHuEPO, sTNF-R1 and rhTNF-α.

In some preferred embodiments, the microcapsule comprises a cytokine that is capable of inducing differentiation of undifferentiated cells into a smooth muscle cells or an endothelial cell, such as TGF-α1, PDGF-BB, VEGF or b-FGF.

In some preferred embodiments, the microcapsule comprises an adipose-derived mesenchymal stem cell and a core that encapsulates the adipose-derived mesenchymal stem cell, preferably, the core is made from a biodegradable material; preferably, the core provides a microenvironment that maintains the stemness of the adipose-derived mesenchymal stem cell (for example, the core comprises an additional agent that maintains the stemness of the adipose-derived mesenchymal stem cell); preferably, the core provides a microenvironment for inducing differentiation of the adipose-derived mesenchymal stem cell into an endothelial cell or a smooth muscle cell (for example, the core comprises an inducing factor for inducing differentiation of the adipose-derived mesenchymal stem cell into an endothelial cell or a smooth muscle cell). In some preferred embodiments, the inducing factor that induces differentiation of the adipose-derived mesenchymal stem cell into a smooth muscle cell is selected from the group consisting of TGF-α1 and PDGF-BB. In some preferred embodiments, the inducing factor that induces differentiation of an adipose-derived mesenchymal stem cell into an endothelial cell is selected from the group consisting of VEGF and b-FGF.

In some preferred embodiments, the microcapsule comprises an adipose-derived mesenchymal stem cell, a core that encapsulates the adipose-derived mesenchymal stem cell, and a shell that encloses the core; preferably, the core and the shell are each independently made from a biodegradable material; preferably, the core provides a microenvironment that maintains the stemness of the adipose-derived mesenchymal stem cell (for example, the core comprises an additional agent that maintains the stemness of the adipose-derived mesenchymal stem cell); preferably, the core provides a microenvironment for inducing differentiation of the adipose-derived mesenchymal stem cell into an endothelial cell or a smooth muscle cell (for example, the core comprises an inducing factor for inducing differentiation of the adipose-derived mesenchymal stem cell into an endothelial cell or a smooth muscle cell). In some preferred embodiments, the shell of such a microcapsule also provides a microenvironment for inducing differentiation of the adipose-derived mesenchymal stem cell into an endothelial cell or a smooth muscle cell (for example, the shell comprises an inducing factor for inducing differentiation of the adipose-derived mesenchymal stem cell into an endothelial cell or a smooth muscle cell). In some preferred embodiments, the inducing factor that induces differentiation of the adipose-derived mesenchymal stem cell into a smooth muscle cell is selected from the group consisting of TGF-α1 and PDGF-BB. In some preferred embodiments, the inducing factor that induces differentiation of the adipose-derived mesenchymal stem cell into an endothelial cell is selected from the group consisting of VEGF and b-FGF.

In the artificial tissue progenitor of the present invention, preferably, the solid support is made from a biocompatible material.

In some preferred embodiments, the biocompatible material includes a biodegradable material. In the present invention, a biodegradable material is used for the preparation of a solid support so as to allow for the gradual degradation of the solid support during the continuous growth of an artificial tissue progenitor after it is implanted in the body of a subject, eventually resulting in full fusion of the artificial tissue with autologous tissue of the subject together.

In some preferred embodiments, the biodegradable material is a biomaterial that is degradable.

In some preferred embodiments, the biodegradable material may be a naturally occurring biodegradable material (e.g., collagen, gelatin, chitosan, polyhydroxybutyrate (PHB), chitin, alginate (e.g., sodium alginate), starch-based biomaterial (e.g., polysaccharide starch), cellulose (e.g., bacterial cellulose), silk protein or any combination thereof).

In some preferred embodiments, the naturally occurring biodegradable material is a starch.

In some preferred embodiments, the biodegradable material is a modified biodegradable material, for example, a modified alginate, such as an oxidized alginate (e.g., oxidized sodium alginate), a modified gelatin (e.g., a modified gelatin cross-linked with dialdehyde starch (DAS)), a modified cellulose (e.g., carboxymethyl cellulose, oxidized regenerated cellulose), or any combination thereof.

In some preferred embodiments, the biodegradable material is a synthetic biodegradable material, for example, aliphatic polyester (e.g., polylactic acid (PLA), polycaprolactone (PCL), polyhydroxyalkanoate (PHAs), polyhydroxyvalerates (PHV), polyhydroxybutyrate (PHB), polybutylene succinate (PBS)), polyglycolic acid (PGA), poly (lactic acid-co-glycolic acid) (PLGA), polyorthoester (POE), degradable polyurethane (e.g., starch-modified polyurethane), polyvinyl alcohol, polydioxanone, poly(1,4-dioxan-2-one), poly(p-dioxanone), polybutylene carbonate, polyphosphazene or any combination thereof.

In some preferred embodiments, the synthetic biodegradable material is selected from the group consisting of polycaprolactone (PCL), polylactic acid (PLA), poly(lactic acid-co-glycolic acid) (PLGA), polyglycolic acid (PGA) and degradable polyurethane.

In some preferred embodiments, the biodegradable material can be degraded by an enzyme (e.g., an enzyme secreted by a cell).

In some preferred embodiments, the biodegradable material has an in vivo degradation time of 1-12 months.

In some preferred embodiments, the biocompatible material further comprises a non-biodegradable material (e.g., nylon, terylene, polypropylene, polyethylene, polytetrafluoroethylene, silicone rubber, fluorocarbon silicone rubber, natural rubber, polyacrylate, aromatic polyester (e.g., polyethylene terephthalate (PET)), non-degradable polyurethane, polyetheretherketone, polyacrylonitrile, polysiloxane, polyoxymethylene, polyvinyl chloride or any combination thereof).

In some preferred embodiments, the biocompatible material comprises a non-biodegradable material (e.g., nylon, terylene, polypropylene, polyethylene, polytetrafluoroethylene, silicone rubber, fluorocarbon silicone rubber, natural rubber, polyacrylate, aromatic polyester (e.g., polyethylene terephthalate (PET)), non-degradable polyurethane, polyetheretherketones, polyacrylonitriles, polysiloxanes, polyoxymethylene, polyvinyl chloride or any combination thereof).

In some preferred embodiments, the non-biodegradable material is bioinert.

In some preferred embodiments, the solid support is a tubular solid support or a sheet-like solid support.

In some preferred embodiments, the solid support is prepared by means of mold immersing, electrospinning, extrusion forging, 3D printing or spraying.

In some preferred embodiments, the solid support is obtained by means of a mold immersing process. In some preferred embodiments, the mold immersing process comprises the following steps of:

(1) dissolving a material (e.g., a biodegradable material) used for preparing the solid support in a suitable solvent (e.g., an organic solvent such as chloroform, tetrahydrofuran or N,N-dimethylacetamide) to formulate a preparation solution;

(2) immersing a mold in the preparation solution, then taking out the mold, and volatilizing the solvent on the mold; and (3) repeating the step (2) for a plurality of times to obtain the solid support;

optionally, the process further comprises a step of:

drying, cutting and/or sterilizing the solid support.

In some preferred embodiments, the concentration of a material for preparing the solid support in the preparation solution is of 0.5 wt % to 5 wt %, such as 0.5 wt % to 1 wt %, 1 wt % to 1.5 wt %, 1.5 wt % to 2 wt %, 2 wt % to 2.5 wt %, 2.5 wt % to 3 wt %, 3 wt % to 3.5 wt %, 3.5 wt % to 4 wt %, 4 wt % to 4.5 wt % or 4.5 wt % to 5 wt %, such as 0.5 wt %, 1 wt %, 1.5 wt %, 2 wt %, 2.5 wt %, 3 wt %, 3.5 wt %, 4 wt %, 4.5 wt % or 5 wt %.

In some preferred embodiments, the solid support is prepared by an electrospinning process.

In some preferred embodiments, the electrospinning process comprises the following steps of:

(1) dissolving a material (e.g., a biodegradable material) used for preparing the solid support in a suitable solvent (e.g., an organic solvent such as chloroform) to formulate a preparation solution;

(2) spinning the preparation solution in an electrospinning device to form a solid support; and (3) separating the solid support from the electrospinning device after the solvent has volatilized.

In some preferred embodiments, the solid support is prepared on the surface of a biological construct.

In some preferred embodiments, the solid support is prepared on the surface of a biological construct by means of 3D printing or spraying.

In the present invention, an artificial tissue progenitor can be formed into a desired shape as required. In some preferred embodiments, microcapsules are used to prepare a biological construct in a desired shape which is in combination with a solid support in a desired shape. In some preferred embodiments, microcapsules are used to prepare a biological construct in a desired shape on a solid support in a desired shape. In certain preferred embodiments, microcapsules are used to prepare a biological construct in a desired shape, and a solid support in a desired shape is prepared on the biological construct.

In some preferred embodiments, the artificial tissue progenitor comprises one or more biological constructs in a desired shape.

In some preferred embodiments, the artificial tissue progenitor is in a form of tube (e.g., a round tube; e.g., tube with or without an opening at side wall), the solid support is a tubular solid support (e.g., in the form of a round tube; e.g., in the form of a tube with or without an opening at side wall), a plurality of the microcapsules constitutes one or more tubular biological constructs (e.g., in the form of a round tube; e.g., in the form of a tube with or without an opening at side wall), and at least one tubular biological construct has an outer wall attached to the inner wall of the tubular solid support;

In some preferred embodiments, the artificial tissue progenitor comprises a tubular solid support and a tubular biological construct that has no opening at side wall, and the tubular biological construct has an outer wall attached to the inner wall of the tubular solid support.

In some preferred embodiments, the artificial tissue progenitor comprises a plurality of tubular biological constructs.

FIG. 3A to FIG. 3E exemplarily depict the structure of a tubular artificial tissue progenitor comprising a plurality of tubular biological constructs.

FIG. 3A is a side view of a tubular artificial tissue progenitor, wherein the artificial tissue progenitor comprises a tubular solid support and a plurality of tubular biological constructs which have no opening at side walls, wherein the tubular biological constructs are inside the tubular solid support and are aligned along the axial direction of the tubular solid support, and the outer wall of each tubular biological construct is attached to the inner wall of the tubular solid support.

FIG. 3B is a top view of a tubular artificial tissue progenitor, wherein the artificial tissue progenitor comprises a tubular solid support and a plurality of tubular biological constructs which have no opening at side walls, wherein the tubular biological constructs are inside the tubular solid support and are coaxially disposed with the tubular solid support, and the outer wall of the outermost tubular biological construct is attached to the inner wall of the tubular solid support.

FIG. 3C is a side view of a tubular artificial tissue progenitor, wherein the artificial tissue progenitor comprises a tubular solid support and a plurality of tubular biological constructs, wherein each tubular biological construct has an opening at side wall, wherein the tubular biological constructs are inside the tubular solid support and are aligned along the axial direction of the tubular solid support, and the outer wall of each tubular biological construct is attached to the inner wall of the tubular solid support.

FIG. 3D is a top view of a tubular artificial tissue progenitor, wherein the artificial tissue progenitor comprises a tubular solid support and a plurality of tubular biological constructs, wherein each tubular biological construct has an opening at side wall, wherein the tubular biological constructs are inside the tubular solid support and are coaxially disposed with the tubular solid support and radially aligned, and the outer wall of the outermost tubular biological construct is attached to the inner wall of the tubular solid support.

FIG. 3E is a top view of a tubular artificial tissue progenitor, wherein the artificial tissue progenitor comprises a tubular solid support and a plurality of tubular biological constructs, wherein each tubular biological construct has an opening at side wall, wherein the tubular biological constructs are inside the tubular solid support and are coaxially disposed with the tubular solid support, and the outer wall of each tubular biological construct is attached to the inner wall of the tubular solid support.

In some preferred embodiments, the artificial tissue progenitor comprises a tubular solid support, a tubular biological construct with an opening at side wall, and a tubular biological construct without an opening at side wall.

In the present invention, the sizes of a tubular artificial tissue progenitor and of a tubular biological construct and a tubular solid support contained therein are set as required.

In some preferred embodiments, the artificial tissue progenitor has a length of from 1 cm to 40 cm.

In some preferred embodiments, the artificial tissue progenitor has an inner diameter of from 1 mm to 3 cm (e.g., 1 mm-6 mm, 6 mm-8 mm, 8 mm-10 mm, 10 mm-12 mm, 12 mm-3 cm).

In some preferred embodiments, the artificial tissue progenitor has a uniform or non-uniform thickness. For example, a tubular biological construct(s) is attached to a certain portion of the inner wall of a tubular solid support, while other portion thereof is not attached by a tubular biological construct. For example, different tubular biological constructs are attached to different portions of the inner wall of the tubular solid support.

In some preferred embodiments, the tubular solid support has a length of from 1 cm to 40 cm (e.g., 1 cm-10 cm, 10 cm-20 cm, 20 cm-30 cm or 30 cm-40 cm).

In some preferred embodiments, the tubular solid support has an inner diameter of from 1 mm to 3 cm (e.g., 1 mm-6 mm, 6 mm-8 mm, 8 mm-10 mm, 10 mm-12 mm or 12 mm-3 cm).

In some preferred embodiments, the tubular solid support has a thickness of 200 μm-1 mm (e.g., 200 μm-400 μm, 400 μm-600 μm, 600 μm-800 μm or 800 μm-1 mm).

In some preferred embodiments, the tubular solid support is a round tube with an opening at side wall, wherein the opening goes through both ends of the tubular solid support along the axial direction, and the radial section of the tubular solid support is in a shape of a sector of an annulus; in some preferred embodiments, the sector of an annulus has a central angle of greater than 0 and less than 360°, for example, greater than 0 and less than 30°, 30°-60°, 60°-90°, 90°-120°, 120°-150°, 150°-180°, 180°-210°, 210°-240°, 240°-270°, 270°-300°, 300°-330°, or greater than 330° and less than 360°.

In some preferred embodiments, the tubular biological construct has a length of from 1 cm to 40 cm (e.g., 1 cm-10 cm, 10 cm-20 cm, 20 cm-30 cm or 30 cm-40 cm).

In some preferred embodiments, the tubular biological construct has an inner diameter of from 1 mm to 3 cm (e.g., 1 mm-6 mm, 6 mm-8 mm, 8 mm-10 mm, 10 mm-12 mm or 12 mm-3 cm).

In some preferred embodiments, the tubular biological construct has a thickness of 200 μm-1 mm (e.g., 200 μm-400 μm, 400 μm, 600 μm, 600 μm-800 μm or 800 μm-1 mm).

In some preferred embodiments, the tubular biological construct is a round tube with an opening at side wall, wherein the opening goes through both ends of the tubular biological construct along the axial direction, and the radial section of the tubular biological construct is in a shape of a sector of an annulus; In some preferred embodiments, the sector of an annulus has a central angle of greater than 0 and less than 360°.

In some preferred embodiments, the artificial tissue progenitor is in form of a sheet, the solid support is a sheet-like solid support, a plurality of the microcapsules forms one or more sheet-like biological constructs, and at least one sheet-like biological construct is attached to the sheet-like solid support.

In some preferred embodiments, the sheet-like solid support is a planar sheet or curved sheet.

In some preferred embodiments, the sheet-like biological construct is a planar sheet or curved sheet.

In some preferred embodiments, the artificial tissue progenitor comprises a sheet-like solid support and a sheet-like biological construct, wherein one of the surfaces of the sheet-like biological construct attached to a surface of the sheet-like solid support.

In some preferred embodiments, the artificial tissue progenitor comprises a sheet-like solid support and a plurality of sheet-like biological constructs, wherein the plurality of sheet-like biological constructs are located on one side of the sheet-like solid support, and each of the sheet-like biological constructs has a surface attached to a surface of the sheet-like solid support.

In some preferred embodiments, the artificial tissue progenitor comprises a sheet-like solid support and a plurality of sheet-like biological constructs, wherein the plurality of sheet-like biological constructs are stacked on one side of the sheet-like solid support, and at least one sheet-like biological construct has a surface attached to a surface of the sheet-like solid support.

In the present invention, the sizes of a sheet-like artificial tissue progenitor and of a sheet-like biological construct and of a sheet-like solid support contained therein are set as required.

In some preferred embodiments, the artificial tissue progenitor is a round sheet, an elliptical sheet, a parallelogram (e.g., rectangular) sheet, a sectorial sheet or an irregular sheet.

In some preferred embodiments, the artificial tissue progenitor has a thickness of 0.5 mm-3 mm (e.g., 0.5 mm-1 mm, 1 mm-2 mm or 2 mm-3 mm).

In some preferred embodiments, the artificial tissue progenitor has an area of is 0.5 $cm^2$-5 $cm^2$ (e.g., 0.5 $cm^2$-1 $cm^2$, 1 $cm^2$-1.5 $cm^2$, 1.5 $cm^2$-2.5 $cm^2$, 2.5 $cm^2$-2.5 $cm^2$ or 3.5 $cm^2$-5 $cm^2$).

In some preferred embodiments, the artificial tissue progenitor has a uniform or non-uniform thickness. For example, a sheet-like biological construct(s) is attached to a certain portion of a sheet-like solid support, while other portion thereof is not attached by a sheet-like biological construct. For example, different sheet-like biological constructs are attached to different portions of the sheet-like solid support.

In some preferred embodiments, the sheet-like solid support is a round sheet, an elliptical sheet, a parallelogram (e.g. rectangular) sheet, a sectorial sheet or an irregular sheet, or an approximately round, elliptical, parallelogram (e.g., rectangle) or sectorial sheet.

In some preferred embodiments, the sheet-like solid support has a thickness of 0.5 mm-3 mm (e.g., 0.5 mm-1 mm, 1 mm-2 mm or 2 mm-3 mm).

In some preferred embodiments, the sheet-like solid support has an area of is 0.5 $cm^2$-5 $cm^2$ (e.g., 0.5 $cm^2$-1 $cm^2$, 1 $cm^2$-1.5 $cm^2$, 1.5 $cm^2$-2.5 $cm^2$, 2.5 $cm^2$-2.5 $cm^2$ or 3.5 $cm^2$-5 $cm^2$).

The sheet-like biological construct is a round sheet, an elliptical sheet, a parallelogram (e.g. rectangular) sheet, a sectorial sheet or an irregular sheet, or an approximately round, elliptical, parallelogram (e.g., rectangle) or sectorial sheet.

In some preferred embodiments, the sheet-like biological construct has a thickness of 20 μm-3 mm (for example, 20 μm-100 μm, 100 μm-500 μm, 500 μm-1 mm, 1 mm-2 mm or 2 mm-3 mm).

In some preferred embodiments, the sheet-like biological construct has an area of 0.5 $cm^2$-5 $cm^2$ (e.g., 0.5 $cm^2$-1 $cm^2$, 1 $cm^2$-1.5 $cm^2$, 1.5 $cm^2$-2.5 $cm^2$, 2.5 $cm^2$-2.5 $cm^2$ or 3.5 $cm^2$-5 $cm^2$).

In some preferred embodiments, in the artificial tissue progenitor of the present invention, at least one microcapsule or at least one biological construct is immobilized with the solid support.

In some preferred embodiments, at least one microcapsule or at least one biological construct is chemically attached to the solid support.

In some preferred embodiments, at least one biological construct is adhered to the solid support with an adhesive, and more preferably, the adhesive is a medical adhesive.

Medical adhesives that may be used in the present invention include, but are not limited to:

medical adhesives for a soft tissue, for example: a tissue adhesive mainly composed of octyl 2-cyanoacrylate; fibrin adhesive (FS, which mainly contains fibrinogen+thrombin, $Ca^{2+}$ and factor VIII);

medical adhesives for a hard tissue, for example: a synthetic resin adhesive for dentistry, such as (1) methacrylates: 4-EMTA (4-methacryloyloxyethyl trimellitate), phenyp (methacryloyloxyethyl phenyl phosphate), Bis-GMA (bis-glycidyl methacrylate) etc., which are mostly used for filling of caries and bonding of dentin, (2) polycarboxylic acids, such as polyacrylate+zinc oxide or special glass filler, which are mostly used to fill tooth hole and to bind and repair with polymethyl methacrylate; bone adhesive (commonly known as bone cement comprising acrylic cement and polymethyl methacrylic (PMMA) etc. as main components).

Preferably, the medical adhesive comprises alpha-cyanoacrylates (e.g., methyl alpha-cyanoacrylate, ethyl alpha-cyanoacrylate, isobutyl alpha-cyanoacrylate, isohexyl alpha-cyanoacrylate, octyl alpha-cyanoacrylate e.g., n-octyl alpha-cyanoacrylate).

In some preferred embodiments, the adhesive are present in a commercially available medical adhesive such as Baiyun medical adhesive type EC (main components: n-octyl alpha-cyanoacrylate (508) as a main adhesive, additives (medical-grade polymethyl methacrylate), or FAL medical adhesive (composition: 99% n-butyl alpha-cyanoacrylate (NBCA/504) and 1% n-octyl alpha-cyanoacrylate (NOCA/508)).

In some preferred embodiments, the setting time of a medical adhesive may be adjusted by adjusting the concentration of the medical adhesive to achieve a good adhesion effect. The medical adhesive may be diluted with a suitable solvent, for example, the medical adhesive is diluted with ethyl acetate. The solvent may be selected from medical-grade ester solvents, such as medical-grade ethyl acetate, medical-grade polymethyl methacrylate.

In another aspect, the present application provides various methods for preparing the artificial tissue progenitors as described above.

Method 1: a method of preparing an artificial tissue progenitor that is in a form of tube, comprising the following steps:

(I) preparing a tubular (e.g., in a shape of a round tube; e.g., in a shape of a tube with or without an opening at side wall) biological construct; and (II) attaching the tubular biological construct to the inner wall of a tubular solid support.

In some preferred embodiments, the tubular biological construct is prepared by a method comprising the following steps:

(1) providing one or more microcapsules having a first component attached to all or a part of the surface of the microcapsules; preferably, the first component being contained in a first agent;

(2) coating a second agent containing a second component on a predetermined area of the surface of a temporary support, wherein a sticky effect can be produced to achieve an adhesion effect when the first component and the second component are in contact with each other; the temporary support is tubular or cylindrical support (for example, a round tube without an opening at side wall, a round tube with an opening at side wall, a cylinder or a column arranged along a part of a circumference), the predetermined area is located on the curved surface of the temporary support; optionally, coating a substrate material onto the predetermined area of the surface of the temporary support prior to coating the second agent.)

(3) placing the microcapsules having the first component attached to all or a part of the surface thereof in step (1) on the predetermined area coated with the second agent so that the first component on the surface of the microcapsules is in contact with the second component on the predetermined area to produce a sticky effect, thereby assembling (adhering) the microcapsules into a first layer structure, the first layer structure being a tubular structure;

optionally, the method further comprises the following steps:

(4) coating the second agent onto the structure formed in the previous step;

(5) placing the microcapsules having the first component attached to all or a part of the surface thereof in step (1) on the structure produced in the previous step so that the first component on the surface of the microcapsules is in contact with the second component on the structure produced in the previous step to produce a sticky effect, thereby assembling (adhering) the microcapsules into another layer structure on the structure produced in the previous step; and (6) optionally, repeating the steps (4) and (5) for one or more times, for example, at least 1, at least 2, at least 3, at least 4, at least 5, at least 10, at least 15, at least 20, at least 30, at least 40, at least 50, at least 100, at least 200, at least 500 times, or more times, thereby obtaining the tubular biological construct.

Optionally, the method further comprises: adhering the round tubular biological construct with an opening at side wall to provide a round tubular biological construct without an opening at side wall.

Optionally, the method further comprises: separating the tubular biological construct from the temporary support.

In some preferred embodiments, the temporary support is a printing platform having a curved surface, such as a rotary rod of a 3D printer.

In some preferred embodiments, the substrate material is a temperature sensitive material such as gelatin, poly N-isopropylacrylamide, poly N-isopropylacrylamide-polyethylene glycol block copolymer, polyethylene glycol copolymer (e.g., polyvinyl alcohol-polyethylene glycol copolymer), polyhydroxyethylacrylate, agarose, Matrigel, chitosan/sodium glycerophosphate series or Pluronic F127.

In some preferred embodiments, the temporary support is a cylinder or round tube made from a temperature sensitive material (e.g., gelatin, poly N-isopropylacrylamide, poly N-isopropylacrylamide-polyethylene glycol block copolymer, polyethylene glycol copolymer (e.g., polyvinyl alcohol-polyethylene glycol copolymer), polyhydroxyethylacrylate, agarose, Matrigel, chitosan/sodium glycerophosphate series or Pluronic F127).

In some preferred embodiments, the temporary support is a cylinder. FIG. 4A exemplarily depicts a cylinder as a temporary support.

In some preferred embodiments, the temporary support is a cylinder. As shown in FIG. 4B, the predetermined area is the entire side surface of the cylinder, whereby, the first layer structure obtained in the step (3) is a round tubular structure without an opening at side wall.

In some preferred embodiments, the temporary support is a cylinder. As shown in FIG. 4C, the predetermined area is a rectangle on the unfolded side surface of the cylinder, and the predetermined area goes through the side surface of the cylinder in the axial direction of the cylinder, whereby, the first layer structure obtained in the step (3) is a round tubular structure without an opening at side wall.

In some preferred embodiments, the temporary support is a cylinder. As shown in FIG. 4D, the predetermined area is a rectangle on the unfolded side surface of the cylinder, and the predetermined area goes through the side surface of the cylinder in the circumferential direction of the cylinder, whereby, the first layer structure obtained in the step (3) is a round tubular structure without an opening at side wall.

In some preferred embodiments, the temporary support is a cylinder. As shown in FIG. 4E, the predetermined area is a rectangle on the unfolded side surface of the cylinder, and the predetermined area does not go through the side surface of the cylinder in the axial or circumferential direction of the cylinder, whereby, the first layer structure obtained in the step (3) is a round tubular structure with an opening at side wall.

In some preferred embodiments, in the step (3), the microcapsules having the first component attached to all or a part of the surface are left to stand for 0.1 s-60 s (e.g., 0.1 s-1 s, 1 s-5 s, 5 s-10 s, 10 s-15 s, 15 s-20 s, 20 s-25 s, 25 s-30 s, 30 s-35 s, 35 s-40 s, 40 s-45 s, 45 s-50 s, 50 s-55 s or 55 s-60 s) after placed on the predetermined area coated with the second agent in step (2). The step of standing facilitates full contact and interaction between the first component on the surface of the microcapsules and the second component on the predetermined area to assemble (adhere) the microcapsules into the first layer structure.

In some preferred embodiments, a method of preparing the tubular biological construct is performed by a bio-printing process.

In some preferred embodiments, a bio-printing process is performed by using a printer (e.g., a 3D bio-printer); alternatively, a bio-printing process is performed by using an automated or non-automated mechanical process; or, a bio-printing process is performed by means of manual placement or manual deposition (e.g., by using a pipette).

In some preferred embodiments, microcapsules are printed by using either an extrusion printing process or a modular printing process.

In some preferred embodiments, the second agent is printed by using a modular printing process, an extrusion printing process or an ink-jet printing process.

In some preferred embodiments, the auxiliary material is printed by using a modular printing process, an extrusion printing process or an ink-jet printing process.

In some preferred embodiments, a biological construct is prepared by using a 3D bio-printer.

In some preferred embodiments, the 3D bio-printer comprises a first ink cartridge for providing microcapsules, a second ink cartridge for providing a second agent, a first printer head, and a second printer head connected to the second ink cartridge.

In some preferred embodiments, the 3D bio-printer further comprises a third ink cartridge for providing a substrate material, and a third printer head.

In some preferred embodiments, the 3D bio-printer further comprises: a fourth ink cartridge for providing a first agent.

In some preferred embodiments, the method comprises the following steps of:

(1) providing microcapsules having a first component attached to all or a part of surface thereof in a first ink cartridge of a 3D bio-printer, and providing a second agent comprising a second component in a second ink cartridge of the 3D bio-printer, wherein a sticky effect can be produced to achieve an adhesion effect when the first component and the second component are in contact with each other;

(2) printing the second agent on the predetermined area of curved surface of the rotary rod via a second printer head connected to the second ink cartridge of the 3D bioprinter; optionally, printing a substrate material on the predetermined area prior to printing the second agent;

(3) printing the microcapsules in the step (1) on the predetermined area printed with the second agent in the step (2) via a first printer head of the 3D bio-printer so that the first component on the surface of the microcapsules is in contact with the second component on the predetermined area to produce a sticky effect, thereby assembling (adhering) the microcapsules into a first layer structure;

optionally, the method further comprises the following steps:

(4) printing the second agent on the structure formed in the previous step via the second printer head;

(5) printing the microcapsules in the step (1) on the structure produced in the previous step via the first printer head so that the first component on the surface of the microcapsules is in contact with the second component on the structure produced in the previous step to produce a sticky effect, thereby assembling (adhering) the microcapsules into another layer structure on the structure produced in the previous step; and (6) optionally, repeating the steps (4) and (5) for one or more times, for example, at least 1, at least 2, at least 3, at least 4, at least 5, at least 10, at least 15, at least 20, at least 30, at least 40, at least 50, at least 100, at least 200, at least 500 times, or more times, thereby obtaining the tubular biological construct.

Method 2: a method of preparing an artificial tissue progenitor that is in a form of tube, comprising the following steps:

(I) preparing a tubular (e.g., in a shape of a round tube; e.g., in a shape of tube with or without an opening at side wall) biological construct; and (II) attaching the tubular biological construct to the inner wall of a tubular solid support.

In some preferred embodiments, the tubular biological construct is prepared by a method comprising the following steps:

(1) providing one or more microcapsules having a first component attached to all or a part of the surface thereof; preferably, the first component being contained in a first agent;

(2) drawing a predetermined annular (e.g., a round annulus or a sector of an annulus) pattern on the surface of a temporary support with a second agent containing a second component, wherein a sticky effect can be produced to achieve an adhesion effect when the first component and the second component are in contact with each other; the temporary support has at least one plane, and the annular pattern is located on the plane of the temporary support;

(3) placing the microcapsules having the first component attached to all or a part of the surface thereof in step (1) on the predetermined annular pattern drawn with the second agent so that the first component on the surface of the microcapsules is in contact with the second component on the annular pattern to produce a sticky effect, thereby assembling (adhering) the microcapsules into a first layer structure, the first layer structure being an annular structure;

(4) coating the second agent onto the annular structure;

(5) placing the microcapsules having the first component attached to all or a part of the surface thereof in step (1) on the structure produced in the previous step so that the first component on the surface of the microcapsules is in contact with the second component on the structure produced in the previous step to produce a sticky effect, thereby assembling (adhering) the microcapsules into another layer structure on the structure produced in the previous step; and (6) optionally, repeating the steps (4) and (5) for one or more times, for example, at least 1, at least 2, at least 3, at least 4, at least 5, at least 10, at least 15, at least 20, at least 30, at least 40, at least 50, at least 100, at least 200, at least 500 times, or more times, thereby obtaining the tubular biological construct.

Optionally, the method further comprises: adhering the round tubular biological construct with an opening at side wall to provide a round tubular biological construct without an opening at side wall.

In some preferred embodiments, the temporary support is a printing platform of a 3D printer.

In some preferred embodiments, in the step (3), the microcapsules having the first component attached to all or a part of the surface are left to stand for 0.1 s-60 s (e.g., 0.1 s-1 s, 1 s-5 s, 5 s-10 s, 10 s-15 s, 15 s-20 s, 20 s-25 s, 25 s-30 s, 30 s-35 s, 35 s-40 s, 40 s-45 s, 45 s-50 s, 50 s-55 s or 55-60 s) after placed on the predetermined annular pattern drawn in the step (2). The step of standing facilitates full contact and interaction between the first component on the surface of the microcapsules and the second component on the predetermined area to assemble (adhere) the microcapsules into the first layer structure.

In some preferred embodiments, a method of preparing the tubular biological construct is performed by a bio-printing process.

In some preferred embodiments, a bio-printing process is performed by using a printer (e.g., a 3D bio-printer); alternatively, a bio-printing process is performed by using an automated or non-automated mechanical process; or, a bio-printing process is performed by means of manual placement or manual deposition (e.g., by using a pipette).

In some preferred embodiments, microcapsules are printed by using either an extrusion printing process or a modular printing process.

In some preferred embodiments, the second agent is printed by using a modular printing process, an extrusion printing process or an ink-jet printing process.

In some preferred embodiments, the auxiliary material is printed by using a modular printing process, an extrusion printing process or an ink-jet printing process.

Wherein the biological construct is prepared by using a 3D bio-printer.

In some preferred embodiments, the 3D bio-printer comprises a first ink cartridge for providing microcapsules, a second ink cartridge for providing a second agent, a first printer head, and a second printer head connected to the second ink cartridge.

In some preferred embodiments, the 3D bio-printer further comprises a third ink cartridge for providing an auxiliary material, and a third printer head.

In some preferred embodiments, the 3D bio-printer further comprises: a fourth ink cartridge for providing a first agent.

In some preferred embodiments, the method comprises the following steps of:

(1) providing microcapsules having a first component attached to all or a part of surface thereof in a first ink cartridge of a 3D bio-printer, and providing a second agent comprising a second component in a second ink cartridge of the 3D bio-printer, wherein a sticky effect can be produced to achieve an adhesion effect when the first component and the second component are in contact with each other;

(2) drawing an annular pattern (e.g., a round annulus or a sector of an annulus) with the second agent on the printing platform via a second printer head connected to the second ink cartridge of the 3D bioprinter;

(3) printing the microcapsules in the step (1) on the annular pattern drawn in the step (2) via a first printer head of the 3D bio-printer so that the first component on the surface of the microcapsules is in contact with the second component on the annular pattern to produce a sticky effect, thereby assembling (adhering) the microcapsules into a first layer structure;

optionally, the method further comprises the following steps:

(4) printing the second agent on the structure formed in the previous step via the second printer head;

(5) printing the microcapsules in the step (1) on the structure produced in the previous step via the first printer head so that the first component on the surface of the microcapsules is in contact with the second component on the structure produced in the previous step to produce a sticky effect, thereby assembling (adhering) the microcapsules into another layer structure on the structure produced in the previous step; and (6) optionally, repeating the steps (4) and (5) for one or more times, for example, a least 1, at least 2, at least 3, at least 4, at least 5, at least 10, at least 15, at least 20, at least 30, at least 40, at least 50, at least 100, at least 200, at least 500 times, or more times, thereby obtaining the tubular biological construct.

The exemplary patterns in shapes of a round annulus and a sector of an annulus are shown in FIG. 5A.

Method 3: a method of preparing an artificial tissue progenitor that is in a sheet-like form, comprising the following steps:

(I) preparing a sheet-like (e.g., in a shape of a planar sheet, or in a shape of a curved sheet) biological construct; and (II) attaching the sheet-like biological construct to a sheet-like solid support.

In some preferred embodiments, the sheet-like biological construct is prepared by a method comprising the following steps:

(1) providing one or more microcapsules having a first component attached to all or a part of the surface thereof; preferably, the first component being contained in a first agent;

(2) coating a second agent containing a second component on a predetermined area of the surface of a temporary support, wherein a sticky effect can be produced to achieve an adhesion effect when the first component and the second component are in contact with each other; the temporary support has at least one plane, and the predetermined area is located on the plane of the temporary support;

(3) placing the microcapsules having the first component attached to all or a part of the surface thereof in step (1) on the predetermined area coated with the second agent so that the first component on the surface of the microcapsules is in contact with the second component on the predetermined area to produce a sticky effect, thereby assembling (adhering) the microcapsules into a first layer structure, the first layer structure being a sheet-like structure;

optionally, the method further comprises the following steps:

(4) coating the second agent onto the structure formed in the previous step;

(5) placing the microcapsules having the first component attached to all or a part of the surface thereof in step (1) on the structure produced in the previous step so that the first component on the surface of the microcapsules is in contact with the second component on the structure produced in the previous step to produce a sticky effect, thereby assembling (adhering) the microcapsules into another layer structure on the structure produced in the previous step; and (6) optionally, repeating the steps (4) and (5) for one or more times, for example, at least 1, at least 2, at least 3, at least 4, at least 5, at least 10, at least 15, at least 20, at least 30, at least 40, at least 50, at least 100, at least 200, at least 500 times, or more times, thereby obtaining the planer, sheet-like biological construct;

optionally, the method further comprises bending the planar, sheet-like biological construct to give a curved, sheet-like biological construct.

In some preferred embodiments, the predetermined area is a parallelogram (e.g., rectangular) area, a round area, an elliptical area, a sectorial area or an irregular area.

In some preferred embodiments, the temporary support is a printing platform of a 3D printer.

In some preferred embodiments, in the step (3), the microcapsules having the first component attached to all or a part of the surface thereof are left to stand for 0.1-60 s after placed on the predetermined area coated with the second agent in step (2).

In some preferred embodiments, in the step (3), the microcapsules having the first component attached to all or a part of the surface thereof are left to stand for 0.1 s-60 s (e.g., 0.1 s-1 s, 1 s-5 s, 5 s-10 s, 10 s-15 s, 15 s-20 s, 20 s-25 s, 25 s-30 s, 30 s-35 s, 35 s-40 s. 40 s-45 s, 45 s-50 s, 50 s-55 s or 55 s-60 s) after placed on the predetermined area coated with the second agent in step (2). The step of standing facilitates full contact and interaction between the first component on the surface of the microcapsules and the second component on the predetermined area to assemble (adhere) the microcapsules into the first layer structure.

In some preferred embodiments, a method of preparing the tubular biological construct is performed by a bio-printing process.

In some preferred embodiments, a bio-printing process is performed by using a printer (e.g., a 3D bio-printer); alternatively, a bio-printing process is performed by using an automated or non-automated mechanical process; or, a bio-printing process is performed by means of manual placement or manual deposition (e.g., by using a pipette).

In some preferred embodiments, microcapsules are printed by using either an extrusion printing process or a modular printing process.

In some preferred embodiments, the second agent is printed by using a modular printing process, an extrusion printing process or an ink-jet printing process.

In some preferred embodiments, the auxiliary material is printed by using a modular printing process, an extrusion printing process or an ink-jet printing process.

In some preferred embodiments, the biological construct is prepared by using a 3D bio-printer.

In some preferred embodiments, the 3D bio-printer comprises a first ink cartridge for providing microcapsules, a second ink cartridge for providing a second agent, a first printer head, and a second printer head connected to the second ink cartridge.

In some preferred embodiments, the 3D bio-printer further comprises a third ink cartridge for providing a first agent In some preferred embodiments, the method comprises the following steps of:

(1) providing microcapsules having a first component attached to all or a part of surface thereof in a first ink cartridge of a 3D bio-printer, and providing a second agent comprising a second component in a second ink cartridge of the 3D bio-printer, wherein a sticky effect can be produced to achieve an adhesion effect when the first component and the second component are in contact with each other;

(2) printing the second agent on the predetermined area of the printing platform via a second printer head connected to the second ink cartridge of the 3D bioprinter;

(3) printing the microcapsules in the step (1) on the predetermined area printed with the second agent in the step (2) via a first printer head of the 3D bio-printer so that the first component on the surface of the microcapsules is in contact with the second component on the predetermined area to produce a sticky effect, thereby assembling (adhering) the microcapsules into a first layer structure;

optionally, the method further comprises the following steps:

(4) printing the second agent on the structure formed in the previous step via the second printer head;

(5) printing the microcapsules in the step (1) on the structure produced in the previous step via the first printer head so that the first component on the surface of the microcapsules is in contact with the second component on the structure produced in the previous step to produce a sticky effect, thereby assembling (adhering) the microcapsules into another layer structure on the structure produced in the previous step; and (6) optionally, repeating the steps (4) and (5) for one or more times, for example, at least 1, at least 2, at least 3, at least 4, at least 5, at least 10, at least 15, at least 20, at least 30, at least 40, at least 50, at least 100, at least 200, at least 500 times, or more times, thereby obtaining the sheet-like biological construct.

Optionally, the method further comprises bending the planar, sheet-like biological construct to give a curved, sheet-like biological construct.

In some preferred embodiments, the predetermined area is a parallelogram (e.g., rectangular) area, a round area or an elliptical area.

In some preferred embodiments, the temporary support is a printing platform of a 3D printer.

In some preferred embodiments, in the step (3), the microcapsules having the first component attached to all or a part of the surface thereof are left to stand for 0.1 s-60 s after placed on the predetermined area coated with the second agent in step (2).

In some preferred embodiments, the sheet-like biological construct is prepared by using a 3D bio-printer.

In some preferred embodiments, the 3D bio-printer comprises a first ink cartridge for providing microcapsules, a second ink cartridge for providing a second agent, a first printer head, and a second printer head connected to the second ink cartridge.

In some preferred embodiments, the 3D bio-printer further comprises a third ink cartridge for providing a first agent.

In some preferred embodiments, the method comprises the following steps of:

(1) providing microcapsules having a first component attached to all or a part of surface thereof in a first ink cartridge of a 3D bio-printer, and providing a second agent comprising a second component in a second ink cartridge of the 3D bio-printer, wherein a sticky effect can be produced to achieve an adhesion effect when the first component and the second component are in contact with each other;

(2) printing the second agent on the predetermined area of the printing platform via a second printer head connected to the second ink cartridge of the 3D bioprinter;

(3) printing the microcapsules in the step (1) on the predetermined area printed with the second agent in the step (2) via a first printer head of the 3D bio-printer so that the first component on the surface of the microcapsules is in contact with the second component on the predetermined area to produce a sticky effect, thereby assembling (adhering) the microcapsules into a first layer structure;

optionally, the method further comprises the following steps:

(4) printing the second agent on the structure formed in the previous step via the second printer head;

(5) printing the microcapsules in the step (1) on the structure produced in the previous step via the first printer head so that the first component on the surface of the microcapsules is in contact with the second component on the structure produced in the previous step to produce a sticky effect, thereby assembling (adhering) the microcapsules into another layer structure on the structure produced in the previous step; and (6) optionally, repeating the steps (4) and (5) for one or more times, for example, at least 1, at least 2, at least 3, at least 4, at least 5, at least 10, at least 15, at least 20, at least 30, at least 40, at least 50, at least 100, at least 200, at least 500 times, or more times, thereby obtaining the sheet-like biological construct.

Method 4: a method of preparing an artificial tissue progenitor that is in a form of sheet, comprising the following steps:

(I) preparing a sheet-like biological construct according to the method for preparing a sheet-like biological construct in the Method 3; and (II) providing a material (e.g., a biocompatible material) for preparing a solid support, and preparing a sheet-like solid support on the sheet-like biological construct.

In some preferred embodiments, the sheet-like solid support is prepared by a 3D-printing or spraying process.

Method 5: a method of preparing an artificial tissue progenitor that is in a form of tube, comprising the following steps:

(I) preparing a sheet-like biological construct according to the method for preparing a sheet-like biological construct in Method 3;

(II) bending the sheet-like biological construct prepared in the step (I), and/or adhering the edges of the sheet-like biological construct to obtain a tubular biological construct; and (III) attaching the tubular biological construct to the inner wall of a tubular solid support.

Method 6: a method of preparing an artificial tissue progenitor that is in a form of tube, comprising the following steps:

(I) preparing a tubular biological construct prepared according to the method for preparing a tubular biological construct in Method 1 or Method 2;

or preparing a sheet-like biological construct according to the method for preparing a sheet-like biological construct in Method 3; then, bending the sheet-like biological construct, and/or adhering the edges of the sheet-like biological construct to obtain a tubular biological construct; and (II) providing a material (e.g., a biocompatible material) for preparing a solid support, and preparing a tubular solid support on the outer wall of the tubular biological construct.

In some preferred embodiments, the tubular solid support is prepared by a 3D-printing or spraying process.

The method of preparing an artificial tissue progenitor as defined in any one of Method 1 to Method 6, further comprises shaping the biological construct.

In some preferred embodiments, a shaping agent (e.g., a commercially available medical adhesive containing alpha-cyanoacrylate) is sprayed on a biological construct according to the desired structural stability and thickness of the biological construct. The number of layer of sprayed shaping agent is more, the structure of the biological construct is more stable, and/or the thickness thereof is greater.

In some preferred embodiments, a method for shaping a biological construct comprises the following steps:

1) spraying a layer of medical adhesive on the surface of the biological construct until the medical adhesive is solidified;

2) dropping a cell culture medium to the surface of the biological construct sprayed with the medical adhesive, and evenly smearing the medium;

3) spraying the medical adhesive again, wherein the medical adhesive is rapidly solidified under the action of anions in the culture medium;

4) optionally, repeating steps 2) and 3).

A medical adhesive layer can be formed on the surface of the biological construct by the above method to make the biological construct stable and firm. The method can also be used to adjust the thickness of a biological construct to facilitate matching of the construct with a solid support.

Method 7: a method of preparing a tubular or sheet-like artificial tissue progenitor, comprising the following steps:

(1) providing one or more microcapsules having a first component attached to all or a part of the surface thereof; in some preferred embodiments, the first component being contained in a first agent;

(2) providing a solid support, and coating a second agent containing a second component on a predetermined area of the surface of the solid support, wherein a sticky effect can be produced to achieve an adhesion effect when the first component and the second component are in contact with each other;

(3) placing the microcapsules having the first component attached to all or a part of the surface thereof in step (1) on the predetermined area coated with the second agent so that the first component on the surface of the microcapsules is in contact with the second component on the predetermined area to produce a sticky effect, thereby assembling (adhering) the microcapsules into a first layer structure on the surface of the solid support;

optionally, the method further comprises the following steps:

(4) coating the second agent onto the structure formed in the previous step;

(5) placing the microcapsules having the first component attached to all or a part of the surface thereof in step (1) on the structure produced in the previous step so that the first component on the surface of the microcapsules is in contact with the second component on the structure produced in the previous step to produce a sticky effect, thereby assembling (adhering) the microcapsules into another layer structure on the structure produced in the previous step; and (6) optionally, repeating the steps (4) and (5) for one or more times, for example, at least 1, at least 2, at least 3, at least 4, at least 5, at least 10, at least 15, at least 20, at least 30, at least 40, at least 50, at least 100, at least 200, at least 500 times, or more times, thereby obtaining the artificial tissue progenitor.

In some preferred embodiments, the solid support is a tubular or sheet-like support.

In some preferred embodiments, the solid support is a tubular solid support, and the predetermined area is located in the inner wall of the solid support.

In some preferred embodiments, in the step (3), the microcapsules having the first component attached to all or a part of the surface thereof are left to stand for 0.1 s-60 s (e.g., 0.1 s-1 s, 1 s-5 s, 5 s-10 s, 10 s-15 s, 15 s-20 s, 20 s-25 s, 25 s-30 s, 30 s-35 s, 35 s-40 s, 40 s-45 s, 45 s-50 s, 50 s-55 s or 55 s-60 s) after placed on the predetermined area coated with the second agent in step (2). The step of standing facilitates full contact and interaction between the first component on the surface of the microcapsules and the second component on the predetermined area to assemble (adhere) the microcapsules into the first layer structure.

In some preferred embodiments, the artificial tissue progenitor is prepared by using a 3D bio-printer.

In some preferred embodiments, the 3D bio-printer comprises a first ink cartridge for providing microcapsules, a second ink cartridge for providing a second agent, a first printer head, and a second printer head connected to the second ink cartridge.

In some preferred embodiments, the 3D bio-printer further comprises a third ink cartridge for providing a first agent.

In some preferred embodiments, the method comprises the following steps of:

(1) providing microcapsules having a first component attached to all or a part of surface thereof in a first ink cartridge of a 3D bio-printer, and providing a second agent comprising a second component in a second ink cartridge of the 3D bio-printer, wherein a sticky effect can be produced to achieve an adhesion effect when the first component and the second component are in contact with each other;

(2) printing the second agent on the predetermined area of a solid support via a second printer head connected to the second ink cartridge of the 3D bio-printer;

(3) printing the microcapsules in the step (1) on the predetermined area printed with the second agent in the step (2) via a first printer head of the 3D bio-printer so that the first component on the surface of the microcapsules is in contact with the second component on the predetermined area to produce a sticky effect, thereby assembling (adhering) the microcapsules into a first layer structure;

optionally, the method further comprises the following steps:

(4) printing the second agent on the structure formed in the previous step via the second printer head;

(5) printing the microcapsules in the step (1) on the structure produced in the previous step via the first printer head so that the first component on the surface of the microcapsules is in contact with the second component on the structure produced in the previous step to produce a sticky effect, thereby assembling (adhering) the microcapsules into another layer structure on the structure produced in the previous step; and (6) optionally, repeating the steps (4) and (5) for one or more times, for example, at least 1, at least 2, at least 3, at least 4, at least 5, at least 10, at least 15, at least 20, at least 30, at least 40, at least 50, at least 100, at least 200, at least 500 times, or more times, thereby obtaining the artificial tissue progenitor.

In the method for preparing an artificial tissue progenitor of the present invention, preferably, the first component and/or the second component is a biocompatible material. In some preferred embodiments, the first component and/or the second component is a bio-derived material. In some preferred embodiments, the first component and/or the second component is a biodegradable material.

In some preferred embodiments, the first component and the second component are capable of strong interacting (e.g., chemical reaction) upon contact and result in production of a sticky effect to achieve an adhesion effect. Such adhesion effect can not only achieve the adhesion between cells and cells, between cells and tissues and between tissues and tissues, but also achieve the adhesion between the cells/tissues and external substances. It is particularly preferred that such adhesion effect has at least one property selected from the group consisting of: (1) it is safe, reliable, non-toxic, non-carcinogenic, non-teratogenic and non-mutagenic; (2) it has a good biocompatibility, and does not hinder the self-healing of organic tissues; (3) it can be used under the conditions of bloods and tissue fluids; (4) it can realize fast adhesion under normal temperature and normal pressure; (5) it has good adhesive strength and durability, wherein the adhered portion has a certain elasticity and toughness; (6) it is non-irritable to organic tissues during use; (7) after the adhesive effect is achieved, relevant components can be gradually degraded and absorbed; and (8) the adhered portion can allow cells to be migrated through.

In some preferred embodiments, the sticky effect resulting from the contact of the first component with the second component can be used to adhere the microcapsules together to form a biological construct; and the resulting biological construct thus obtained has a tensile modulus of not less than 10 Pa, for example, not less than 20 Pa, not less than 30 Pa, not less than 40 Pa, not less than 50 Pa, not less than 60 Pa, not less than 70 Pa, not less than 80 Pa, not less than 90 Pa, not less than 100 Pa, not less than 200 Pa, not less than 300 Pa, not less than 400 Pa, not less than 500 Pa, not less than 600 Pa, not less than 700 Pa, no less than 800 Pa, no less than 900 Pa, or no less than 1000 Pa. In some preferred embodiments, the resulting construct thus obtained has a tensile modulus of up to 1 KPa to 10 Mpa, for example, 1 KPa to 5 KPa, 5 KPa to 10 KPa, 10 KPa to 50 KPa, 50 KPa to 100 KPa, 100 KPa to 500 KPa, 500 KPa to 1000 KPa, 1 MPa-5 MPa or 5 MPa-10 MPa. In some preferred embodiments, the cells in the microcapsule are able to migrate through the adhered portion to enter into adjacent microcapsules or distant microcapsules. As a result, the cells in the microcapsules are able to grow, migrate, differentiate and proliferate throughout the construct.

In some preferred embodiments, the first component and the second component are selected from a combination of the following:

(1) fibrinogen and thrombin;

(2) alginate (e.g., sodium alginate) or oxidized alginate (e.g., oxidized sodium alginate), and a substance containing $Ca^{2+}$, $Mg^{2+}$, $Ba^{2+}$, $Sr^{2+}$ or $Fe^{3+}$ (for example, a solution or semi-solid (e.g., gel) containing $Ca^{2+}$, $Mg^{2+}$, $Sr^{2+}$ or $Fe^{3+}$);

(3) maleimide group-containing molecule (e.g., polyethylene glycol containing a maleimide group (MAL-PEG)) and free thiol group-containing molecule (e.g., polyethylene glycol containing a free thiol group (PEG-SH));

(4) anion-containing material (e.g., a solution or semi-solid (e.g., gel) containing anions) and alpha-cyanoacrylate (e.g., methyl alpha-cyanoacrylate, ethyl alpha-cyanoacrylate, isobutyl alpha-cyanoacrylate, isohexyl alpha-cyanoacrylate, n-octyl alpha-cyanoacrylate);

(5) fibrinogen and alpha-cyanoacrylate (e.g., methyl alpha-cyanoacrylate, ethyl alpha-cyanoacrylate, isobutyl alpha-cyanoacrylate, isohexyl alpha-cyanoacrylate or n-octyl alpha-cyanoacrylate);

(6) serum albumin (e.g., bovine serum albumin) and glutaraldehyde;

(7) molecule containing a carbamate group (—NHCOO—) or containing an isocyanate group (—NCO) (e.g., polyethylene glycol containing a carbamate group or polyethylene glycol containing an isocyanate group) and molecule containing reactive hydrogen (e.g., carboxyl-containing polyethylene glycol);

(8) gelatin-resorcinol and glutaraldehyde;

(9) carbodiimide cross-linked gelatin and poly-L-glutamic acid (PLGA); and

(10) aminated gelatin and polysaccharide aldehyde.

It should be particularly pointed out that as long as the first component and the second component can produce a sticky effect and achieve an adhesion effect by contacting, they can be used for carrying out the embodiments of the present invention. The first component and the second component of the present invention are not limited to the above specific combinations. In addition, when a certain combination is used as the first component and the second component, the first component may be any member of the combination and the second component is the other member of the combination. For example, when a combination of fibrinogen and thrombin is used, the first component may be fibrinogen (in this case the second component is thrombin), or may be thrombin (in this case the second component is fibrinogen).

In some preferred embodiments, the first component is fibrinogen and the second component is thrombin. In some preferred embodiments, the first component is an alginate (e.g., sodium alginate) or an oxidized alginate (e.g., oxidized sodium alginate), and the second component is a substance containing $Ca^{2+}$, $Mg^{2+}$, $Ba^{2+}$, $Sr^{2+}$ or $Fe^{3+}$, such as a solution or semi-solid (e.g., a gel) containing $Ca^{2+}$, $Mg^{2+}$, $Ba^{2+}$, $Sr^{2+}$ or $Fe^{3+}$. In some preferred embodiments, the first component is a maleimide group-containing molecule (e.g., polyethylene glycol containing a maleimide group (MAL-PEG)) and the second component is a free thiol group-containing molecule (e.g., polyethylene glycol containing a free thiol group (PEG-SH)). In some preferred embodiments, the first component is an anion containing material (e.g., a solution or semi-solid (e.g., a gel) containing anions), and the second component is an alpha-cyanoacrylate (e.g., methyl alpha-cyanoacrylate, ethyl alpha-cyanoacrylate, isobutyl alpha-cyanoacrylate, isohexyl alpha-cyanoacrylate or n-octyl alpha-cyanoacrylate). In some preferred embodiments, the first component is fibrinogen, and the second component is an alpha-cyanoacrylate (e.g., methyl alpha-cyanoacrylate, ethyl alpha-cyanoacrylate, isobutyl alpha-cyanoacrylate, isohexyl alpha-cyanoacrylate or n-octyl alpha-cyanoacrylate). In some preferred embodiments, the first component is serum albumin (e.g., bovine serum albumin), and the second component is glutaraldehyde. In some preferred embodiments, the first component is a molecule containing a carbamate group (—NHCOO—) or containing an isocyanate group (—NCO) (e.g., polyethylene glycol containing a carbamate group or polyethylene glycol containing an isocyanate group), and the second component is a molecule containing reactive hydrogen (e.g., carboxyl-containing polyethylene glycol). In some preferred embodiments, the first component is gelatin-resorcinol, and the second component is glutaraldehyde. In some preferred embodiments, the first component is carbodiimide cross-linked gelatin, and the second component is poly-L-glutamic acid (PLGA). In some preferred embodiments, the first component is an aminated gelatin, and the second component is a polysaccharide aldehyde.

In some preferred embodiments, in the first agent, the concentration of the first component is of 0.01% to 50% by weight. For example, In some preferred embodiments, the concentration of the first component is of 0.01-0.05 wt %, 0.05-0.1 wt %, 0.1-0.5 wt %, 0.5-1 wt %, 1-5 wt % 5-10 wt %, 10-15 wt %, 15-20 wt %, 20-25 wt %, 25-30 wt %, 30-35 wt %, 35-40 wt %, 40-45 wt %, or 45-50 wt %.

In some preferred embodiments, in the second agent, the concentration of the second component is of 0.01% to 50% by weight. For example, In some preferred embodiments, the concentration of the second component is of 0.01-0.05 wt %, 0.05-0.1 wt %, 0.1-0.5 wt %, 0.5-1 wt %, 1-5 wt %, 5-10 wt %, 10-15 wt %, 15-20 wt %, 20-25 wt %, 25-30 wt %, 30-35 wt %, 35-40 wt %, 40-45 wt % or 45-50 wt %.

In some preferred embodiments, the strength and/or duration of adhesion effect can be controlled by selecting types and/or concentrations of the first component and the second component. For example, when fibrinogen is in contact with thrombin, the interaction between them can form a fibrin having a weak mechanical strength. Therefore, in some preferred embodiments, fibrinogen and thrombin may be used as the first and second components, and such agents are particularly suitable for use in the construction of a tissue having a less mechanical strength, such as, a tissue having a modulus of elasticity of less than 10 MPa. For example, an alpha-cyanoacrylate can react strongly with an anion containing solution to produce a polymer having a greater mechanical strength. Thus, in some preferred embodiments, an anion containing material and an alpha-cyanoacrylate can be used as the first component and the second component, and such agents are particularly suitable for use in the construction of a tissue having a greater mechanical strength, such as, a tissue having a modulus of elasticity of greater than 10 MPa.

In some preferred embodiments, the second agent is a liquid or semi-solid (e.g., a gel). In some preferred embodiments, the second agent is used to draw a predetermined pattern or is coated on a predetermined area. Accordingly, it is particularly preferred that the second agent has an appropriate viscosity so that it can stably maintain the shape/model/profile of the pattern or area when used for drawing without flowing. Therefore, in some preferred embodiments, the second agent has a viscosity of 1-1000 Pa·s, such as 30-160 Pa·s. Thus, in some preferred embodiments, the second agent has a viscosity of about 1, 2, 3, 4, 5, 6, 7, 8, 9, 10, 12, 14, 16, 18, 20, 25, 30, 50, 80, 100, 200, 300, 400, 500, 800 or 1000 Pa·s. In some preferred embodiments, the viscosity of the second agent is of 1-2, 2-3, 3-4, 4-5, 5-6, 6-7, 7-8, 8-9, 9-10, 10-12, 12-14, 14-16, 16-18, 18-20, 20-25, 25-30, 30-50, 50-80, 80-100, 100-200, 200-300, 300-400, 400-500, 500-800, or 800-1000, 1-3, 3-8, 8-16, 3-10, 10-20, 20-50, 50-160 Pa·s, or 30-160 Pa·s.

In some preferred embodiments, the second agent further comprises a third component, which is a tackifier. The viscosity of the second agent can be conveniently adjusted by adjusting the amount of the third component (tackifier) so that the second agent can maintain a particular shape, making it suitable for drawing patterns or for being coated.

In some preferred embodiments, the third component is a biocompatible material. In some preferred embodiments, the third component is a bio-derived material. In some preferred embodiments, the third component is a biodegradable material. In some preferred embodiments, the third component is a temperature-sensitive material. In some preferred embodiments, the temperature-sensitive material has a different morphology at a different temperature. For example, the temperature-sensitive material (e.g., gelatin) is present in a solid or semi-solid at a lower temperature while in a liquid at a higher temperature. In some preferred embodiments, the temperature-sensitive material has a phase transition temperature of between 5 and 40° C., such as 5-10° C., 10-15° C., 15-20° C., 20-25° C., 25-30° C. 30-35° C. or 35-40° C. In some preferred embodiments, the temperature-sensitive material is selected from the group consisting of gelatin, poly poly N-isopropylacrylamide-polyethylene glycol block copolymer, polyethylene glycol copolymer (e.g., polyvinyl alcohol-polyethylene glycol copolymer), agarose, Matrigel, chitosan/sodium glycerophosphate series, Pluronic F127 and poly N-isopropylacrylamide (PNIPAAm) hydrogel. In some preferred embodiments, the third component (tackifier) is selected from the group consisting of gelatin, block polymer F-127, agarose, polyethylene glycol, guar gum, polyvinyl alcohol, chitosan, collagen, hyaluronic acid, chitin, cellulose and a derivative thereof (such as hydroxypropyl cellulose), polyamino acid, poly N-isopropylacrylamide-polyethylene glycol block copolymer, polyethylene glycol copolymer (e.g., polyvinyl alcohol-polyethylene glycol copolymer), alginate (e.g., sodium alginate), a modified alginate (e.g., an oxidized alginate, such as oxidized sodium alginate), Matrigel, chitosan/sodium glycerophosphate series, and poly N-isopropylacrylamide (PNIPAAm) hydrogel.

In some preferred embodiments, the third component (tackifier) is gelatin.

In some preferred embodiments, in the second agent, the concentration of the third component is of 0.01% to 50% by weight. For example, In some preferred embodiments, the concentration of the third component is of 0.01-0.05 wt %, 0.05-0.1 wt %, 0.1-0.5 wt %, 0.5-1 wt %, 1-5 wt %, 5-10 wt %, 10-15 wt %, 15-20 wt %, 20-25 wt %, 25-30 wt %, 30-35 wt %, 35-40 wt %, 40-45 wt % or 45-50 wt %.

In some preferred embodiments, the microcapsules having a first component attached to all or a part of the surface thereof in the step (1) are obtained by coating a first agent containing the first component on the surface of the microcapsules. Thus, in some preferred embodiments, the step (1) comprises coating the first component on all or a portion of the surface of the microcapsules, thereby providing the microcapsules having a first agent attached to all or a part of the surface thereof.

In some preferred embodiments, the microcapsules having a first component attached to all or a part of the surface thereof in the step (1) are obtained by immersing the microcapsules in a first agent containing the first component.

In some preferred embodiments, the microcapsules are immersed in the first agent for 1-30 min, for example, 1-5 min, 5-10 min, 10-15 min, 15-20 min, 20-25 min or 25-30 min. In some preferred embodiments, in the step (1), the microcapsules are immersed in the first agent under shaking or quaking conditions. Shaking or quaking conditions can be used to promote the attachment of the first agent to the surface of the microcapsules. In some preferred embodiments, the step (1) is carried out at room temperature (e.g., 15-37° C.). In some preferred embodiments, the step (1) is carried out at a low temperature (e.g., 4-15° C.).

In some preferred embodiments, the step (1) further comprises washing the microcapsules after they are immersed in the first agent. In some preferred embodiments, the microcapsules are washed with a buffer (e.g., physiological buffer solution) or a medium solution. In some preferred embodiments, after the microcapsules are immersed in the first agent, the microcapsules are washed by immersing them in a buffer (e.g., a physiological buffer solution) or in a medium solution. The washing step can be used to remove excess first agent attached to the surface of the microcapsules. In some preferred embodiments, the washing step can be performed for 1-5 min or 5-10 min. In some preferred embodiments, the washing step can be carried out at room temperature (e.g., 15-37° C.) or at a low temperature (e.g., 4-15° C.).

In some preferred embodiments, the step (3) is carried out at room temperature (e.g., 15-37° C.) or at a low temperature (e.g., 4-15° C.).

In some preferred embodiments, in the step (5), the microcapsules having the first component attached to all or a part of the surface are left to stand for 0.1-60 s (e.g., 0.1-1 s, 1-5 s, 5-10 s, 10-15 s, 15-20 s, 20-25 s, 25-30 s, 30-35 s, 35-40 s, 40-45 s, 45-50 s, 50-55 s or 55-60 s) after placed on the structure produced in the previous step. The step of standing facilitates full contact and interaction between the first component on the surface of the microcapsules and the second component on the structure to assemble (adhere) the microcapsules into a new structural layer on the structure produced in the previous step. In some preferred embodiments, the step (6) is carried out at room temperature (e.g., 15-37° C.) or at a low temperature (e.g., 4-15° C.).

In some preferred embodiments, during the steps (2)-(6), an auxiliary material (e.g., auxiliary materials for forming framework, or auxiliary materials useful for supporting) are also added inside or outside the produced structure. In some preferred embodiments, the auxiliary materials do not contain cells. Preferably, the addition/use of the auxiliary material can help to restrict the shape of a produced artificial tissue progenitor and/or to help to maintain or enhance the stability of the produced artificial tissue progenitor. In some preferred embodiments, the auxiliary material is contained in the artificial tissue progenitor prepared by a method of the invention. In some preferred embodiments, the auxiliary material is contained within the artificial tissue progenitor prepared by a method of the invention, and then can subsequently be degraded. In such case, the auxiliary material only temporarily form a portion of the artificial tissue progenitor. In some preferred embodiments, the auxiliary material is contained in the artificial tissue progenitor prepared by a method of the invention and is non-degradable. In such case, the auxiliary material forms (directly and stably) a portion of the artificial tissue progenitor. In some preferred embodiments, such auxiliary material is biocompatible and/or biodegradable. In some preferred embodiments, the auxiliary material is a temperature-sensitive material. In some preferred embodiments, the temperature-sensitive material has a different morphology at a different temperature. For example, the temperature-sensitive material (e.g., gelatin) is present in a solid or semi-solid at a lower temperature while in a liquid at a higher temperature. In some preferred embodiments, the temperature-sensitive material has a phase transition temperature of between 5° C. and 40° C., such as 5-10° C., 10-15° C., 15-20° C., 20-25° C., 25-30° C., 30-35° C. or 35-40° C. In some preferred embodiments, the temperature-sensitive material is selected from the group consisting of gelatin, poly N-isopropylacrylamide, poly N-isopropylacrylamide-polyethylene glycol block copolymer, polyethylene glycol copolymer (e.g., polyvinyl alcohol-polyethylene glycol copolymer), polyhydroxyethyl acrylate, agarose, Matrigel, chitosan/sodium glycerophosphate series, Pluronic F127 and poly N-isopropylacrylamide (PNIPAAm) hydrogel.

In some preferred embodiments, the auxiliary material may have a desired size. In some preferred embodiments, the auxiliary material has a size at a level of micrometer to centimeter, such as 1 μm to 10 cm, for example 1 μm-2 μm, 2 μm-3 μm, 3 μm-4 μm, 4 μm-5 μm, 5 μm-6 μm, 6 μm-7 μm, 7 μm-8 μm, 8 μm-9 μm, 9 μm-10 μm, 10 μm-20 μm, 20 μm-30 μm, 30 μm-40 μm, 40 μm-50 μm, 50 μm-60 μm, 60 μm-70 μm, 70 μm-80 μm, 80 μm-90 μm, 90 μm-100 μm, 100 μm-200 μm, 200 μm-300 μm, 300 μm-400 μm, 400 μm-500 μm, 500 μm-600 μm, 600 μm-700 μm, 700 μm-800 μm, 800 μm-900 μm, 900 μm-1 mm, 1 mm-2 mm, 2 mm-3 mm, 3 mm-4 mm, 4 mm-5 mm, 5 mm-6 mm, 6 mm-7 mm, 7 mm-8 mm, 8 mm-9 mm, 9 mm-10 mm, 10 mm-20 mm, 20 mm-30 mm, 30 mm-40 mm, 40 mm-50 mm, 50 mm-60 mm, 60 mm-70 mm, 70 mm-80 mm, 80 mm-90 mm, 90 mm-100 mm, 100-5 mm, 500 μm-1 mm, 100-800 μm or 300 μm-600 μm.

In some preferred embodiments, the auxiliary material may have a desired shape. For example, the auxiliary material may be a sheet-like structure (e.g., a rectangular, square, round, elliptical, hexagonal or irregularly shaped sheet structure), or a hollow tubular structure, or a hollow three-dimensional structure (e.g., a hollow cube, a hollow sphere, a hollow rectangular prismoid, a hollow cylinder, or a hollow irregularly shaped three-dimensional structure), or a solid three-dimensional structure (e.g., a solid cube, a solid sphere, a solid rectangular prismoid, a solid cylinder, or a solid irregularly shaped three-dimensional structure), or any combination thereof. In some preferred embodiments, the shape of the auxiliary material mimics the shape of a native tissue or organ.

In some preferred embodiments, the microcapsule used to prepare a biological construct are present in a bio-ink. In some preferred embodiments, the bio-ink further comprises a carrier.

In some preferred embodiments, the carrier and degradation product thereof are non-toxic to a cell, and/or non-immunogenic to a host. In some preferred embodiments, the carrier comprises a biodegradable material. In some preferred embodiments, the biodegradable material in the carrier is biocompatible.

In some preferred embodiments, the degradation of a biodegradable material in the carrier can provide a microenvironment, such as a nutrient, that maintains or promotes the life activity of the cell within a microcapsule (e.g., a bio-block). In some preferred embodiments, the degradation product is a small molecule compound such as an organic acid, a monosaccharide (e.g., glucose), an oligosaccharide, an amino acid, a lipid and the like. Such degradation product may be involved in metabolic activity of the cell (for example, for the synthesis of an extracellular matrix) and is used for the synthesis of an extracellular matrix or conversion of energy required for activity.

In some preferred embodiments, a biodegradable material in the carrier is a naturally occurring material (e.g., a naturally occurring biodegradable material derived from an animal or a plant, such as collagen, fibrin, chitosan, alginate, starch, hyaluronic acid, laminin, agarose, gelatin, dextran or any combination thereof), a synthetic material, a material produced by recombination, a modified material or any combination thereof.

In some preferred embodiments, a biodegradable material in the carrier is a naturally occurring degradable polymer. Preferably, the degradable polymer is selected from the group consisting of collagen, fibrin, chitosan, alginate, starch, hyaluronic acid, laminin, gelatin, dextran, elastin and any combination thereof.

In some preferred embodiments, the biodegradable material in the carrier is a modified degradable polymer, for example a modified alginate such as an oxidized alginate (e.g., oxidized sodium alginate).

In some preferred embodiments, a biodegradable material in the carrier is a synthetic degradable polymer, including but not limited to, polyphosphazenes, polyacrylic acids and a derivative thereof (e.g., polymethacrylic acid, copolymer of acrylic acid and methacrylic acid), polylactic acid (PLA), polyglycolic acid (PGA), polylactic acid-co-glycolic acid) (PLGA), polyorthoester (POE), polycaprolactone (PCL), polyhydroxybutyrate (PHB), polyamino acid (e.g., polylysine), biodegradable polyurethane, and any combination thereof.

In some preferred embodiments, the carrier further comprises water, an inorganic salt, a pH buffer, a stabilizer, a preservative or any combination thereof.

In some preferred embodiments, the carrier promotes placement of microcapsules (e.g., bio-blocks) on a construct, and/or immobilization of bio-blocks on a construct.

In some preferred embodiments, the carrier is a liquid or semi-liquid (e.g., a gel). In some preferred embodiments, the carrier has a viscosity of 1-1000 Pa·s, such as 30-160 Pa·s. Thus, In some preferred embodiments, the carrier has a viscosity of about 1, 2, 3, 4, 5, 6, 7, 8, 9, 10, 12, 14, 16, 18, 20, 25, 30, 50, 80, 100, 200, 300, 400, 500, 800 or 1000 Pa·s. In some preferred embodiments, the viscosity of the carrier is of 1-2, 2-3, 3-4, 4-5, 5-6, 6-7, 7-8, 8-9, 9-10, 10-12, 12-14, 14-16, 16-18, 18-20, 20-25, 25-30, 30-50, 50-80, 80-100, 100-200, 200-300, 300-400, 400-500, 500-800, or 800-1000, 1-3, 3-8, 8-16, 3-10, 10-20, 20-50, 50-160 Pa·s, or 30-160 Pa·s.

In some preferred embodiments, microcapsules having a first component attached to all or a part of the surface thereof used in the step (3) may be same as or different from microcapsules having a first component attached to all or a part of the surface thereof used in the step (5). In the case where microcapsules having a first component attached to all or a part of the surface thereof used in the step (5) are different from those in the step (3), the different microcapsules may be provided and the first component is allowed to attach to all or a part of the surface of the microcapsules prior to the step (5), thereby providing the microcapsules having a first component attached to all or a part of the surface which are different from those in the step (3).

In general, microcapsules (in particular, the cells contained in the microcapsules) used in the step (3) and the step (5) are selected according to cell distribution pattern of an artificial tissue progenitor to be prepared. For example, when a tubular biological construct to be prepared contains only one type of cells, microcapsules containing same cells may be used in step (3) and step (5). When a tubular biological construct to be prepared contains two or more types of cells, two or more types of microcapsules may be used in step (3) and step (5), each of which contains a different cell or a different combination of cells; or two or more types of microcapsules may be used in step (3) and step (5), which contain same undifferentiated cells and inducing factors that can induce differentiation of the undifferentiated cells into different adult cells.

As described in detail above, the first component and the second component of the present invention are not limited to a specific combination. Accordingly, the method of the present invention is also not limited to a specific combination of the first component and the second component. In addition, as to drawing/coating and microcapsule assembly for each round (for example, the steps (2) and (3) constitute one round of drawing/coating and microcapsule assembly, and the steps (4) and (5) constitute another round of drawing/coating and microcapsule assembly), a same or different combination of the first component and second component may be used. For example, the first combination of the first component and the second component may be used in the steps (2) and (3) of the present invention, while a same of different combination (i.e., another combination of the first component and the second component) may be used in the steps (4) and (5).

In some embodiments, for example, some embodiments of Method 7, the first combination of the first component and the second component (e.g., a combination of an anion-containing material and an alpha-cyanoacrylate) is used in the steps (2) and (3); while a combination that is different from the combination used in the steps (2) and (3) (for example, a combination that is different from the combination of an anion-containing material and an alpha-cyanoacrylate, e.g., a combination of fibrinogen and thrombin) is used in the steps (4) and (5).

As described above, each repetition of the steps (4) and (5) constitutes a round of microcapsule assembly. For each round of assembly of microcapsule units, same or different microcapsules may be used, and/or a same or different combination of the first component and second component may be used. In some preferred embodiments, for each round of microcapsule assembly, substitution of microcapsules, the first agent containing a first component and the second agent containing a second agent may be realized by replacing the ink in a corresponding ink cartridge, or by providing an additional ink cartridge.

In some preferred embodiments, the bio-printing steps (e.g., the steps (2)-(6)) in a method of the invention are continuous and/or substantially continuous. In some preferred embodiments, in the steps (2)-(6) of a method of the invention, a multilayer structure is continuously bio-printed to obtain a biological construct or artificial tissue progenitor having a predetermined pattern and comprising the multilayer structure. In some preferred embodiments, in the steps (2)-(6) of a method of the invention, each layer of the structure may be printed by using same or different microcapsules. In some preferred embodiments, a multilayer structure is printed by using one or more microcapsules, according to a predetermined pattern. In some preferred embodiments, in the steps (2)-(6) of a method of the invention, a plurality of segments is continuously bio-printed to obtain a biological construct or artificial tissue progenitor having a predetermined pattern and comprising the plurality of sections. In some preferred embodiments, in the steps (2)-(6) of a method of the invention, each segment may be printed by using same or different microcapsules. In some preferred embodiments, a plurality of segments may be printed by using one or more microcapsules, according to a predetermined pattern.

Beside the methods described above, the application also provides the following method for preparing an artificial tissue progenitor:

Method 8: a method of preparing an artificial tissue progenitor that is in a form of tube, comprising the following steps:

(I) preparing a tubular (e.g., in a shape of a round tube; e.g., in a shape of a tube with or without an opening at side wall) biological construct; and (II) attaching the tubular biological construct to the inner wall of a tubular solid support.

In some preferred embodiments, a biological construct is prepared by using a 3D bio-printer.

In some preferred embodiments, the 3D bio-printer comprises a first ink cartridge for providing a bio-ink, a second ink cartridge for providing an adhesive, a first printer head connected to the first ink cartridge, a rotary rod covered with an elastic film on the out wall, and a second printer head connected to the second ink cartridge.

In some preferred embodiments, the method comprises the following steps:

(1) providing a bio-ink in a first ink cartridge of a 3D bio-printer, wherein the bio-ink comprises a carrier and one or more microcapsules, and providing an adhesive in a second ink cartridge of the 3D bio-printer;

(2) printing the bio-ink on a predetermined area of an elastic film which is covered on the out wall of a rotary rod of the 3D bio-printer via a first printer head connected to the first ink cartridge of the 3D bio-printer, and obtaining a tubular biological construct;

(3) printing the adhesive on the tubular biological construct obtained in step (2) via a second printer head connected to the second ink cartridge of the 3D bio-printer, and obtaining an adhesive layer;

(4) sheathing a tubular solid support on the outer surface of the tubular biological construct having the adhesive layer obtained in step (3);

(5) expanding the elastic film, thus attaching the tubular biological construct to the inner wall of the tubular solid support, immobilizing the biological construct with the solid support by adhesive effect, and obtaining the artificial tissue progenitor.

Optionally, the method further comprises separating the artificial tissue progenitor from the elastic film.

Optionally, in the method, the step (2) and/or the step (3) may be repeated for one or more times.

Optionally, the 3D bio-printer also comprises a temperature control/adjustment component, which can be used to control/adjust the surface temperature of the rotary rod.

In some embodiments, the 3D bio-printer comprises a component for assembling. The step (4) may be realized by using the component for assembling. In some embodiments, the component for assembling comprises a hollow rod. In some embodiments, the step (4) comprises:

covering the tubular solid support outside the hollow rod;

covering the hollow rod outside the tubular biological construct having the adhesive layer; and leaving the tubular solid support outside the tubular biological construct while drawing out the hollow rod.

Optionally, the step (4) may be performed manually.

The elastic film on the rotary rod may play a role as an air bag. The elastic film can be expanded by filing it with air, making the biological construction on the elastic film move toward the outside, finally contact and stick with the inner wall of the solid support. The biological construction is evenly and completely attached to the inner wall of the solid support, forming an artificial tissue progenitor.

In some preferred embodiments, an artificial tissue progenitor of the present invention is used in tissue transplantation (for example, lumen transplantation, e.g., blood vessel transplantation). In some preferred embodiments, a cell distribution information of a tissue or lesion sites of tissue is obtained, prior to performing a method of the present invention. In some preferred embodiments, a method of the present invention further comprises obtaining a cell distribution information of a tissue or lesion sites of tissue and then preparing an artificial tissue progenitor in accordance with the cell distribution information. In some preferred embodiments, cells in microcapsules used in a method of the present invention are derived from a subject. In some preferred embodiments, cells in microcapsules used in a method of the present invention are derived from other subject having similar or identical characteristics (e.g., species, age, gender, genetic information, etc.) to the subject. In some preferred embodiments, cells in microcapsules used in a method of the present invention are derived from an allogeneic. In some preferred embodiments, cells in microcapsules used in a method of the present invention are derived from a cell line. In some preferred embodiments, a method of preparing an artificial tissue progenitor of the present invention is performed in vitro.

In some embodiments of the present invention (e.g., some embodiments of Methods 1-3, 8 or Method 5), a biological construct is immobilized with a solid support.

In some preferred embodiments, a biological construct is chemically attached to a solid support.

In some preferred embodiments, a biological construct is adhered to a solid support with an adhesive.

In some embodiments, the adhesive is a bio-adhesive.

In some embodiments, the adhesive is a medical adhesive.

In some preferred embodiments, the adhesive is an alpha-cyanoacrylate (e.g., methyl alpha-cyanoacrylate, ethyl alpha-cyanoacrylate, isobutyl alpha-cyanoacrylate, isohexyl alpha-cyanoacrylate, octyl alpha-cyanoacrylate).

In one aspect, the present invention relates to a biological construct obtained by a method for preparing a biological construct as defined in any one of the Methods 1, 2 and 3.

In one aspect, the present invention relates to a kit useful for preparing an artificial tissue progenitor, the kit comprising microcapsules, and a first agent and a second agent separated from each other, wherein the microcapsule comprises a cell and a biocompatible material encapsulating the cell, the first agent comprises a first component, the second agent comprises a second component, and when the first component is in contact with the second component, a sticky effect can be produced to achieve an adhesion effect.

In some preferred embodiments, the first component and the second component are capable of strong interacting (e.g., chemical reaction) upon contact and result in production of a sticky effect to achieve an adhesion effect. Such adhesion effect can not only achieve the adhesion between cells and cells, between cells and tissues and between tissues and tissues, but also achieve the adhesion between the cells/tissues and external substances. It is particularly preferred that such adhesion effect has at least one property selected from the group consisting of: (1) it is safe, reliable, non-toxic, non-carcinogenic, non-teratogenic and non-mutagenic; (2) it has a good biocompatibility, and does not hinder the self-healing of organic tissues; (3) it can be used under the conditions of bloods and tissue fluids; (4) it can realize fast adhesion under normal temperature and normal pressure; (5) it has good adhesive strength and durability, wherein the adhered portion has a certain elasticity and toughness; (6) it is non-irritable to organic tissues during use; (7) after the adhesive effect is achieved, relevant components can be gradually degraded and absorbed; and, (8) the adhered portion can allow cells to be migrated through.

In some preferred embodiments, the sticky effect resulting from the contact of the first component with the second component can be used to adhere the microcapsules together to form a construct; and the resulting construct thus obtained has a tensile modulus of not less than 10 Pa, for example, not less than 20 Pa, not less than 30 Pa, not less than 40 Pa, not less than 50 Pa, not less than 60 Pa, not less than 70 Pa, not less than 80 Pa, not less than 90 Pa, not less than 100 Pa, not less than 200 Pa, not less than 300 Pa, not less than 400 Pa, not less than 500 Pa, not less than 600 Pa, not Less than 700 Pa, no less than 800 Pa, no less than 900 Pa, or no less than 1000 Pa. In some preferred embodiments, the resulting construct thus obtained has a tensile modulus of up to 1 KPa to 10 Mpa, for example, 1 KPa to 5 KPa, 5 KPa to 10 KPa, 10 KPa to 50 KPa, 50 KPa to 100 KPa, 100 KPa to 500 KPa, 500 KPa to 1000 KPa, 1 MPa-5 MPa, or 5 MPa-10 MPa. In some preferred embodiments, the cells in the microcapsule are able to migrate through the adhered portion to enter into adjacent microcapsules or distant microcapsules. As a result, the cells in the microcapsules are able to grow, migrate, differentiate and proliferate throughout the construct.

In some preferred embodiments, the first component and the second component are selected from a combination of the following:

(1) fibrinogen and thrombin;

(2) alginate (e.g., sodium alginate) or oxidized alginate (e.g., oxidized sodium alginate), and a substance containing $Ca^{2+}$, $Mg^{2+}$, $Ba^{2+}$, $Sr^{2+}$ or $Fe^{3+}$ (for example, a solution or semi-solid (e.g., gel) containing $Ca^{2+}$, $Mg^{2+}$, $Ba^{2+}$, $Sr^{2+}$ or $Fe^{3+}$);

(3) maleimide group-containing molecule (e.g., polyethylene glycol containing a maleimide group (MAL-PEG)) and free thiol group-containing molecule (e.g., polyethylene glycol containing a free thiol group (PEG-SH));

(4) anion containing material (e.g., a solution or semi-solid (e.g., gel) containing anions) and alpha-cyanoacrylate (e.g., methyl alpha-cyanoacrylate, ethyl alpha-cyanoacrylate, isobutyl alpha-cyanoacrylate, isohexyl alpha-cyanoacrylate or n-octyl alpha-cyanoacrylate);

(5) fibrinogen and alpha-cyanoacrylate (e.g., methyl alpha-cyanoacrylate, ethyl alpha-cyanoacrylate, isobutyl alpha-cyanoacrylate, isohexyl alpha-cyanoacrylate or n-octyl alpha-cyanoacrylate);

(6) serum albumin (e.g., bovine serum albumin) and glutaraldehyde;

(7) molecule containing a carbamate group (—NHCOO—) or containing an isocyanate group (—NCO) (e.g., polyethylene glycol containing a carbamate group or polyethylene glycol containing an isocyanate group) and molecule containing reactive hydrogen (e.g., carboxyl-containing polyethylene glycol);

(8) gelatin-resorcinol and glutaraldehyde;

(9) carbodiimide cross-linked gelatin and poly-L-glutamic acid (PLGA); and

(10) aminated gelatin and polysaccharide aldehyde.

It should be particularly pointed out that as long as the first component and the second component can produce a sticky effect and achieve an adhesion effect by contacting, they can be used for carrying out the embodiments of the present invention. The first component and the second component of the present invention are not limited to the above specific combinations. In addition, when a certain combination is used as the first component and the second component, the first component may be any member of the combination and the second component is the other member of the combination. For example, when a combination of fibrinogen and thrombin is used, the first component may be fibrinogen (in this case the second component is thrombin), or may be thrombin (in this case the second component is fibrinogen).

In some preferred embodiments, the first component is fibrinogen and the second component is thrombin. In some preferred embodiments, the first component is an alginate (e.g., sodium alginate) or an oxidized alginate (e.g., oxidized sodium alginate), and the second component is a substance containing $Ca^{2+}$, $Mg^{2+}$, $Ba^{2+}$, $Sr^{2+}$ or $Fe^{3+}$, such as a solution or semi-solid (e.g., a gel) containing $Ca^{2+}$, $Mg^{2+}$, $Ba^{2+}$, $Sr^{2+}$ or $Fe^{3+}$. In some preferred embodiments, the first component is a maleimide group-containing molecule (e.g., polyethylene glycol containing a maleimide group (MAL-PEG)) and the second component is a free thiol group-containing molecule (e.g., polyethylene glycol containing a free thiol group (PEG-SH)). In some preferred embodiments, the first component is an anion containing material (e.g., a solution or semi-solid (e.g., a gel) containing anions), and the second component is an alpha-cyanoacrylate (e.g., methyl alpha-cyanoacrylate, ethyl alpha-cyanoacrylate, isobutyl alpha-cyanoacrylate, isohexyl alpha-cyanoacrylate or n-octyl alpha-cyanoacrylate). In some preferred embodiments, the first component is fibrinogen, and the second component is an alpha-cyanoacrylate (e.g., methyl alpha-cyanoacrylate, ethyl alpha-cyanoacrylate, isobutyl alpha-cyanoacrylate, isohexyl alpha-cyanoacrylate or n-octyl alpha-cyanoacrylate). In some preferred embodiments, the first component is serum albumin (e.g., bovine serum albumin), and the second component is glutaraldehyde. In some preferred embodiments, the first component is a molecule containing a carbamate group (—NHCOO—) or containing an isocyanate group (—NCO) (e.g., polyethylene glycol containing a carbamate group or polyethylene glycol containing an isocyanate group), and the second component is a molecule containing reactive hydrogen (e.g., carboxyl-containing polyethylene glycol). In some preferred embodiments, the first component is gelatin-resorcinol, and the second component is glutaraldehyde. In some preferred embodiments, the first component is carbodiimide cross-linked gelatin, and the second component is poly-L-glutamic acid (PLGA). In some preferred embodiments, the first component is an aminated gelatin, and the second component is a polysaccharide aldehyde.

In some preferred embodiments, in the first agent, the concentration of the first component is of 0.01% to 50% by weight. For example, in some preferred embodiments, the concentration of the first component is of 0.01-0.05 wt %, 0.05-0.1 wt %, 0.1-0.5 wt %, 0.5-1 wt %, 1-5 wt % 5-10 wt %, 10-15 wt %, 15-20 wt %, 20-25 wt %, 25-30 wt %, 30-35 wt %, 35-40 wt %, 40-45 wt % or 45-50 wt %.

In some preferred embodiments, in the second agent, the concentration of the second component is of 0.01% to 50% by weight. For example, in some preferred embodiments, the concentration of the second component is of 0.01-0.05 wt %, 0.05-0.1 wt %, 0.1-0.5 wt %, 0.5-1 wt %, 1-5 wt %, 5-10 wt %, 10-15 wt %, 15-20 wt %, 20-25 wt %, 25-30 wt %, 30-35 wt %, 35-40 wt %, 40-45 wt % or 45-50 wt %.

In some preferred embodiments, the second agent further comprises a third component, which is a tackifier. The viscosity of the second agent can be conveniently adjusted by adjusting the amount of the third component (tackifier) so that the second agent can maintain a particular shape, making it suitable for drawing patterns or for being coated. In some preferred embodiments, the third component is a biocompatible material. In some preferred embodiments, the third component is a bio-derived material. In some preferred embodiments, the third component is a biodegradable material. In some preferred embodiments, the third component is a temperature-sensitive material. In some preferred embodiments, the temperature-sensitive material has a different morphology at a different temperature. For example, the temperature-sensitive material (e.g., gelatin) is present in a solid or semi-solid at a lower temperature while in a liquid at a higher temperature. In some preferred embodiments, the temperature-sensitive material has a phase transition temperature of between 5 and 40° C., such as 5-10° C., 10-15° C., 15-20° C., 20-25° C., 25-30° C., 30-35° C. or 35-40° C. In certain preferred temperature-sensitive material is selected from the group consisting of gelatin, poly N-isopropylacrylamide, poly N-isopropylacrylamide-polyethylene glycol block copolymer, polyethylene glycol copolymer (e.g., polyvinyl alcohol-polyethylene glycol copolymer), agarose, Matrigel, chitosan/sodium glycerophosphate series, Pluronic F127 and poly N-isopropylacrylamide (PNIPAAm) hydrogel. In some preferred embodiments, the third component (tackifier) is selected from the group consisting of gelatin, block polymer F-127, agarose, polyethylene glycol, guar gum, polyvinyl alcohol, chitosan, collagen, hyaluronic acid, chitin, cellulose and a derivative thereof (such as hydroxypropyl cellulose), polyamine acid, poly N-isopropylacrylamide-polyethylene glycol block copolymer, polyethylene glycol copolymer (e.g., polyvinyl alcohol-polyethylene glycol copolymer), alginate (e.g., sodium alginate), a modified alginate (e.g., an oxidized alginate, such as oxidized sodium alginate), Matrigel, chitosan/sodium glycerophosphate series and poly N-isopropylacrylamide (PNIPAAm) hydrogel. In some preferred embodiments, the third component (tackifier) is gelatin.

In some preferred embodiments, in the second agent, the concentration of the third component is of 0.01% to 50% by weight. For example, in some preferred embodiments, the concentration of the third component is of 0.01-0.05 wt %, 0.05-0.1 wt %, 0.1-0.5 wt %, 0.5-1 wt %, 1-5 wt %, 5-10 wt %, 10-15 wt %, 15-20 wt %, 20-25 wt %, 25-30 wt %, 30-35 wt %, 35-40 wt %, 40-45 wt % or 45-50 wt %.

In some preferred embodiments, the microcapsules contained in the kit are microcapsules as defined in any of the above items.

In one aspect, the present application relates to a package useful for preparing a tubular biological construct, comprising one or more kits as defined above. In some preferred embodiments, a same combination of a first agent and a second agent is used in different kits. In some preferred embodiments, a different combination of a first agent and a second agent is used in different kits.

In some preferred embodiments, an artificial tissue progenitor of the present invention may be further cultured. Therefore, the present application also relates to an artificial tissue, which is obtained by culturing (for example, in vitro culturing or in vivo culturing) the artificial tissue progenitor of the present invention.

In some preferred embodiments, the artificial tissue is an artificial lumen.

In some preferred embodiments, the lumen is a lumen containing epithelial cells (e.g., blood vessel, esophagus, trachea, stomach, bile duct, gut (including small intestine and large intestine, such as duodenum, jejunum, ileum, cecum (including appendix), ascending colon, right colic flexure, transverse colon, left colic flexure, descending colon, sigmoid colon, rectum), fallopian tube, vas deferens, ureter, bladder or lymphatic vessel).

In some preferred embodiments, the artificial lumen is a tubular artificial lumen or a sheet-like artificial lumen.

In some preferred embodiments, the artificial lumen is an artificial blood vessel or vascular patch.

In some preferred embodiments, the artificial tissue progenitor is cultured under a condition that allow for proliferation, differentiation, migration, secretion and/or metabolism of cells within microcapsules. The culturing condition depend on the type of cells within microcapsules, the type of microcapsules used, the structure and shape of the artificial tissue progenitor, the culturing purpose, and the like. A person skilled in the art is able to select suitable culturing condition, including medium, pH, temperature, $CO_2$ level and duration. Culturing condition of a general tissue and cell can be found, for example, Doyle, Alan, and J. Bryan Griffiths, eds., "Cell and tissue culture: laboratory procedures in biotechnology", New York: Wiley, 1998. In some preferred embodiments, an artificial tissue progenitor is cultured for at least 0, 1, 2, 3, 4, 5, 6, 7, 8, 9, 10, 11, 12, 13, 14, 15, 16, 17, 18, 19, 20, 21, 25 or 30 days. In some preferred embodiments, an artificial tissue progenitor is cultured for 1-3, 3-5, 5-7, 7-10, 10-14, 14-21, 21-28, 1-7, 7-14, 1-14 or 14-28 days. In some preferred embodiments, the obtained artificial tissue progenitor is cultured in a 3D incubator. In some preferred embodiments, the obtained artificial tissue progenitor is cultured in a bioreactor. In some preferred embodiments, the obtained artificial tissue progenitor is cultured under a condition of 5% $CO_2$ at 37° C. In some preferred embodiments, an artificial tissue progenitor is subjected to a physical stimulation (e.g., pressure, shear force, light, heat, etc.) during the culturing. In some preferred embodiments, an artificial tissue progenitor is subjected to chemical stimulation (e.g., hormone, cytokine, chemical, etc.) during the culturing.

In some preferred embodiments, at least a portion of a biodegradable material in microcapsules is degraded during the culturing. In some preferred embodiments, the degradation product of such a biodegradable material provides a nutrient and/or an extracellular matrix to cells within the microcapsules. In some preferred embodiments, the biodegradable material in the microcapsules is degraded by at least 10%, at least 20%, at least 30%, at least 40%, at least 50%, at least 60%, at least 70%, at least 80% or at least 90%.

In some preferred embodiments, the cell in an artificial tissue progenitor secrete a secretion during culturing, and the secretion integrates into the artificial tissue progenitor. In some preferred embodiments, cells within microcapsules connect to each other during culturing. In some preferred embodiments, cells among the microcapsules connect to each other during culturing. In some preferred embodiments, the biological construct has a high cell density (e.g., at least 100, at least 200, at least 500, at least 1000, at least 2000, at least 5000, at least 10000, at least 20000, at least 50000 or at least 100000 cells/mm$^3$) after culturing. In some preferred embodiments, cells within microcapsules are proliferated by at least 2, at least 5, at least 10, at least 20, at least 50, at least 100, at least 200, at least 500, at least 1000, at least 2000, at least 5000, at least 10000, at least 20000, at least 50000 or at least 100000 times after culturing.

In some preferred embodiments, the artificial tissue progenitor is implanted in a non-human subject and cultured in the non-human subject.

In some preferred embodiments, the non-human subject is a mammal, such as a bovin, equine, caprid, suidae, canine, feline, rodent or a primate animal.

In another aspect, the present application provides a lumen implant, which comprises an artificial tissue progenitor (e.g., tubular artificial tissue progenitor or sheet-like artificial tissue progenitor) or an artificial lumen of the present invention.

In some preferred embodiments, the lumen implant comprises one or more (e.g., 2, 3, 4 or 5) of artificial tissue progenitors (e.g., tubular artificial tissue progenitors or sheet-like artificial tissue progenitors) of the present invention, or one or more (e.g., 2, 3, 4 or 5) artificial lumens (e.g., tubular artificial lumens or sheet-like artificial lumens) of the present invention.

In some preferred embodiments, the lumen implant comprises a plurality of (e.g., 2, 3, 4 or 5) of tubular artificial tissue progenitors of the present invention, wherein the plurality of tubular artificial tissue progenitors are in fluid communication.

In some preferred embodiments, the lumen implant comprises a plurality of (e.g., 2, 3, 4 or 5) of tubular artificial lumens of the present invention, wherein the plurality of tubular artificial lumens are in fluid communication.

In some preferred embodiments, the lumen implant is a linear tubular structure, or a branched tubular structure.

In some preferred embodiments, the lumen implant is in a form of an X-shaped tube, a Y-shaped tube or a T-shaped tube.

In some preferred embodiments, the lumen is a lumen containing epithelial cells (e.g., blood vessel, esophagus, trachea, stomach, bile duct, gut (including small intestine and large intestine, such as duodenum, jejunum, ileum, cecum (including appendix), ascending colon, right colic flexure, transverse colon, left colic flexure, descending colon, sigmoid colon, rectum), fallopian tube, vas deferens, ureter, bladder or lymphatic vessel).

In some preferred embodiments, the lumen containing epithelial cells is a blood vessel.

In some preferred embodiments, the lumen implant is a vascular implant comprising an artificial blood vessel or vascular patch of the present invention.

In some preferred embodiments, the lumen implant further comprises a pharmaceutically active ingredient, e.g., a pharmaceutically active ingredient for preventing thrombosis, calcification, infection and/or rejection.

In some preferred embodiments, the lumen implant further comprises a sensing device for detecting a fluid parameter within the lumen.

In some preferred embodiments, the lumen implant further comprises an adjustment device for adjusting a fluid parameter within the lumen.

In some preferred embodiments, the lumen implant is implanted in a subject's body.

In some preferred embodiments, the subject suffers from one or more of the following diseases: cardiovascular disease, cerebrovascular disease, peripheral vascular disease, orthopaedic disease, urological disease or oncological disease.

In some preferred embodiments, the subject suffers from one or more of the following: coronary heart disease, cerebral ischemic stroke, hemangioma, invasion of blood vessels by malignant tumor, thromboangiitis obliterans, orthopaedic disease caused by blocked blood transportation, or chronic renal failure.

In some preferred embodiments, the subject is a mammal, such as a bovin, equine, caprid, suidae, canine, feline, rodent or a primate animal; wherein a particularly preferred subject is a human.

The lumen implant of the present invention, such as an vascular implant, may be used to replace stenosed, occluded, dilated, damaged or deformed lumens (e.g., blood vessel) in a subject, or used for constructing a lumen bypass to functionally replace a stenosed, occluded, dilated, damaged or deformed lumen. The lumen implant of the present invention may be used as a lumen substitute in the case that the autologous lumen in a subject is insufficiently supplied. For example, an vascular implant of the present invention may be used in coronary artery bypass grafting (CABG) and applied in a subject with coronary heart disease, or in arteriovenous ostomy and applied in a subject with chronic renal failure.

In another aspect, the present application provides a method of replacing or repairing a lumen (e.g., blood vessel) of a subject, comprising implanting a lumen implant of the present invention into the subject.

In some preferred embodiments, the method is used for a therapeutic purpose. For example, a stenosed, occluded, dilated, injured or deformed lumen of a subject may be replaced with a lumen implant of the present invention.

In some preferred embodiments, the method is used for a non-therapeutic purpose. For example, a normal lumen of a non-human subject may be replaced with a lumen implant of the present invention for medical research.

In some preferred embodiments, the subject is a mammal, such as a bovin, equine, caprid, suidae, canine, feline, rodent or a primate animal; e.g. the subject is a human.

In another aspect, the present application relates to a lumen model, which comprises an artificial lumen of the present invention.

In some preferred embodiments, the lumen model comprise one or more (e.g., 2, 3, 4 or 5) of artificial lumens (for example, tubular artificial lumens, e.g., artificial blood vessels) of the present invention.

In some preferred embodiments, the lumen model comprises a plurality of (e.g., 2, 3, 4 or 5) of tubular artificial lumens of the present invention, wherein the plurality of tubular artificial lumens are in fluid communication.

In some preferred embodiments, the lumen model is a linear tubular structure, or a branched tubular structure.

In some preferred embodiments, the lumen model is in a form of an X-shaped tube, a Y-shaped tube or a T-shaped tube.

In some preferred embodiments, the lumen model further comprises a sensing device for detecting a fluid parameter within the lumen.

In some preferred embodiments, the lumen model further comprises an adjustment device for adjusting a fluid parameter within the lumen.

In some preferred embodiments, the lumen model is used in medical instructional demonstrations, screening of drugs (e.g., drugs used for preventing and/or treating a vascular disease, e.g., an active ingredient of drug), biological studies, or medical studies (e.g., studies of vascular fluid mechanics).

FIG. 5B exemplarily shows the shape of a lumen implant or lumen model of the present invention. A branched tubular artificial tissue progenitor (or tubular artificial lumen) may be obtained by connecting (e.g., gluing or suturing) linear tubular artificial tissue progenitors (or tubular artificial lumens) together, and thereby a branched lumen implant or lumen model is obtained.

In another aspect, the present application relates to use of an artificial tissue progenitor of the present invention in the manufacture of an artificial tissue, lumen implant or lumen model.

In some preferred embodiments, the artificial tissue is the artificial tissue (e.g., artificial lumen) as defined in any one of the above items.

In some preferred embodiments, the lumen implant is the lumen implant as defined in any one of the above items.

In some preferred embodiments, the lumen model is the lumen model as defined in any one of the above items.

In another aspect, the present application relates to use of an artificial tissue of the present invention in the manufacture of a lumen implant or lumen model.

In some preferred embodiments, the lumen implant is the lumen implant as defined in any one of the above items.

In some preferred embodiments, the lumen model is the lumen model as defined in any one of the above items.

Advantageous Effects of the Invention

Compared with the prior art, the technical solution of the present invention has one or more of the following advantageous effects:

1. In an artificial tissue progenitor of the present invention, the number of cells in microcapsules is generally consistent, and the microcapsules provide a suitable microenvironment for differentiation and/or growth of the cells, which is conducive to keep the stemness of cells and to maintain differentiation ability thereof, and the cells in a constructed tissue are more evenly distributed to facilitate the formation of a tissue having a complete structure and function.

2. An artificial tissue progenitor of the present invention is capable of forming a stable structure so that cells encapsulated therein can stay in a specific position. Microcapsules provide a mechanical protection to the cells so that the cells can withstand the impact of body fluids within a lumen during preparation of the artificial tissue progenitor and after implantation into a body, without being easily damaged or shed.

3. In an artificial tissue of the present invention, cells are evenly distributed and the artificial tissue is easy to form a complete structure and function.

4. In some preferred embodiments, adipose-derived mesenchymal stem cells are used to prepare an artificial tissue progenitor. Adipose-derived mesenchymal stem cells are readily available and are highly safe. Since adipose-derived mesenchymal stem cells have been used in in vitro and in vivo studies, a report on the tumorigenicity of adipose-derived mesenchymal stem cells has not been found.

5. An artificial tissue progenitor of the invention can be customized according to the demands of a patient to achieve personalized preparation.

6. In an artificial tissue progenitor of the present invention, a solid support is closely attached to microcapsules or a biological construct composed of the microcapsules, without relative movement.

Modes of Carrying Out the Invention

The invention will now be described with reference to the following examples which are intended to illustrate, but not to limit, the invention.

Reagents, kits or instruments whose sources are not indicated in the examples are all conventional products which are commercially available. A person skilled in the art will recognize that the examples illustrate the invention by way of exemplification and are not intended to limit the scope of the invention as claimed.

Example 1

Preparation of Bio-Blocks Containing Rhesus Adipose-Derived Mesenchymal Stem Cells 1. Collection and Culture of the Adipose-Derived Mesenchymal Stem Cells (1) Collection of the adipose-derived mesenchymal stem cells: a Rhesus monkey was used as an animal model, an adipose tissue was cut from the inguen and placed in a 50 mL centrifuge tube; the adipose tissue was digested with a pancreatic enzyme, and centrifuged to collect adipose-derived mesenchymal stem cells.

(2) Amplification of the adipose-derived mesenchymal stem cells by culturing in a serum-free Lonza medium. The photomicrograph of the fourth generation cells obtained by means of primary culture was shown in FIG. 6, and as can be seen from the figure, the morphology of cells was uniform and growth state of cells was good. The cells were collected by centrifugation.

2. Preparation of a Collagen Solution

Bovine type I collagen was used for the preparation of the solution:

(1) a 100 mL beaker and stirring magnet were treated by means of sterilization at an elevated temperature;

(2) the outer surface of the container was sterilized, and the container was placed in a biologically safe cabinet;

(3) 0.5 g of solid collagen which was sterilized with $Co^{60}$ irradiation was placed in the beaker, and 25 mL of sterile deionized water (which was filtered through a 0.22 μm filter) was added to the beaker;

(4) the solid collagen was immersed in water by stirring with the magnetic stirrer.

(5) an acetic acid solution (which was filtered through a 0.22 μm filter) was dropped to pH=3; and (6) the solution was stirred until the solid collagen was completely dissolved, and stored at 4° C.

Note: If the raw material was a solid collagen, the above procedures could be followed; if the raw material was a collagen solution, the solution could be used directly or used after diluted.

Depending on a concentration actually used, the collagen solution could be diluted with an ultrapure water (which was filtered through a 0.22 μm filter).

3. Preparation of Bin-Blocks Containing Adipose-Derived Mesenchymal Stem Cells (1) Preparation of a superhydrophobic well plate with an U-bottom: an well plate with an U-bottom was cleaned with alcohol in a superclean room, and then hydroxylated in a solution of hydrogen peroxide/concentrated sulfuric acid solution (30% (v/v), $H_2O_2:H_2SO_4=1:3$) at 80° C. for 1 hour. The hydroxylated well plate with an U-bottom was placed in a solution of 1% 1H,1H,2H,2H-perfluorodecyltriethoxysilane (purchased from Sigma) for 12 hours and then heated in a 100° C. oven for 4 hours for silicification. Finally, the well plate with an U-bottom was washed and dried.

(2) Preparation of a collagen solution containing seed cells: 45 μL of NaOH solution (4 mol/L) was mixed with 1 mL of collagen type I (4 mg/mL) to prepare a collagen solution of pH=7. The solution was mixed with the Rhesus adipose-derived mesenchymal stem cells to form a cell suspension (total cell concentration of $2\times10^7$ cells/mL).

(3) Preparation of a polylysine solution: polylysine (purchased from Sigma, with a number average molecular weight ($M_n$) of 150,000-300,000) was dissolved in a DMEM high glucose medium with a pH of 7.2 to give a polylysine solution having a concentration of 1 wt %.

(4) Dropping of collagen (formation of a core structure): by using an electronic suction device capable of aspirating and discharging a liquid at nanoliter level, 0.1 μL of the collagen solution containing seed cells was precisely drawn and dropped into the superhydrophobic well plate with an U-bottom prepared in step (1) to form a droplet, and the droplet was kept at a constant temperature of 37° C. for 30 minutes to shape.

An optional electronic suction device was Eppendorf Xplorer 0.5-10 μL or Transferpette Electronic 0.5-10 μL, and the device had a minimum volume of 0.1 μL relying on the separatory function thereof; or 1 μL or 0.5 μL of autosampler from SGE was used to achieve 0.1 μL liquid titration for 10 times or 5 times; in particular, a special conical needle could be used for the titration to improve accuracy.

(5) Dropping of the polylysine solution (formation of a shell structure): after suction end was replaced, 0.5 μL of the polylysine solution prepared in step (3) was accurately drawn, then dropped into the surface of the core formed in the step (4) in the central position of the superhydrophobic well plate, and reacted for 10 minutes to form a bio-block containing the Rhesus adipose-derived mesenchymal stem cells with a morphology shown in FIG. 7. FIG. 8 was a photograph of a bio-block containing Rhesus adipose-derived mesenchymal stem cells taken by a laser confocal microscopy, wherein the green fluorescence represented the shell of the bio-block and the red fluorescence represented the adipose-derived mesenchymal stem cells.

Example 2

Preparation of an Artificial Blood Vessel Progenitor Comprising Bio-Blocks and Expanded Polytetrafluoroethylene Using a 3D Bio-Printer, and In Vivo Application and Evaluation of the Artificial Blood Vessel Progenitor 1. Preparation Process:

(1) Preparation of a fibrinogen solution (5%) as a first agent: 0.1 g of fibrinogen was weighed and dissolved in 2 mL of saline (warmed in a 37° C. water bath for sufficient dissolution, if necessary sufficient); subsequently, the fibrinogen solution was filtered through a 0.22 μm filter for sterilization; and the filtered fibrinogen solution was stored for future use:

(2) Preparation of a thrombin solution (2000 U/mL) as a second agent: 0.0011 g of $CaCl_2$ was weighed, added to 2000 U thrombin (wherein the $Ca^{2+}$ concentration was of 10 mmol/mL), and then 1 mL of saline was added and dissolved; subsequently, the thrombin solution was filtered through a 0.22 μm filter for sterilization, and stored for future use.

(3) The bio-blocks prepared in Example 1 containing Rhesus monkey adipose-derived mesenchymal stem cells were immersed in the 5% fibrinogen solution (used as a first agent) for 5 minutes to attach/assemble the fibrinogen molecules on the surface of the bio-block (if necessary, a gentle shaking could be carried out to facilitate the assembly). The H-DMEM medium was added to the solution, and the bio-blocks were further immersed for another 5 minutes so as to remove the unassembled fibrinogen molecules from the surface of the bio-block, thereby obtaining immersed bio-blocks.

(4) By using a REVOTEK vascular bio-printer, a layer of gelatin with a thickness of 1 mm was printed on the rotary rod at 4° C. After the gelatin was solidified, the thrombin solution (used as a second agent) was sprayed on the surface of the gelatin.

(5) The bio-blocks were printed on the surface of the gelatin. The fibrinogens on the surface of the bio-blocks were cross-linked with each other under the action of thrombin, so that the bio-blocks were connected into one body to form a round tubular biological construct without an opening at side wall, and the construct had a length of 20 mm, a diameter of 6 mm and a wall thickness of 1 mm.

(6) The rotary rod was heated to 37° C., and the tubular construct was removed from the rotary rod.

(7) A layer of medical adhesive (medical EC type of Baiyun medical adhesive) was sprayed on the outer wall of the tubular biological construct. The expanded polytetrafluoroethylene tubular solid support was sleeved over the outer side of the tubular biological construct, and the outer wall of the biological construct was adhered to the inner wall of the expanded polytetrafluoroethylene tubular solid support through the medical adhesive to obtain an artificial blood vessel progenitor with a morphology shown in FIG. 9.

2. In Vivo Implantation

Step (1): Rhesus was subjected to a laparotomy so as to expose the abdominal aorta.

Step (2): the abdominal aorta was cut off, the two cut ends were sutured with the ends of an artificial blood vessel progenitor, respectively.

Step (3): the wound of abdomen in the animal was sutured.

3. Sampling and Pathological Examination

After 5 days of the operation, the artificial blood vessel was taken out. FIG. 10A showed the morphology of the artificial blood vessel. FIG. 10B showed the vascular tissue obtained by removing the tubular support, and FIG. 10C showed the morphology of longitudinal section of the tissue. The tissue was HE stained and immunohistochemically stained and compared with a normal blood vessel, and the results were shown in FIG. 11A to FIG. 13B.

FIG. 11A to FIG. 11B showed the result of HE staining. FIG. 11A involved in a normal blood vessel, and FIG. 11B involved in an artificial blood vessel. As shown in the figures, the artificial blood vessel and the normal blood vessel had a similar arrangement of cells, a similar layer of endothelial cells (as indicated by the thin arrow) and a similar layer of smooth muscle cells (as indicated by the thick arrow) to a normal blood vessel.

FIG. 12A to FIG. 12B showed the result of α-SMA staining, wherein α-SMA-positive cells were smooth muscle cells. FIG. 12A involved in a normal blood vessel, and FIG. 12B involved in an artificial blood vessel. As shown in the figures, the adipose-derived mesenchymal stem cells of the artificial blood vessel differentiated into smooth muscle cells, and showed similar cell morphology, alignment and directionality to a normal blood vessel.

FIG. 13A to FIG. 13B showed CD31 staining results, wherein CD31-positive cells were endothelial cells. FIG. 13A involved in a normal blood vessel, and FIG. 13B involved an artificial blood vessel. As shown in the figures, the adipose-derived mesenchymal stem cells of the artificial blood vessel differentiated into endothelial cells, and showed similar cell morphology and alignment to a normal blood vessel.

Example 3

Preparation of an Artificial Blood Vessel Progenitor Comprising Bio-Blocks and Polycaprolactone by Using a 3D Bio-Printer, and In Vivo Application and Evaluation of the Artificial Blood Vessel Progenitor 1. Preparation of a Tubular Polycaprolactone Solid Support Step (1): polycaprolactone was weighed and dissolved in tetrahydrofuran to prepare a preparation solution having a concentration of 2 wt %.

Step (2): an artificial blood vessel mold was immersed in the preparation solution and slowly taken out. After the solvent was evaporated, the procedures were repeated until a tubular polycaprolactone solid support having a tube wall thickness of 0.5 mm was obtained.

Step (3): the tubular polycaprolactone solid support was removed from the mold and rinsed with ultrapure water.

Step (4): the tubular polycaprolactone solid support was dried, cut to a desired length, and sterilized with ethylene oxide for future use.

2. Preparation of an Artificial Blood Vessel Progenitor Comprising Bio-Blocks and Polycaprolactone by Using a 3D Bio-Printer By using the bio-blocks containing Rhesus adipose-derived mesenchymal stem cells prepared in Example 1 and the tubular polycaprolactone solid support, a round tubular biological construct without an opening at side wall was prepared by a 3D printer, in accordance with the steps in Example 2. The tubular polycaprolactone solid support was sleeved over the outer side of the tubular biological construct; with a medical adhesive (medical EC type of Baiyun medical adhesive), the outer wall of the biological construct was adhered to the inner wall of the tubular polycaprolactone solid support to obtain an artificial blood vessel progenitor.

3. In Vivo Application and Evaluation of Artificial Blood Vessel Progenitor

The artificial blood vessel progenitor prepared in Example 3 was implanted into a Rhesus monkey, and the morphology and blood flow direction of a formed artificial blood vessel were examined after 6 days of the operation, and the results were shown in FIGS. 14A-14B.

FIG. 14A showed the result of ultrasonography. As could be seen from the figure, the lumen of the artificial blood vessel was unobstructed.

FIG. 14B showed the result of color Doppler imaging, and the result showed that blood flow on both sides of the artificial blood vessel was in the same direction, proving that that blood vessel was unobstructed.

The artificial blood vessel was taken out after 20 days of the operation, and the artificial blood vessel was examined by an immunohistochemistry process. The results were shown in FIG. 15A and FIG. 15B (the scales in the figures were of 200 μm).

FIG. 15A showed the result of α-SMA staining. As indicated by the thick arrow in the figure, the adipose-derived mesenchymal stem cells differentiated into smooth muscle cells in the artificial blood vessel. FIG. 15B showed the CD31 staining results, as indicated by the thin arrow in the figure, the adipose-derived mesenchymal stem cells differentiated into endothelial cells in the artificial blood vessel.

FIG. 15C showed the result of Sirius red staining. As shown in the figure, the artificial blood vessel formed a collagen structure similar to that of a normal blood vessel.

Example 4

Manual Construction of an Artificial Blood Vessel Progenitor Comprising Bio-Blocks and Expanded Polytetrafluoroethylene, and In Vivo Application and Evaluation of the Artificial Blood Vessel Progenitor 1. Preparation Process:

(1) The bio-blocks of Example 1 were immersed in a 5% fibrinogen solution for 5 minutes, then the fibrinogen solution was removed, an H-DMEM medium was added, and the bio-blocks were further immersed for 5 minutes.

(2) An expanded polytetrafluoroethylene artificial blood vessel (Gore artificial blood vessel, model: S0604, serial number: 3425) having a length of 1 cm was used as a tubular solid support, and 8 μL of medical adhesive (medical EC type of Baiyun medical adhesive) was drawn and uniformly coated on the inner wall of the expanded polytetrafluoroethylene blood vessel.

(3) The bio-blocks were attached to the inner wall of the expanded polytetrafluoroethylene blood vessel one by one, and the bio-blocks and the expanded polytetrafluoroethylene blood vessel were firmly adhered together under the action of the medical adhesive to obtain an artificial blood vessel progenitor.

2. In Vivo Application and Evaluation

The artificial blood vessel progenitor was implanted in a Rhesus monkey, sampled after 14 days, and examined by using an immunohistochemically staining method. The results were shown in FIG. 16A and FIG. 16B (the scales in the figures were of 50 μm).

FIG. 16A showed the result of α-SMA staining. As indicated by the thick arrow in the figure, the adipose-derived mesenchymal stem cells differentiated into smooth muscle cells in the artificial blood vessel.

FIG. 16B showed the result of CD31 staining. As indicated by the thin arrow in the figure, the adipose-derived mesenchymal stem cells differentiated into endothelial cells in the artificial blood vessel.

Example 5

Preparation of Microcapsules Containing Rhesus Adipose-Derived Mesenchymal Stem Cells (1) Preparation of a superhydrophobic well plate with an U-bottom: an well plate with an U-bottom was cleaned with alcohol in a superclean room, and then hydroxylated in a solution of hydrogen peroxide/concentrated sulfuric acid solution (30% (v/v), $H_2O_2:H_2SO_4=1:3$) at 80° C. for 1 hour. The hydroxylated well plate with an U-bottom was placed in a solution of 1% 1H,1H,2H,2H-perfluorodecyltriethoxysilane (purchased from Sigma) for 12 hours and then heated in a 100° C. oven for 4 hours for silicification. Finally, the well plate with an U-bottom was washed and air dried.

(2) Preparation of a collagen solution containing seed cells: 45 μL of NaOH solution (4 mol/L) was mixed with 1 mL of collagen type I (4 mg/mL) to prepare a collagen solution of pH=7. The solution was mixed with the Rhesus adipose-derived mesenchymal stem cells collected in Example 1 to form a cell suspension (total cell concentration of $2\times10^7$ cells/mL).

(3) Dropping of collagen (formation of a core structure): by using an electronic suction device capable of aspirating and discharging a liquid at nanoliter level, 0.1 μL of the collagen solution containing seed cells was precisely drawn and dropped into the superhydrophobic well plate with an U-bottom prepared in step (1) to form a droplet, and the droplet was kept at a constant temperature of 37° C. for 30 minutes to shape, whereby a microcapsule containing Rhesus adipose-derived mesenchymal stem cells was obtained.

Example 6

Manual Construction of an Artificial Blood Vessel Progenitor Comprising Microcapsules and Expanded Polytetrafluoroethylene, and In Vivo Application and Evaluation of the Artificial Blood Vessel Progenitor 1. Preparation Process.

(1) The microcapsules of Example 5 were immersed in a 5% fibrinogen solution for 5 minutes, then the fibrinogen solution was removed, an H-DMEM medium was added, and the microcapsules were further immersed for 5 minutes.

(2) An expanded polytetrafluoroethylene artificial blood vessel (Gore artificial blood vessel, model: S0604, serial number: 3425) having a length of 1 cm was used as a tubular solid support, and 8 μL of medical adhesive (medical EC type of Baiyun medical adhesive) was drawn and uniformly coated on the inner wall of the expanded polytetrafluoroethylene blood vessel.

(3) The microcapsules were attached to the inner wall of the expanded polytetrafluoroethylene blood vessel one by one, and the microcapsules and the expanded polytetrafluoroethylene blood vessel were firmly bonded together under the action of the medical adhesive to obtain an artificial blood vessel progenitor.

2. In Vivo Application and Evaluation

The artificial blood vessel progenitor was implanted in a Rhesus monkey, sampled after 14 days. FIG. 17A showed the cross-sectional view of an artificial blood vessel obtained. Immunohistochemically staining method was used for examination. The results were shown in FIG. 17B and FIG. 17C (the scales in the figures were of 50 μm).

FIG. 17B showed the result of α-SMA staining. As indicated by the thick arrow in the figure, the adipose-derived mesenchymal stem cells differentiated into smooth muscle cells in the artificial blood vessel.

FIG. 17C showed the result of CD31 staining. As indicated by the thin arrow in the figure, the adipose-derived mesenchymal stem cells differentiated into endothelial cells in the artificial blood vessel.

Example 7

Preparation of a Reinforced Artificial Blood Vessel Progenitor Comprising Bio-Blocks and Expanded Polytetrafluoroethylene by Using a 3D Bio-Printer (1) The bio-blocks of Example 1 were immersed in a 5% fibrinogen solution for 5 minutes, then the fibrinogen solution was removed, an H-DMEM medium was added, and the bio-blocks were further immersed for 5 minutes.

(2) A rotary rod with an outer diameter of 4 mm was prepared, and the bio-blocks prepared in the step (1) were printed on the rotary rod one by one to form a tubular biological construct.

(3) A medical adhesive of 8 μL was drawn and uniformly coated on the outer wall of the tubular biologic construct.

(4) An expanded polytetrafluoroethylene artificial blood vessel having a length of 1 cm and an inner diameter of 6 mm was prepared, and 8 μL of a medical adhesive was drawn and uniformly coated on the inner wall of the artificial blood vessel. The artificial blood vessel was sleeved from the left to right over the tubular biological construct. The medical adhesive coated on the inner wall of the artificial blood vessel was cured under the action of anions so that the artificial blood vessel and the tubular biological construct were adhered together to form an artificial blood vessel progenitor.

FIG. 18A to FIG. 18D showed the above preparing process. FIG. 18A: bio-blocks were printed on the rotary rod to form the tubular biological construct; FIG. 18B and FIG. 18C: the artificial blood vessel was sleeved from the left to the right over the tubular biological construct; FIG. 18D: the artificial blood vessel and the tubular biological construct were adhered together to form the artificial blood vessel progenitor.

Example 8

Manual Construction of an Artificial Blood Vessel Progenitor Comprising Bio-Blocks and Polylactic Acid A degradable polylactic acid tubular support and bio-blocks prepared in Example 1 were used to prepare an artificial blood vessel progenitor. FIGS. 19A-19D depicted the preparing process.

FIG. 19A and FIG. 19B showed a tubular solid support made of polylactic acid as a base material by an electro-spinning process.

FIG. 19C showed the following procedures: cutting off the polylactic acid tubular support, dropping a medical adhesive on one side of the tubular support, and placing bio-blocks on corresponding position of the other side of the tubular support.

FIG. 19D showed that the medical adhesive could penetrate through the tube wall so that the bio-blocks and the inner wall adhered together to obtain an artificial blood vessel progenitor.

The above procedures were only for the convenience of observation and photographing. In a practical preparation process, a medical adhesive was dropped on the outer wall of a polylactic acid tubular solid support so that the medical adhesive penetrate through into the inner wall. The medical adhesive could go through the wall of the electrospun polylactic acid, whereby the bio-blocks were immobilized. The above results showed that, on the one hand, polylactic acid could be used as a solid support, on the other hand, a medical adhesive could penetrate through the wall of a solid support obtained by electrospinning, due to the permeability of the porous structure of the solid support, and the medical adhesive could be dropped on one side of the solid support and bio-blocks could be placed on the other side, thereby immobilizing the bio-blocks and obtaining the artificial tissue progenitor.

Example 9

Preparation of a Tubular Biological Constructs with Bio-Blocks, Fibrinogen and Thrombin 1. Preparation of Bio-Blocks Containing Murine Bone Marrow Mesenchymal Stem Cells A bio-block which comprises murine bone marrow mesenchymal stem cells was prepared, having a core comprising collagen and a shell comprising sodium alginate. Method for preparing the bio-block was described in Chinese Patent Application 201610211570.4.

Experimental materials: bio-blocks (prepared according to the method described in Chinese Patent Application No. 201610211570.4), fibrinogen (bovine), thrombin (bovine), saline (medical-grade), $CaCl_2$, sterile water and gelatin (porcine).

2. Preparation of a Tubular Biological Construct (1) Preparation of a fibrinogen solution (5 wt %): 0.1 g of fibrinogen was weighed and dissolved in 2 mL of saline (warmed in a 37° C. water bath for sufficient dissolution, if necessary); subsequently, the fibrinogen solution was filtered through a 0.22 μm filter for sterilization; and the filtered fibrinogen solution (used as a first agent) was stored for future use.

(2) Preparation of a thrombin solution (2000 U/mL): 0.0011 g of $CaCl_2$ was weighed, added to 2000 U thrombin (wherein the $Ca^{2+}$ concentration was of 10 mmol/mL), and then 1 mL of saline was added and dissolved; subsequently, the thrombin solution was filtered through a 0.22 μm filter for sterilization, and stored for future use.

(3) Preparation of a gelatin solution (10 wt %): 1 g of gelatin was weighed and added to 10 mL of sterile water, and fully dissolved in a 37° C. water bath; and the gelatin solution was filtered through a 0.22 μm filter for sterilization, and stored for future use.

(4) 1 mL of the thrombin solution and 1 mL of the gelatin solution were mixed uniformly, and then placed in a 37° C. water bath for future use, that was, a second agent.

(5) The bio-blocks were immersed into the first agent for 10 minutes to attach/assemble fibrinogen molecules to the surfaces thereof (if necessary, a gentle shaking could be carried out to facilitate the assembly). The bio-blocks were then immersed in a cell culture medium for 5 minutes to wash away unassembled fibrinogen molecules on the surfaces thereof to obtain immersed bio-blocks.

(6) The bio-blocks were connected and assembled by utilizing a coagulation reaction of fibrinogen and thrombin to form a predetermined three-dimensional structure. The construction steps were as follows:

a. an annular pattern was drawn with the second agent in a glass plate in a 0° C. ice bath (the gelatin solution might be filled outside the annulus, if necessary, as an auxiliary material for constructing a tubular structure);

b. the bio-blocks were placed along the annular pattern and allowed to stand for 3 s to form an annular structure formed by bio-blocks (a first layer);

c. the second agent was dropped on the upper surface of the annular structure to draw an annular pattern;

d. the bio-blocks were placed along the annular pattern and allowed to stand for 3 s to form an annular structure formed by bio-blocks (a second layer);

e. the steps c-d was repeated as required to form annular structures having a different number of layers and formed by bio-blocks, i.e., a round tubular structure without an opening at side wall (if necessary, the tubular structure containing the auxiliary material could be placed in a 37° C. environment, and the auxiliary material was washed away).

FIG. 20A to FIG. 20G showed the experimental steps and experimental results for the preparation of the tubular three-dimensional construct using bio-blocks, fibrinogen and thrombin, wherein FIG. 20A showed that fibrinogen was attached/assembled on the surfaces of the bio-blocks; FIG. 20B showed that the annular auxiliary structure was constructed with an auxiliary material (optional step); FIG. 20C showed that the second agent was added dropwise along the annular auxiliary structure to draw a annular pattern; FIG. 20D showed that assembly units were placed on the annular pattern to form an annular structure; FIG. 20E showed that, a annular pattern was drawn on upper surface of the annular structure with the second agent and then assembly units were placed on the annular pattern (optionally, this step could be repeated for one or more times to construct a construct containing a multilayer structure); FIG. 20F showed the resulting tubular structure; FIG. 20G showed the removal of the auxiliary structure (optional step).

In addition, the tensile modulus of the obtained biological construct was measured using an electronic tensile tester (Model 5967, Instron) with reference to GB/T 228.1-2010 with a load of 10 N and a tensile speed of 20 mm/min, a temperature of 25° C., and the sample was kept wet during the measurement. The measurement results showed that the tensile modulus of the obtained tubular structure was of 1.25 KPa.

Further, the tubular structure was observed using OLYMPUS IX83 microscope immediately after preparation. The observation results were shown in FIG. 21A (Bar, 200 μm). The results showed that: in the immediately prepared tubular structure, the bio-blocks had not yet fused with each other, and the cells were uniformly distributed in each bio-block, respectively. The tubular structure was cultured in a DMEM high glucose medium for 3 days, and then observed by using the OLYMPUS IX83 microscope. The results were shown in FIG. 21B (Bar, 200 μm). The results showed that: in the cultured tubular structure, the bio-blocks were completely fused and closely connected with each other, and an intact biological construct was formed. These results demonstrated that the cells in the tubular structure were able to grow normally and to migrate through the adhered portion between the bio-blocks, and the fusion of the bio-blocks were achieved.

In Vivo Application and Evaluation of Artificial Blood Vessel Progenitors

In Examples 10-14, Rhesus monkeys were used as animal models, the artificial blood vessel progenitor prepared in Example 2 (which was used as a vascular implant) comprising bio-blocks and expanded polytetrafluoroethylene was implanted into a Rhesus monkey, and the situations were evaluated after implantation.

In Examples 10-14, the procedures for subjecting the artificial blood vessel progenitor and the autologous abdominal aorta of the Rhesus monkey to vascular anastomosis were performed by referring to the procedures in Example 2.

Example 10

11 Rhesus monkeys were numbered as NO. 1-NO. 11, wherein the NO. 11 was the control group. The artificial blood vessel progenitors and the autologous abdominal aorta of NO. 1-NO. 10 Rhesus monkeys were subjected to vascular anastomosis.

The vascular implant in each of the Rhesus monkeys was sampled and examined according to the times after implantation as shown in the following table

| Nos. | time |
|---|---|
| NO. 1 | 4 h, 7 d |
| NO. 2 | 8 h, 7 d |
| NO. 3 | 12 h, 7 d |
| NO. 4 | 24 h, 7 d |
| NO. 5 | 3 d, 7 d |
| NO. 6 | 5 d, 7 d |
| NO. 7 | 7 d |
| NO. 8 | 14 d |
| NO. 9 | 21 d |
| NO. 10 | 28 d |

(1) The tissue structure of the vascular implant was observed by HE staining method, and the results were shown in FIG. 22, wherein the scales in the figure were 200 µm. The results showed that after 4 hours of implantation, there were still gaps between the bio-blocks, and the bio-blocks were independent and not connected to each other. After 8 hours to 24 hours of implantation, the bio-blocks were gradually fused together. With the increase of time, an artificial blood vessel formed by fusion of bio-blocks gradually formed a histological structure similar to that of a normal blood vessel.

(2) The expression of CD31 was detected by using an immunohistochemical staining method, and the results were shown in FIG. 23 and FIG. 24. FIG. 23 showed the results magnified by 100 folds, and the scales in the figure were of 200 µm. FIG. 24 showed the results magnified by 400 folds, and the scales in the figure were of 50 µm. The results showed that, after 5 days of implantation, endothelial cells presented in the surface of the vascular implant in contact with the blood; with the increase of time, the number of endothelial cells increased continuously. On the $28^{th}$ day, an intact layer of endothelial cells that was similar to that of a normal blood vessel was formed.

(3) The expression of α-SMA was detected by using an immunohistochemical staining method, and the results were shown in FIG. 25, wherein the scales in the figure were 200 µm. The results showed that, after 8 hours of implantation, the adipose-derived mesenchymal stem cells encapsulated in the bio-blocks began to differentiate into smooth muscle cells and expressed α-SMA; after 3 days of implantation, the morphology of adipose-derived mesenchymal stem cells gradually change into that of smooth muscle cells and the expression of α-SMA further increased; with the increase of implantation time, the number of smooth muscle cells gradually increased, and a layer of smooth muscle cell layer that was similar to that of a normal blood vessel was formed.

Example 11

The artificial blood vessel progenitor and the autologous abdominal aorta of the Rhesus monkey were subjected to vascular anastomosis. The Rhesus monkeys were divided into 4 groups, and the junction between the vascular implant and autologous blood vessel of Rhesus monkey was sampled on the $7^{th}$, $14^{th}$, $21^{st}$ and $28^{th}$ after implantation, respectively. The tissue structure in the junction was observed by using HE staining method and the expressions of CD31 and α-SMA were detected by using immunohistochemical staining method, respectively.

FIG. 26 showed the results. The pictures in the first row were the results of HE staining, and the scale of the figures was of 200 µm; the pictures in the second row were the results of CD31 staining, and the scale of the figures was of 50 µm; and the pictures in the third row were the results of α-SMA, and the scale of the figures was of 200 µm. The thick arrows in the figures represented autologous blood vessels and the thin arrows indicated the vascular implants.

The results showed that: the vascular implant was connected to the autologous blood vessel of Rhesus monkey on $7^{th}$ day after implantation, but there was significant difference in tissue structure between them from each other, the layer of endothelial cells was continuous but not intact, and the layer of smooth muscle cells was discontinuous. As the time increased, the vascular implant continuously fused to the autologous blood vessel of Rhesus monkey; on the $28^{th}$ day after implantation, the vascular implant and the autologous blood vessel of Rhesus monkey fused together, the layer of endothelial cells and the layer of smooth muscle cells were continuous and intact, and formed a tissue structure similar to that of a normal blood vessel.

Example 12

The artificial blood vessel progenitor and the autologous abdominal aorta of the Rhesus monkey were subjected to vascular anastomosis. The Rhesus monkeys were divided into 4 groups, and the vascular implants were sampled on the $5^{th}$, $7^{th}$, $21^{st}$ and $28^{th}$ after implantation, respectively. The vascular collagen was stained by using a Sirius Red staining process, and the results were shown in FIG. 27, wherein the scales of the figures were 100 µm. The results showed that: the expression of the collagen appeared after 5 days of the implantation; as the time increased, the expressed collagen gradually increased and started to delaminate to form a collagen structure similar to that of a normal blood vessel.

Example 13

The artificial blood vessel progenitor and the autologous abdominal aorta of the Rhesus monkey were subjected to vascular anastomosis. The vascular implants were detected by ultrasonography on the $5^{th}$, $18^{th}$ and $61^{st}$ day after implantation, and the results were shown in FIG. 28. The results of the ultrasonography were shown in the pictures in the first row and results of the color Doppler imaging were shown in the pictures in the second row. The results showed that: the blood vessels in the vascular implants were unblocked and blood flows therein were continuous, the inner surface of lumen was smooth without thrombosis or abnormal proliferation, and there was no stenosis at the junction with the normal blood vessel.

Example 14

The artificial blood vessel progenitor and the autologous abdominal aorta of the Rhesus monkey were subjected to vascular anastomosis. The vascular implant was detected by an enhanced CT on the $19^{th}$ and $62^{nd}$ day after the implantation, and the results were shown in FIG. 29. The results showed that, in the vascular implant, the blood flowed smoothly without blockage.

Example 15

Preparation of a Vascular Patch Progenitor Comprising Bio-Blocks and Expanded Polytetrafluoroethylene by Using a 3D Bioprinter (1) A commercially available expanded polytetrafluoroethylene artificial blood vessel (wall thickness: 0.56 mm, inner diameter: 8 mm) was cut into an approximately rectangular sheet having a length of 4 cm and a width of 1 cm having a certain curvature to obtain a sheet-like solid support, as shown in FIG. 30A;

(2) A layer of medical adhesive (medical EC type of Baiyun medical adhesive) was sprayed on the sheet-like solid support;

(3) The bio-blocks containing the Rhesus adipose-derived mesenchymal stem cells prepared in Example 1 were immersed in a 5% fibrinogen solution for 5 minutes, then the fibrinogen solution was removed, then an H-DMEM medium was added, and the bio-blocks were further immersed for 5 minutes;

(4) The immersed bio-blocks were printed on the medical adhesive one by one by using a 3D bio-printer to cover the sheet-like solid support, thereby forming a vascular patch progenitor, as shown in FIG. 30B.

Example 16

Preparation of a Vascular Patch Progenitor Comprising Microcapsules and Polycaprolactone by Using a 3D Bio-Printer (1) a flat sheet-like polycaprolactone solid support having a thickness of 0.5 mm was prepared in accordance with the method of Example 3, and was cut into an approximately rectangular sheet having a length of 3.5 cm and a width of 1 cm, as shown in FIG. 30C;

(2) a layer of medical adhesive (medical EC type of Baiyun medical adhesive) was sprayed on the sheet-like solid support;

(3) the microcapsules containing the Rhesus adipose-derived mesenchymal stem cells prepared in Example 5 were printed on the medical adhesive one by one by using a 3D bio-printer to cover the sheet-like solid support, thereby forming a vascular patch progenitor, as shown in FIG. 30D.

Example 17

In Vivo Application and Evaluation of Vascular Patch Progenitor

Rhesus monkeys were used as animal models, and the vascular patch progenitors prepared in Examples 15 and 16 were in vivo implanted. After the vascular defect was created in the abdominal aorta of a Rhesus monkey, the vascular patch progenitor was cut to a proper oblong shape according to the specific vascular defect, and the vascular patch progenitor was sutured to the defect site.

FIG. 31A showed the creation of a vascular defect in the abdominal aorta of a Rhesus monkey, and FIG. 31B showed the suture of a vascular patch progenitor to the defect site. In FIG. 31B, what was indicated by the thick arrow was a vascular patch progenitor containing bio-blocks prepared in Example 15, and what was indicated by the thin arrow was a vascular patch progenitor containing microcapsules prepared in Example 16.

After 7 days of implantation, the vascular patches were taken out. FIG. 32A and FIG. 32B showed blood tissues respectively formed from a vascular patch progenitor containing bio-blocks and a vascular patch progenitor containing microcapsules. As shown in the figures, the bio-blocks or microcapsules in the patch were fused together to form an intact inner membrane.

The vascular tissue was subjected to CD31 and α-SMA immunohistochemical staining, and the results were shown in FIGS. 33A-33D.

FIG. 33A and FIG. 33B showed the results of a vascular tissue formed from a vascular patch progenitor containing bio-blocks. The results showed that the adipose-derived mesenchymal stem cells in the bio-blocks differentiated into endothelial cells (FIG. 33A) and smooth muscle cells (FIG. 33B), after 7 days of implantation.

FIG. 33C and FIG. 33D showed the results of a vascular tissue formed from a vascular patch progenitor containing microcapsules. The results showed that the adipose-derived mesenchymal stem cells in the microcapsules differentiated into endothelial cells (FIG. 33C) and smooth muscle cells (FIG. 33D), after 7 days of implantation.

Example 18

Preparation of Bio-Blocks Having Two Shells and Test of Mechanical Properties Thereof 1. Preparation of the Bio-Blocks (1) Preparation of a superhydrophobic well plate with an U-bottom: an well plate with an U-bottom was cleaned with alcohol in a superclean room, and then hydroxylated in a solution of hydrogen peroxide/concentrated sulfuric acid solution (30% (v/v), $H_2O_2:H_2SO_4=1:3$) at 80° C. for 1 hour. The hydroxylated well plate with an U-bottom was placed in a solution of 1% 1H,1H,2H,2H-perfluorodecyltriethoxysilane (purchased from Sigma) for 12 hours and then heated in a 100° C. oven for 4 hours for silicification. Finally, the well plate with an U-bottom was washed and air dried.

(2) Preparation of a collagen solution containing seed cells: 45 μL of a NaOH solution (4 mol/L) was mixed with 1 mL of collagen type I (4 mg/mL) to prepare a collagen solution of pH=7. The solution was mixed with the Rhesus adipose-derived mesenchymal stem cells obtained by centrifugation to form a cell suspension (total cell concentration of 2 cells×$10^7$/mL).

(3) Preparation of a polylysine solution: polylysine (purchased from Sigma, with a number average molecular weight ($M_n$) of 150,000-300,000) was dissolved in an H-DMEM medium with a pH of 7.2 to give a polylysine solution having a concentration of 1 wt %.

(4) Preparation of a solution of sodium alginate: sodium alginate (purchased from Sigma) was dissolved in an H-DMEM culture medium with a pH of 7.2 to give a sodium alginate solution having a concentration of 1 wt %.

(5) Dropping of collagen (formation of a core structure): by using an electronic suction device capable of aspirating and discharging a liquid at nanoliter level, 0.1 μL of the type I collagen solution was precisely drawn and dropped into the superhydrophobic well plate with an U-bottom prepared in step (1) to form a droplet, and the droplet was kept at a constant temperature of 37° C. for 30 minutes to shape.

An optional electronic suction device was Eppendorf Xplorer 0.5-10 μL or Transferpette Electronic 0.5-10 μL, and the device had a minimum volume of 0.1 μL per liquid relying on the separatory capability thereof; or 1 or 0.5 μL of autosampler from SGE was used to achieve 0.1 μL liquid titration for 10 times or 5 times; in particular, a special conical needle could be used for the titration to improve accuracy.

(6) Dropping of the polylysine solution: after suction end was replaced, 0.5 μL of the polylysine solution prepared in step (3) was accurately drawn, then dropped on the surface of the core formed in the step (5) in the central position of the superhydrophobic well plate, and reacted for 10 minutes to form a first shell of the bio-block.

(7) The product in the step (6) was rinsed for twice with H-DMEM culture medium.

(8) dropping the solution of sodium alginate: after suction end was replaced, 0.5 μL of the polylysine solution prepared in step (4) was accurately drawn, then dropped on the surface of the shell formed in the step (6) in the central position of the superhydrophobic well plate, and reacted for 10 minutes to form a second shell of the bio-block; whereby bio-block having two shells was obtained; and the prepared a bio-block had a diameter of about 300 μm.

Optionally, the prepared bio-blocks were placed in PBS to form a suspension of bio-blocks.

2. Measurements of Modulus of Elasticity

The modulus of elasticity of the bio-blocks was measured by using a Piuma Nanoindenter.

2.1 Preparation of Tested Samples (1) 1 of the suspension of bio-blocks was drawn and dropped in the middle of a plastic culture dish by a pipette;

(2) after standing for 10 minutes, the liquid was drained, and it could be seen that the bio-blocks were adsorbed on the bottom of the culture dish;

(3) the platform of the Nanoindenter was moved so that the probe gradually approached the surface of the bio-blocks; when the probe was close to the bio-blocks, a drop of water was drawn and dropped between the probe and the bio-blocks to ensure that the bio-blocks were in the normal physiological state;

(4) At this time, the bio-blocks were adsorbed on the bottom and could not move, and the measurement could be performed (see, FIG. 34).

2.2 Measurements of Samples
Measurement Conditions

| Hardness of probe (N/m) | Radium of probe (μm) | Poisson coefficient (v) | The minimum scope of application | The maximum scope of application |
|---|---|---|---|---|
| 0.46 | 52.5 | 0.5 | 65% | 85% |

Measurement Results

FIG. 35 showed the stress-strain curve of the bio-blocks prepared in the present example, wherein the effective Young's modulus of the bio-blocks was of 24.77 kPa.

Example 19

Preparation of an Artificial Blood Vessel Progenitor Comprising Bio-Blocks Having Two Shells by Using a 3D Bio-Printer and In Vivo Application and Evaluation of the Artificial Blood Vessel Progenitor 1. Preparation of a Collagen Solution (Solution A)

Bovine type I collagen was used for the preparation of the collagen solution as a carrier of bio-ink.

(1) a 100 mL beaker and stirring magnet were treated by means of sterilization at an elevated temperature;

(2) the outer surface of the container was sterilized, and the container was placed in a biologically safe cabinet;

(3) 0.5 g of solid collagen which was sterilized with $Co^{60}$ irradiation was placed in the beaker, and 25 mL of sterile deionized water (which was filtered through a 0.22 μm filter) was added to the beaker;

(4) the solid collagen was immersed in water by stirring with the magnetic stirrer.

(5) an acetic acid solution (which was filtered through a 0.22 μm filter) was dropped to pH=3; and (6) the solution was stirred until the solid collagen was completely dissolved;

(7) according to requirements in a printing process, the concentration of the collagen solution was adjusted. Without special requirements, the concentration of collagen solution was about 2 wt %. The collagen solution was labeled and named as Solution A, and stored at 4° C.

2. Preparation of an Artificial Blood Vessel Progenitor 2.1 Preparations (1) the Solution A was blended with the bio-blocks at an volume ratio of 1:1 to prepare a bio-ink A (bio-ink), the bio-ink A was filled in the printing ink cartridge A, and the temperature of the ink cartridge was kept at a temperature of 4° C.;

(2) the commercially available Baiyun medical adhesive as ink B was filled in the printing ink cartridge B, and the temperature of the ink cartridge was kept at room temperature;

(3) the ink cartridges A and B were connected with the corresponding printer heads;

(4) according to the results of imaging examination of a patient, the required diameter of a blood vessel was determined, and a corresponding rotary device was selected and installed;

(5) the 3D bio-printer was started to run self-test program, the height of printer head was measured, and normal works of various members of the 3D bio-printer were confirmed;

(6) the parameters were set in the computer workstation, including: diameter, length, printing order, printed thickness, temperature of the rotary device, temperature of the printer head.

FIG. 36 schematically showed the main structure of a 3D bio-printer used in the example.

2.2 Printing of a Biological Construct and Assembly with a Tubular Solid Support (1) the preparation program of the 3D bio-printer was started;

(2) the printer head A was run to print the ink A so as to form a tubular biological construct having a length of 20 mm and a thickness of about 1 mm on the rotary rod of the rotary device (as shown in FIG. 37);

(3) the printer head B was run to uniformly spray ink B on the biological construct formed from the ink A;

(4) a Gore expanded polytetrafluoroethylene artificial blood vessel having a matched size was used as a tubular solid support, which was sleeved over the outer surface of the tubular biological construct to be assembled, then the both were adhered together through the ink B (medical adhesive) to form an artificial blood vessel progenitor (as shown in FIG. 38), and the artificial blood vessel progenitor was removed from the rotary rod.

3. Implantation of an Artificial Blood Vessel Progenitor into a Rhesus Monkey for in Vivo Application and Evaluation 3.1 Surgical Procedure (1) A 5-7 cm longitudinal skin incision along the midline of the abdomen was cut, by a high frequency electrosurgical knife recommended, because the knife could cut and stop bleeding. Subcutaneous tissue and muscle layer were separated until the peritoneum. After entering and opening the abdominal cavity, the small intestine was gently turned over and wrapped with gauze soaked by saline to avoid dehydration, exposing the abdominal aorta;

(2) 0.5 mg·kg$^{-1}$ heparin sodium was intravenously injected for anticoagulation;

(3) two 0-0 suture threads were passed through below the artery, one of which was near the lower part of the mesenteric artery, the other was near the branch of the common iliac artery, and they were used for ligation to block blood flow when needed;

(4) arterial clips were used for blocking the blood flow of the infrarenal abdominal aorta, wherein the distance between the two arterial clips was about 3 cm, and an abdominal aorta of about 2 cm was cut from the middle of which;

(5) an artificial blood vessel progenitor having a length of 2 cm was sutured to the autologous abdominal aorta of the Rhesus monkey with a 7-0 polyethylene suture thread by end-to-end anastomosis;

(6) the arterial clip at the distal end of the aorta was loosen to empty the air in the artificial blood vessel progenitor;

(7) the arterial clip at the proximal end of the aorta was loosen, and the suture was pressed with a sterile gauze for a several minutes to prevent bleeding until there was no hematopedesis at the suture;

(8) the pulse of the distal aorta was detected; if the pulse was normal, the implantation was successful. FIG. 39 showed the implanted artificial blood vessel progenitor.

3.2 Histological Examination

After 170 days of the in vivo implantation, the vascular implant was sampled. The formation of endothelial cells and smooth muscle cells in the implant was detected by an immunofluorescence method.

The vascular endothelial cells were fluorescently labeled with green fluorescence, and the results showed that the vascular implant formed an intact layer of endothelial cells. FIG. 40 showed the fluorescence photomicrograph, wherein the scale in the figure was of 200 μm.

The vascular smooth muscle cells were fluorescently labeled with red fluorescence, and the results showed that vascular implant formed an intact layer of smooth muscle cells. FIG. 41 showed the fluorescence photomicrograph, wherein the scale in the figure was of 200 μm.

Example 20

Preparation of an Artificial Blood Vessel Progenitor by Using a 3D Bio-Printer

Bio-blocks and bio-ink were prepared in accordance with the method of Example 18 and Example 19, and Baiyun medical adhesive was used as bio-adhesive. An artificial blood vessel progenitor was prepared by using a 3D bio-printer. FIGS. 42A-42H shows the 3D bio-printer (FIG. 42A) and the steps of printing (FIG. 42B-H).

As shown in FIG. 42A, the 3D bio-printer comprises two printer heads for injecting bio-ink and bio-adhesive respectively; the 3D bio-printer further comprises a rotary device, which comprises a rotary rod covered with an elastic film on the outer wall, and a component (comprising a hollow rod) for assembling.

The steps are as following:

(1) the bio-ink is extruded through the printer head to form a bio-ink coating on the elastic film of the rotary rod (FIG. 42B);

(2) the bio-ink coating on the rotary device is subjected to a preforming process at low temperature (2° C., 25 min) (FIG. 42C);

(3) the bio-adhesive is evenly printed onto the bio-ink coating through the printer head (FIG. 42D);

(4) after printing the bio-adhesive, a Gore artificial blood vessel was immediately covered outside the bio-ink coating via the component for assembling (FIG. 42E);

(5) after assembling, the elastic film was expanded by filling it with air, making the bio-ink contact with the inner wall of Gore artificial blood vessel, and making them stick together by the bio-adhesive; the expanding is continued for 10 s;

(6) the assembled blood vessel progenitor was removed from the rotary device (FIG. 42F-G);

(7) the blood vessel progenitor was immersed in blood vessel preservation solution (FIG. 42H).

Example 21

In Vivo Application and Evaluation of Artificial Blood Vessel Progenitor

The artificial blood vessel progenitor prepared in Example 20 was used for a bypass operation between the abdominal aorta to the arteria iliaca communis in a Wuzhishan miniature pig as an animal model. FIG. 43 and FIG. 44 show the results of CT examination and color Doppler imaging 7 days after the operation. The results show that the blood flows smoothly in the implanted artificial blood vessel, and there is no stenosis or abnormal proliferation. Samples were taken for immunofluorescence test 63 days after the operation. α-SMA was used for labelling smooth muscle cells and CD31 was used for labelling endothelial cells. As shown in FIG. 45, the artificial blood vessel progenitor formed ordered-arranged layers of endothelial cells and smooth muscle cells and fused with the autologous blood vessel.

Although specific embodiments of the present invention have been described in detail, a person skilled in the art will understand that various modifications and changes may be made to the details according to all the teachings disclosed in the present invention, and these alterations are within the protection scope of the present invention. The full scope of the present invention is given by the appended claims and any equivalents thereof.

The invention claimed is:

1. An artificial tissue progenitor comprising a solid support and a plurality of microcapsules, wherein each of the microcapsules comprises cells, a core and a shell, wherein the core encapsulates 25-5000 cells and the shell encloses the core, and wherein the core and the shell are independently made from a biodegradable polymeric material, wherein the biodegradable polymeric material for preparing the core is collagen, and the biodegradable polymeric material for preparing the shell is polylysine;

the cells are selected from the group consisting of adipose-derived mesenchymal stem cells, and bone marrow mesenchymal stem cells;

the artificial tissue progenitor is a tube, the solid support is a tubular solid support, the plurality of microcapsules forms one tubular biological construct, and the tubular biological construct has an outer wall attached to the inner wall of the tubular solid support by a medical adhesive; and the artificial tissue progenitor is a blood vessel progenitor.

2. The artificial tissue progenitor of claim 1, having one or more features selected from the following:

(1) the microcapsules each independently have a size of 100-2000 μm;

(2) the microcapsules are each independently spherical;

(3) the microcapsules are in a gel state;

(4) the cells are adipose-derived mesenchymal stem cells and;

(5) the cells are obtained from a human, a monkey, a pig or a dog.

3. The artificial tissue progenitor of claim 1, having one or more features selected from the following:

(1) the artificial tissue progenitor has an inner diameter of 1 mm to 3 cm;

(2) the artificial tissue progenitor has a uniform thickness;

(3) the tubular solid support has a length of 1 cm to 40 cm; and (4) the tubular solid support has an inner diameter of 1 mm to 3 cm.

4. The artificial tissue progenitor of claim 1, wherein the medical adhesive is a tissue adhesive comprising octyl 2-cyanoacrylate.

5. The artificial tissue progenitor of claim 1, wherein the medical adhesive comprises alpha-cyanoacrylate.

6. A method of preparing the artificial tissue progenitor according to claim 1, wherein the artificial tissue progenitor is in a form of tube, wherein the method comprises the following steps:

(I) preparing the tubular biological construct; and (II) attaching the tubular biological construct to the inner wall of the tubular solid support.

7. The method of claim 6, wherein the tubular biological construct is prepared by a 3D bio-printer.

8. The method of claim 7, wherein the 3D bio-printer comprises a first ink cartridge for providing a bio-ink, a second ink cartridge for providing the medical adhesive, a first printer head connected to the second ink cartridge, a second printer head connected to the second ink cartridge, and a rotary rod, wherein the outer wall of the rotary rod is covered with an elastic film.

9. The method of claim 6, comprising the following steps:

(1) providing a bio-ink in a first ink cartridge of a 3D bio-printer, wherein the bio-ink comprises a carrier and one or more microcapsules, and providing the medical adhesive in a second ink cartridge of the 3D bio-printer;

(2) printing the bio-ink on a predetermined area of an elastic film which is covered on the out wall of a rotary rod of the 3D bio-printer via a first printer head connected to the first ink cartridge of the 3D bio-printer, and obtaining the tubular biological construct;

(3) printing the medical adhesive on the tubular biological construct obtained in step (2) via a second printer head connected to the second ink cartridge of the 3D bio-printer, and obtaining a medical adhesive layer;

(4) sheathing the tubular solid support on the outer surface of the tubular biological construct with the medical adhesive layer obtained in step (3);

(5) expanding the elastic film, thus attaching the tubular biological construct with the adhesive layer to the inner wall of the tubular solid support, immobilizing the biological construct with the solid support by the medical adhesive, and obtaining the artificial tissue progenitor;

optionally, the method further comprises separating the tubular biological construct from the elastic film.

10. An artificial blood vessel or a vascular patch obtained by culturing the artificial tissue progenitor according to claim 1.

11. A lumen implant comprising an artificial tissue progenitor according to claim 1 or an artificial blood vessel or a vascular patch obtained by culturing the artificial tissue progenitor according to claim 1.

12. The lumen implant according to claim 11, having a linear tubular structure.

13. A blood vessel model, comprising the artificial blood vessel according to claim 10 and having a linear tubular structure.

14. The artificial tissue progenitor according to claim 1, wherein the cells are adipose-derived mesenchymal stem cells.

* * * * *